(12) United States Patent
Monahan et al.

(10) Patent No.: US 12,203,076 B2
(45) Date of Patent: Jan. 21, 2025

(54) METHOD FOR INTRODUCING MUTATIONS

(71) Applicant: Illumina Singapore Pte. Ltd., Northtech (SG)

(72) Inventors: Leigh G. Monahan, Sydney (AU); Joyce To, Sydney (AU); Catherine Maree Burke, Sydney (AU); Michael Imelfort, Sydney (AU); Aaron Earl Darling, Sydney (AU)

(73) Assignee: Illumina Singapore Pte. Ltd., Northtech (SG)

( * ) Notice: Subject to any disclaimer, the term of this patent is extended or adjusted under 35 U.S.C. 154(b) by 111 days.

(21) Appl. No.: 17/807,835

(22) Filed: Jun. 20, 2022

(65) Prior Publication Data

US 2022/0348940 A1 Nov. 3, 2022

Related U.S. Application Data

(62) Division of application No. 16/971,293, filed as application No. PCT/GB2019/050443 on Feb. 19, 2019, now Pat. No. 11,421,238.

(30) Foreign Application Priority Data

Feb. 20, 2018 (GB) .................................. 1802744

(51) Int. Cl.
*C12Q 1/68* (2018.01)
*C07K 14/00* (2006.01)
(Continued)

(52) U.S. Cl.
CPC .............. *C12N 15/66* (2013.01); *C07K 14/00* (2013.01); *C12N 9/1252* (2013.01);
(Continued)

(58) Field of Classification Search
None
See application file for complete search history.

(56) References Cited

U.S. PATENT DOCUMENTS 5,780,231 A 7/1998 Brenner
5,955,280 A * 9/1999 Vidal .................. C12Q 1/6897
435/254.2
(Continued)

FOREIGN PATENT DOCUMENTS

CN 103555685 2/2014
CN 104232761 A 12/2014
(Continued)

OTHER PUBLICATIONS

Mitchelson, Sequencing of Difficult DNA Regions by SAM Sequencing, Ch. 6, in Methods in Molecular Biology, MIMB, vol. 687, pp. 75-88, First Online: Jan. 1, 2010.*

(Continued)

*Primary Examiner* — Aaron A Priest
(74) *Attorney, Agent, or Firm* — Knobbe, Martens, Olson & Bear, LLP

(57) ABSTRACT

The present invention relates to a method for introducing mutations into at least one target nucleic acid molecule comprising (a) providing at least one sample comprising at least one target nucleic acid molecule; and (b) amplifying the at least one target nucleic acid molecule using a low bias DNA polymerase. The present further relates to a use of a low bias DNA polymerase in a method for introducing mutations into one or more nucleic acid molecule(s), a group of sample tags, a method for designing the group of sample tags, a computer readable medium, and a method for preferentially amplifying target nucleic acid molecules.

29 Claims, 18 Drawing Sheets

Specification includes a Sequence Listing.

(51) Int. Cl.
    C12N 9/12      (2006.01)
    C12N 15/10     (2006.01)
    C12N 15/66     (2006.01)
(52) U.S. Cl.
    CPC ........... *C12N 15/1065* (2013.01); *C12Q 1/68* (2013.01); *C12Q 2521/101* (2013.01); *C12Q 2525/191* (2013.01); *C12Q 2531/113* (2013.01)

(56)  References Cited

U.S. PATENT DOCUMENTS

| | | | |
|---|---|---|---|
| 7,704,713 B2* | 4/2010 | Sato ..................... | C12N 9/1252 435/5 |
| 9,481,912 B2 | 11/2016 | Fischer | |
| 11,162,135 B2 | 11/2021 | Makarov et al. | |
| 11,421,238 B2 | 4/2022 | Monahan et al. | |
| 2002/0123113 A1* | 9/2002 | Tsien ..................... | C12N 15/65 435/325 |
| 2003/0215914 A1* | 11/2003 | Houtzager ....... | C07K 14/70503 506/17 |
| 2005/0032177 A1* | 2/2005 | Hogrefe ............... | C12N 15/102 435/91.2 |
| 2012/0183960 A1 | 7/2012 | Hoerr et al. | |
| 2014/0295498 A1* | 10/2014 | Turner ................. | C12Q 1/6853 435/194 |
| 2016/0340746 A1 | 11/2016 | Makarov et al. | |

FOREIGN PATENT DOCUMENTS

| | | |
|---|---|---|
| CN | 107760771 A | 3/2018 |
| CN | 107955806 A | 4/2018 |
| WO | WO 02/079502 A1 | 10/2002 |
| WO | WO 04/038007 | 5/2004 |
| WO | WO 2009/108949 A2 | 9/2009 |
| WO | WO 11/106368 | 9/2011 |
| WO | WO 2014/013218 A1 | 1/2014 |
| WO | WO 2016/057947 A1 | 4/2016 |
| WO | WO 2017/059582 A1 | 4/2017 |
| WO | WO 2020/087076 A1 | 4/2020 |

OTHER PUBLICATIONS

Choi et al., "The use of modified and non-natural nucleotides provide unique insights into pro-mutagenic replication catalyzed by polymerase eta", Nucleic Acids Research, 2016, vol. 44, No. 3, 1022-1035.
Cochran et al., "Sequencing by Aligning Mutated DNA Fragments (SAM)" in Xing et al. (eds.), Frontiers in Biochip Technology, Springer, Boston, MA, 2 pages (2006).
Elshawadfy et al., "DNA polymerase hybrids derived from the family-B enzymes of Pyrococcus furiosus and Thermococcus kodakarensis: improving performance in the polymerase chain reaction", Frontiers in Microbiology, May 2014, vol. 5, article 224, 1-14.
Harris et al., "The Effect of Tautomeric Constant on the Specificity of Nucleotide Incorporation during DNA Replication: Support for the Rare Tautomer Hypothesis of Substitution Mutagenesis", J. Mol. Biol. 2003, 326, 1389-1401.
Keith et al., "A simulated annealing algorithm for finding consensus sequences", Bioinformatics, 18(11); 1494-1499 (2002).
Keith et al., "Chapter 10: Sequencing Aided by Mutagenesis Facilitates the De Novo Sequencing of Megabase DNA Fragments by Short Read Lengths", Perspectives in Bioanalysis, vol. 2, pp. 303-326 (2007).
Keith et al., "Unlocking hidden genomic sequence", Nucleic Acids Research, vol. 32, No. 3, pp. E35-E43 (2004; published online Feb. 18, 2004).
Kong et al., "Synthesis and duplex stability of oligonucleotides containing cytosine-thymine analogues", Nucleic Acids Research, vol. 17, No. 24, 1989, 10373-10383.
Kuwahara et al., "Study on Suitability of KOD DNA Polymerase for Enzymatic Production of Artificial Nucleic Acids Using Base/Sugar Modified Nucleoside Triphosphates", Molecules 2010, 15, 8229-8240.
Levy et al., "Facilitated sequence counting and assembly by template mutagenesis", PNAS, E4362-E4637.
Moore et al., "Direct Observation of Two Base-pairing Modes of Cytosine-Thymine Analogue with Guanine in DNA Z-form Duplex: Significance for Base Analogue Mutagenesis", J. Mol. Biol. 1995, 251, 665-673.
Nedderman et al., "Molecular Basis for Methoxyamine-initiated Mutagenesis: $^1$H Nuclear Magnetic Resonance Studies of Oligonucleotide Duplexes Containing Base-modified Cytosine Residues", J. Mol. Biol. 1993, 230, 1068-1076.
Petrie et al., "Deep sequencing analysis of mutations resulting from the incorporation of dNTP analogs", Nucleic Acids Research, 2010, vol. 38, No. 22, 8095-8104.
Sawai et al., "Expression of structural and functional diversities of DNA using new 5-substituted deoxyuridine derivatives by PCR with superthermophilic KOD Dash DNA polymerase", Chem. Commun., 2001, 2604-2605, Nov. 14, 2001.
Shen, "PCR Approaches to DNA Mutagenesis and Recombination", Methods in Molecular Biology, vol. 192, PCR Cloning Protocols, 2nd Edition, 167-174.
Sipos et al., "An Improved Protocol for Sequencing of Repetitive Genomic Regions and Structural Variations Using Mutagenesis and Next Generation Sequencing" PLoS One, vol. 7, issue 8, e43359, 9 pages (Aug. 2012).
Stone et al., "Molecular basis for Methoxyamine-initiated Mutagenesis: $^1$ H Nuclear Magnetic Resonance Studies of Base-modified Oligodeoxynucleotides", J. Mol. Biol., 1991, 222, 711-723.
Yamashita et al., "Characterization of Recombinant Thermococcus kodakaraensis (KOD) DNA Polymerases Produced Using Silkworm-Baculovirus Expression Vector System", Mol. Biotechnol., 2017, 59, 221-233.
Zaccolo et al., "An Approach to Random Mutagenesis of DNA Using Mixtures of Triphosphate Derivatives of Nucleoside Analogues", J. Mol. Biol., 1996, 255, 589-603.
Spee et al., Feb. 11, 1993, Efficient random mutagenesis method with adjustable mutation frequency by use of PCR and dITP, Nucleic Acids Research, 21(3):777-778.
Jin Jing, May 15, 2012, An Novel Fluorescent NADH Reporter, masters' thesis, East China University of Science and Technology (Abstract and TOC), 4 pp.
Koyanagi et al., Apr. 2008, A rapid, simple, and effective method of constructing a randomly mutagenized plasmid library free from ligation, Biosci Biotechnol Biochem, 72(4):1134-1137.
Dubendorff et al., 1991, Controlling basal expression in an inducible T7 expression system by blocking the target T7 promoter with lac repressor, Journal of Molecular Biology. 219(1):45-59.
Keith et al., "Algorithms for sequence analysis via mutagenesis," Bioinformatics, 20(15):2401-2410 (2004).
Lin et al., 1989, Synthesis and duplex stability of oligonucleotides containing cytosine-thymine analogues, Nucleic Acids Research, 17(24): 10373-10383.
Pochet et al., 1997, Ambiguous base pairing of 1-(2-deoxy-β-D-Ribofuranosyl)imidazole-4-carboxamide during PCR, Nucleoside, Nucleotides & Nucleic Acids, 16(7-9):1749-1752.
Sambrook et al., 1989, Molecular Cloning: A Laboratory Manual Second Ed., Cold Spring Harbor Laboratory Press, Cold Spring Harbor, New York (TOC).
International Search Report and Written Opinion dated Aug. 20, 2019 in application No. PCT/GB2019/050443.

* cited by examiner

FIG. 1
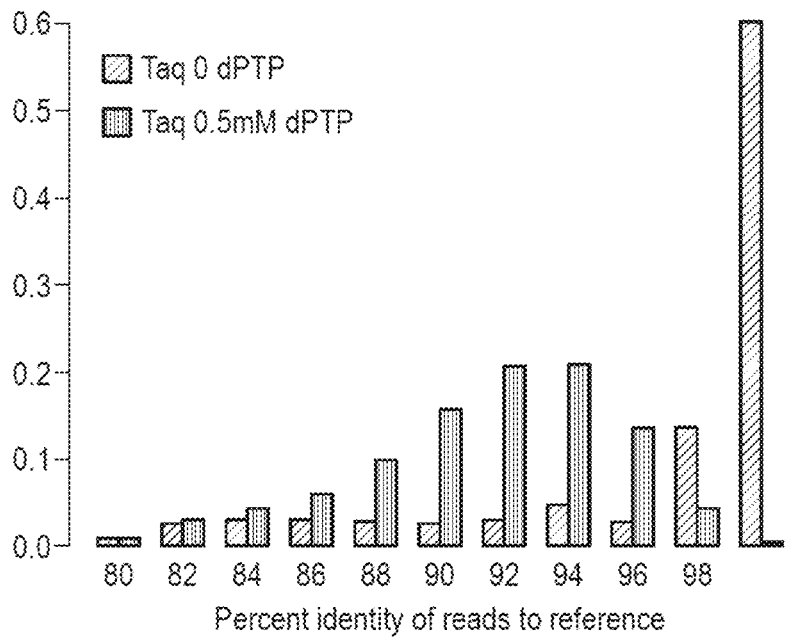
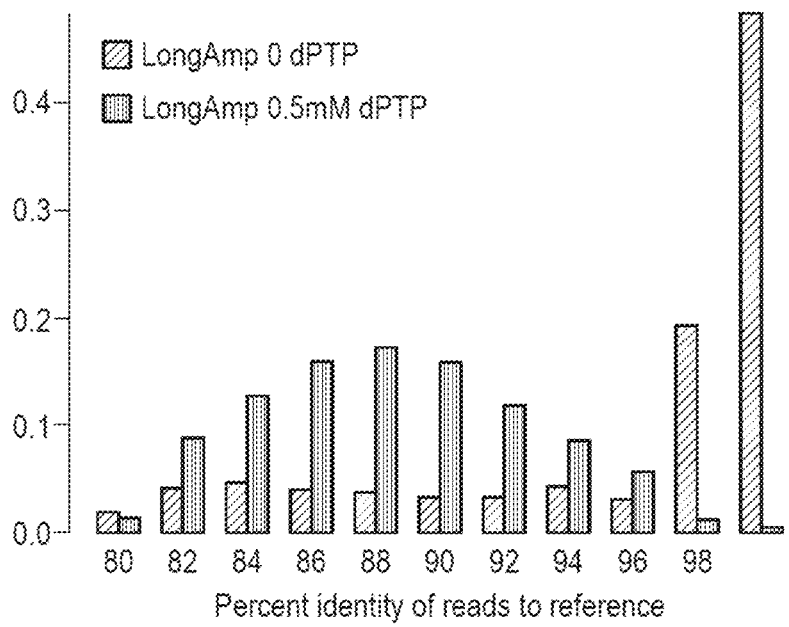

FIG. 3

SEQ ID NO: 1 – nucleotide sequence of DNA polymerase from Thermococcus sp. KS-1

```
atgatcctcg acactgacta cataactgag aatggaaaac ccgtcataag gattttcaag
aaggagaacg gcgagtttaa gattgagtac gataggactt ttgaaccota catttacgcc
ctcctgaagg acgattctgc cattgaggag gtcaagaaga taaccgccga gaggcacgga
acggttgtaa cggttaagcg ggctgaaaag gttcagaaga agttcctcgg agaccagtt
gaggtctgga aactctactt tactcaccct caggacgtcc cagcgataag ggacaagata
cgagagcatc cagcagttat tgacatctac gagtacgaca taccottcgc caagcgctac
ctcatagaca agggattagt gccaatggaa ggcgacgagg agctgaaaat gcttgccttt
gatatcgaga cgctctacca tgagggcgag gagttcgccg agggccaat cottatgata
agctacgccg acgaggaagg ggccagggtg ataacgtgga agaacgcgga tctgccctac
gttgacgtcg tctcgacgga gagggagatg ataaagcgct tcctaaaggt ggtcaaagag
aaagatcctg acgtcctaat aacctacaac ggcgacaact tcgacttcgc ctacctaaaa
aaacgctgtg aaaagcttgg aataaacttc acgctcggaa gggacggaag cgagccgaag
attcagagga tgggcgacag gtttgccgtc gaagtgaagg gacggataca cttcgatctc
tatcctgtga taagacggac gataaacctg cccacataca cgcttgaggc cgtttatgaa
gccgtcttcg gtcagccgaa ggagaaggtc tacgctgagg agatagctac agcttgggag
agcggtgaag gccttgagag agtagccaga tactcgatgg aagatgcgaa ggtcacatac
gagcttggga aggagttttt ccctatggag gcccagcttt ctcgttaat cggccagtcc
ctctgggacg tctcccgctc cagcactggc aacctcgttg agtggttcct cctcaggaag
gcctacgaga ggaatgagct ggccccgaac aagcccgatg aaaaggagct ggccagaaga
cgacagagct atgaaggagg ctatgtaaaa gagcccgaga gagggttgtg ggagaacata
gtgtacctag attttagatc tctgtacccc tcaatcatca tcacccacaa cgtctcgccg
gatactctca acagggaagg atgcaaggaa tatgacgttg cccccaggt cggtcaccgc
ttctgcaagg acttcccagg atttatcccg agcctgcttg agacctcct agaggagagg
cagaagataa agaagaagat gaaggccacg attgacccga tcgagaggaa gctcctcgat
tacaggcaga gggccatcaa gatcctggcc aacagctact acggttacta cggctatgca
agggcgcgct ggtactgcaa ggagtgtgca gagagcgtaa cggcctgggg aagggagtac
ataacgatga ccatcagaga gatagaggaa aagtacggct taaggtaat ctacagcgac
accgacggat ttttgccac aatacctgga gcgatgctg aaaccgtcaa aaagaaggcg
atggagttcc tcaagtatat caacgccaaa ctcccgggcg cgcttgagct cgagtacgag
ggcttctaca acgcggctt cttcgtcacg aagaagaagt acgcggtgat agacgaggaa
ggcaagataa caacgcgcgg acttgagatt gtgaggcgcg actggagcga gatagcgaaa
gagacgcagg cgagggttct tgaagctttg ctaaaggacg tgacgtcga aaggccgtg
aggatagtca agaagttac cgaaaagctg agcaagtacg aggttccgcc ggagaagctg
gtgatccacg agcagataac gagggattta aaggactaca aggcaaccgg tccccacgtt
gccgttgcca agaggttggc cgcgagagga gtcaaaatac gccctggaac ggtgataagc
tacatcgtgc tcaagggctc tggaggata ggcgacaggg cgataccgtt cgacgagttc
gaccccgacga agcacaagta cgacgccgag tactacattg agaaccaggt tctccagcc
gttgagagaa ttctgagagc cttcggttac cgcaaggaag acctgcgcta ccagaagacg
agacaggttg gtctgggagc ctggctgaag ccgaagggaa cttga
```

FIG. 3 (cont.)

SEQ ID NO: 2 – polypeptide sequence of DNA polymerase from Thermococcus sp. KS-1

```
Met Ile Leu Asp Thr Asp Tyr Ile Thr Glu Asn Gly Lys Pro Val Ile
Arg Ile Phe Lys Lys Glu Asn Gly Glu Phe Lys Ile Glu Tyr Asp Arg
Thr Phe Glu Pro Tyr Ile Tyr Ala Leu Leu Lys Asp Asp Ser Ala Ile
Glu Glu Val Lys Lys Ile Thr Ala Glu Arg His Gly Thr Val Val Thr
Val Lys Arg Ala Glu Lys Val Gln Lys Lys Phe Leu Gly Arg Pro Val
Glu Val Trp Lys Leu Tyr Phe Thr His Pro Gln Asp Val Pro Ala Ile
Arg Asp Lys Ile Arg Glu His Pro Ala Val Ile Asp Ile Tyr Glu Tyr
Asp Ile Pro Phe Ala Lys Arg Tyr Leu Ile Asp Lys Gly Leu Val Pro
Met Glu Gly Asp Glu Glu Leu Lys Met Leu Ala Phe Asp Ile Glu Thr
Leu Tyr His Glu Gly Glu Glu Phe Ala Glu Gly Pro Ile Leu Met Ile
Ser Tyr Ala Asp Glu Glu Gly Ala Arg Val Ile Thr Trp Lys Asn Ala
Asp Leu Pro Tyr Val Asp Val Val Ser Thr Glu Arg Glu Met Ile Lys
Arg Phe Leu Lys Val Val Lys Glu Lys Asp Pro Asp Val Leu Ile Thr
Tyr Asn Gly Asp Asn Phe Asp Phe Ala Tyr Leu Lys Lys Arg Cys Glu
Lys Leu Gly Ile Asn Phe Thr Leu Gly Arg Asp Gly Ser Glu Pro Lys
Ile Gln Arg Met Gly Asp Arg Phe Ala Val Glu Val Lys Gly Arg Ile
His Phe Asp Leu Tyr Pro Val Ile Arg Arg Thr Ile Asn Leu Pro Thr
Tyr Thr Leu Glu Ala Val Tyr Glu Ala Val Phe Gly Gln Pro Lys Glu
Lys Val Tyr Ala Glu Glu Ile Ala Thr Ala Trp Glu Ser Gly Glu Gly
Leu Glu Arg Val Ala Arg Tyr Ser Met Glu Asp Ala Lys Val Thr Tyr
Glu Leu Gly Lys Glu Phe Phe Pro Met Glu Ala Gln Leu Ser Arg Leu
Ile Gly Gln Ser Leu Trp Asp Val Ser Arg Ser Ser Thr Gly Asn Leu
Val Glu Trp Phe Leu Leu Arg Lys Ala Tyr Glu Arg Asn Glu Leu Ala
Pro Asn Lys Pro Asp Glu Lys Glu Leu Ala Arg Arg Arg Gln Ser Tyr
Glu Gly Gly Tyr Val Lys Glu Pro Glu Arg Gly Leu Trp Glu Asn Ile
Val Tyr Leu Asp Phe Arg Ser Leu Tyr Pro Ser Ile Ile Ile Thr His
Asn Val Ser Pro Asp Thr Leu Asn Arg Glu Gly Cys Lys Glu Tyr Asp
Val Ala Pro Gln Val Gly His Arg Phe Cys Lys Asp Phe Pro Gly Phe
Ile Pro Ser Leu Leu Gly Asp Leu Leu Glu Glu Arg Gln Lys Ile Lys
Lys Lys Met Lys Ala Thr Ile Asp Pro Ile Glu Arg Lys Leu Leu Asp
Tyr Arg Gln Arg Ala Ile Lys Ile Leu Ala Asn Ser Tyr Tyr Gly Tyr
Tyr Gly Tyr Ala Arg Ala Arg Trp Tyr Cys Lys Glu Cys Ala Glu Ser
Val Thr Ala Trp Gly Arg Glu Tyr Ile Thr Met Thr Ile Arg Glu Ile
Glu Glu Lys Tyr Gly Phe Lys Val Ile Tyr Ser Asp Thr Asp Gly Phe
Phe Ala Thr Ile Pro Gly Ala Asp Ala Glu Thr Val Lys Lys Lys Ala
Met Glu Phe Leu Lys Tyr Ile Asn Ala Lys Leu Pro Gly Ala Leu Glu
Leu Glu Tyr Glu Gly Phe Tyr Lys Arg Gly Phe Phe Val Thr Lys Lys
Lys Tyr Ala Val Ile Asp Glu Glu Gly Lys Ile Thr Thr Arg Gly Leu
Glu Ile Val Arg Arg Asp Trp Ser Glu Ile Ala Lys Glu Thr Gln Ala
Arg Val Leu Glu Ala Leu Leu Lys Asp Gly Asp Val Glu Lys Ala Val
Arg Ile Val Lys Glu Val Thr Glu Lys Leu Ser Lys Tyr Glu Val Pro
Pro Glu Lys Leu Val Ile His Glu Gln Ile Thr Arg Asp Leu Lys Asp
Tyr Lys Ala Thr Gly Pro His Val Ala Val Ala Lys Arg Leu Ala Ala
Arg Gly Val Lys Ile Arg Pro Gly Thr Val Ile Ser Tyr Ile Val Leu
Lys Gly Ser Gly Arg Ile Gly Asp Arg Ala Ile Pro Phe Asp Glu Phe
Asp Pro Thr Lys His Lys Tyr Asp Ala Glu Tyr Tyr Ile Glu Asn Gln
Val Leu Pro Ala Val Glu Arg Ile Leu Arg Ala Phe Gly Tyr Arg Lys
Glu Asp Leu Arg Tyr Gln Lys Thr Arg Gln Val Gly Leu Gly Ala Trp
Leu Lys Pro Lys Gly Thr
```

FIG. 3 (cont.)

SEQ ID NO: 3 – nucleic acid sequence of DNA polymerase from Thermococcus celer

```
atgatcctcg acgctgacta catcaccgaa gatgggaagc ccgtcgtgag gatattcagg
aaggagaagg gcgagttcag aatcgactac gacagggact tcgagcccta catctacgcc
ctcctgaagg acgattcggc catcgaggag gtgaagagga taaccgttga gcgccacggg
aaggccgtca gggttaagcg ggtggagaag gtcgaaaaga agttcctcaa caggccgata
gaggtctgga agctctactt caatcacccg caggacgttc cggcgataag ggacgagata
aggaagcatc cggccgtcgt tgatatctac gagtacgaca tccccttcgc caagcgctac
ctcatcgata aggggctcgt cccgatggag ggggaggagg agctcaaact gatggccttc
gacatcgaga ccctctacca cgagggagac gagttcgggg aggggccgat cctgatgata
agctacgccg acggggacgg ggcgagggtc ataacctgga agaagatcga cctcccctac
gtcgacgtcg tctcgaccga gaaggagatg ataaagcgct cctccaggt ggtgaaggag
aaggaccccgg acgtgctcgt aacttacaac ggcgacaact cgacttcgc ctacctgaag
agacgctccg aggagcttgg attgaagttc atcctcggga gggacgggag cgagcccaag
atccagcgca tgggcgaccg cttcgccgtc gaggtgaagg ggaggataca cttcgacctc
taccccggtga taaggcgcac cgtgaacctg ccgacctaca cgctcgaggc ggtctacgag
gccatcttcg ggaggccaaa ggagaaggtc tacgccgggg agatagtgga ggcctgggaa
accggcgagg gtcttgagag ggttgcccgc tactccatgg aggacgcaaa ggttaccttc
gagctcggga gggagttctt cccgatggag gcccagctct cgaggctcat cggccagggt
ctctgggacg tctcccgctc gagcaccggc aacctggtcg agtggttcct cctgaggaag
gcctacgaga ggaacgaact ggccccgaac aagccgagcg gccggaagt ggagatcagg
aggcgtggct acgccggtgg ttacgttaag gagccggaga ggggtttatg ggagaacatc
gtgtacctcg actttcgctc tctttacccc tccatcatca taacccacaa cgtctcgccc
gatacctaa acagggaggg ctgtgagaac tacgacgtcg cccccaggt ggggcataag
ttctgcaaag attttccggg cttcatcccg agcctgctcg gaggcctgct tgaggagagg
cagaagataa agcggaggat gaaggcctct gtggatcccg ttgagcggaa gctcctcgat
tacaggcaga gggccatcaa gatactggcc aacagcttct acggatacta cggctacgcg
agggcgaggt ggtactgcag ggagtgcgcg gagagcgtta ccgcctgggg cagggagtac
atcgataggg tcatcaggga gctcgaggag aagttcggct tcaaggtgct ctacgcggac
acggacggac tgcacgccac gatccccggg gcggacgccg ggaccgtcaa ggagagggcg
aggggggttcc tgagatacat caaccccaag ctccccggcc tcctggagct cgagtacgag
gggttctacc tgaggggttt cttcgtgacg aagaagaagt acgcggtcat agacgaggag
ggcaagataa ccacgcgcgg cctcgagata gtcaggcggg actggagcga ggtggccaag
gagacgcagg cgagggtcct ggaggcgata ctgaggcacg gtgacgtcga ggaggccgtt
agaatcgtca gggaggtaac cgaaaagctg agcaagtacg aggttccgcc ggagaaactg
gtgatccacg agcagataac gagggattg agggactaca agccacggg accgcacgtg
gcggtggcga agcgcctggc cgggaggggg gtaaggatac gccccgggac ggtgataagc
tacatcgtcc tcaagggctc cggaaggata ggggacaggg cgattccctt cgacgagttc
gacccgacta agcacaggta cgacgccgac tactacatcg agaaccaggt tctgccagcc
gtcgagagga tcctgaaggc cttcggctac cgcaaggagg acctgaaata ccagaagacg
aggcaggtgg gcctgggtgc gtggctcaac gcggggaagg ggtga
```

FIG. 3 (cont.)

SEQ ID NO: 4 — polypeptide sequence of DNA polymerase from Thermococcus celer

```
Met Ile Leu Asp Ala Asp Tyr Ile Thr Glu Asp Gly Lys Pro Val Val
Arg Ile Phe Arg Lys Glu Lys Gly Glu Phe Arg Ile Asp Tyr Asp Arg
Asp Phe Glu Pro Tyr Ile Tyr Ala Leu Leu Lys Asp Asp Ser Ala Ile
Glu Glu Val Lys Arg Ile Thr Val Glu Arg His Gly Lys Ala Val Arg
Val Lys Arg Val Glu Lys Val Glu Lys Lys Phe Leu Asn Arg Pro Ile
Glu Val Trp Lys Leu Tyr Phe Asn His Pro Gln Asp Val Pro Ala Ile
Arg Asp Glu Ile Arg Lys His Pro Ala Val Val Asp Ile Tyr Glu Tyr
Asp Ile Pro Phe Ala Lys Arg Tyr Leu Ile Asp Lys Gly Leu Val Pro
Met Glu Gly Glu Glu Glu Leu Lys Leu Met Ala Phe Asp Ile Glu Thr
Leu Tyr His Glu Gly Asp Glu Phe Gly Glu Gly Pro Ile Leu Met Ile
Ser Tyr Ala Asp Gly Asp Gly Ala Arg Val Ile Thr Trp Lys Lys Ile
Asp Leu Pro Tyr Val Asp Val Val Ser Thr Glu Lys Glu Met Ile Lys
Arg Phe Leu Gln Val Val Lys Glu Lys Asp Pro Asp Val Leu Val Thr
Tyr Asn Gly Asp Asn Phe Asp Phe Ala Tyr Leu Lys Arg Arg Ser Glu
Glu Leu Gly Leu Lys Phe Ile Leu Gly Arg Asp Gly Ser Glu Pro Lys
Ile Gln Arg Met Gly Asp Arg Phe Ala Val Glu Val Lys Gly Arg Ile
His Phe Asp Leu Tyr Pro Val Ile Arg Arg Thr Val Asn Leu Pro Thr
Tyr Thr Leu Glu Ala Val Tyr Glu Ala Ile Phe Gly Arg Pro Lys Glu
Lys Val Tyr Ala Gly Glu Ile Val Glu Ala Trp Glu Thr Gly Glu Gly
Leu Glu Arg Val Ala Arg Tyr Ser Met Glu Asp Ala Lys Val Thr Phe
Glu Leu Gly Arg Glu Phe Phe Pro Met Glu Ala Gln Leu Ser Arg Leu
Ile Gly Gln Gly Leu Trp Asp Val Ser Arg Ser Ser Thr Gly Asn Leu
Val Glu Trp Phe Leu Leu Arg Lys Ala Tyr Glu Arg Asn Glu Leu Ala
Pro Asn Lys Pro Ser Gly Arg Glu Val Glu Ile Arg Arg Arg Gly Tyr
Ala Gly Gly Tyr Val Lys Glu Pro Glu Arg Gly Leu Trp Glu Asn Ile
Val Tyr Leu Asp Phe Arg Ser Leu Tyr Pro Ser Ile Ile Ile Thr His
Asn Val Ser Pro Asp Thr Leu Asn Arg Glu Gly Cys Glu Asn Tyr Asp
Val Ala Pro Gln Val Gly His Lys Phe Cys Lys Asp Phe Pro Gly Phe
Ile Pro Ser Leu Leu Gly Gly Leu Leu Glu Glu Arg Gln Lys Ile Lys
Arg Arg Met Lys Ala Ser Val Asp Pro Val Glu Arg Lys Leu Leu Asp
Tyr Arg Gln Arg Ala Ile Lys Ile Leu Ala Asn Ser Phe Tyr Gly Tyr
Tyr Gly Tyr Ala Arg Ala Arg Trp Tyr Cys Arg Glu Cys Ala Glu Ser
Val Thr Ala Trp Gly Arg Glu Tyr Ile Asp Arg Val Ile Arg Glu Leu
Glu Glu Lys Phe Gly Phe Lys Val Leu Tyr Ala Asp Thr Asp Gly Leu
His Ala Thr Ile Pro Gly Ala Asp Ala Gly Thr Val Lys Glu Arg Ala
Arg Gly Phe Leu Arg Tyr Ile Asn Pro Lys Leu Pro Gly Leu Leu Glu
Leu Glu Tyr Glu Gly Phe Tyr Leu Arg Gly Phe Phe Val Thr Lys Lys
Lys Tyr Ala Val Ile Asp Glu Glu Gly Lys Ile Thr Thr Arg Gly Leu
Glu Ile Val Arg Arg Asp Trp Ser Glu Val Ala Lys Glu Thr Gln Ala
Arg Val Leu Glu Ala Ile Leu Arg His Gly Asp Val Glu Glu Ala Val
Arg Ile Val Arg Glu Val Thr Glu Lys Leu Ser Lys Tyr Glu Val Pro
Pro Glu Lys Leu Val Ile His Glu Gln Ile Thr Arg Asp Leu Arg Asp
Tyr Lys Ala Thr Gly Pro His Val Ala Val Ala Lys Arg Leu Ala Gly
Arg Gly Val Arg Ile Arg Pro Gly Thr Val Ile Ser Tyr Ile Val Leu
Lys Gly Ser Gly Arg Ile Gly Asp Arg Ala Ile Pro Phe Asp Glu Phe
Asp Pro Thr Lys His Arg Tyr Asp Ala Asp Tyr Tyr Ile Glu Asn Gln
Val Leu Pro Ala Val Glu Arg Ile Leu Lys Ala Phe Gly Tyr Arg Lys
Glu Asp Leu Lys Tyr Gln Lys Thr Arg Gln Val Gly Leu Gly Ala Trp
Leu Asn Ala Gly Lys Gly
```

FIG. 3 (cont.)

SEQ ID NO: 5 – nucleic acid sequence of DNA polymerase from Thermococcus siculi

```
atgatcctcg acacggacta catcacggaa gatgggaaac ccgtcataag gatattcaag
aaagagaacg gcgagttcaa gatcgagtac gacaggactt ttgaaccctc catctacgcc
ctcctgaagg acgactccgc gattgaggat gttaaaaaga taaccgccga gaggcacgga
acggtggtga aggtcaagcg cgccgaaaag gtgcagaaga agttcctagg caggccggtt
gaagtctgga agctctactt cacccacccc caagatgtcc cggcgataag ggacaagatt
aggaagcatc cagctgtaat tgacatctac gagtacgaca taccattcgc caagcgctac
ctcatcgaca agggcctgat tccgatggag ggtgaagaag agcttaagat gctcgccttc
gacattgaga cgctctacca tgagggtgag gagttcgccg aggggcctat tctgatgata
agctacgccg acgagagcga ggcacgcgtc atcacctgga agaaaatcga cctcccctac
gttgacgtcg tctcaacgga gaaggagatg ataaagcgct tcctccgcgt tgtgaaggag
aaagatcccg atgtcctcat aacctacaac ggcgacaact tgacttcgc ctacctgaag
aagcgctgtg aaaagcttgg aataaacttc ctccttggaa gggacgggag cgagccgaag
atccagagaa tgggtgaccg cttcgccgtt gaggtgaagg ggaggataca cttcgacctc
tatcctgtaa taaggcgcac gataaacctg ccgacctaca tgcttgaggc agtctacgag
gccatctttg ggaagccaaa ggagaaggtt tacgccgagg agatagccac cgcttgggaa
accggagagg gccttgagag ggtggctcgc tactctatgg aggacgcgaa ggtcacgttt
gagcttggaa aggagttctt cccgatggag gcccaacttt cgaggttggt cggccagagc
ttctgggatg tcgcgcgctc aagcacgggc aatctggtcg agtggttcct cctcaggaag
gcctacgaga ggaacgagct ggctccaaac aagccctctg aagggaata tgacgagagg
cgcggtggat acgccggcgg ctacgtcaag gaaccggaaa agggcctgtg ggagaacata
gtctacctcg actataaatc tctctacccc tcaatcatca tcacccacaa cgtctcgccc
gatacccctca accgcgaggg ctgtaaggag tatgacgtag ctccacaggt cggccaccgc
ttctgcaagg actttccagg cttcatcccg agcctgctcg gggatctcct ggaggagagg
cagaagataa agaggaagat gaaggcaaca attgacccga tcgagagaaa gctccttgat
tacaggcaac gggccatcaa gatccttcta aatagtttt acggctacta cggctacgca
agggctcgct ggtactgcaa ggagtgtgcc gagagcgtta cggcatgggg aagggaatat
atcaccatga caatcaggga aatagaagag aagtatgct ttaaagtact ttatgcggac
actgacggct tcttcgcgac gattcccggg gaagatgccg agaccatcaa aaagagggcg
atggagttcc tcaagtacat aaacgccaaa ctccccggtg cgctcgaact tgagtacgag
gacttctaca ggcgcggctt cttcgtcacc aagaagaaat acgcggttat cgacgaggag
ggcaagataa caacgcgcgg gctggagatc gtcaggcgcg actggagcga gatagccaag
gagacgcagg cgcgggttct ggaggccctt ctgaaggacg gtgacgtcga gaggccgtg
agcatagtca aagaagtgac cgagaagctg agcaagtacg aggttcgcc ggagaagctc
gttatccacg agcagataac gcgcgagctg aaggactaca aggcaacggg accacacgtg
gcgatagcga agaggttagc cgcgagaggc gtcaaaatcc gccccgggac agtcatcagc
tacatcgtgc tcaagggctc cgggaggata ggcgacaggg cgattccctt cgacgagttc
gaccccacga agcacaagta cgatgcagag tactacatcg agaaccaggt tctacctgcc
gtcgagagga ttctgaaggc cttcggctat cgcggtgagg agctcagata ccagaagacg
aggcaggttg gacttgggc gtggctgaag ccgaaggga aggggtga
```

FIG. 3 (cont.)

SEQ ID NO: 6 – polypeptide sequence of DNA polymerase from Thermococcus siculi

```
Met Ile Leu Asp Thr Asp Tyr Ile Thr Glu Asp Gly Lys Pro Val Ile
Arg Ile Phe Lys Lys Glu Asn Gly Glu Phe Lys Ile Glu Tyr Asp Arg
Thr Phe Glu Pro Tyr Ile Tyr Ala Leu Leu Lys Asp Asp Ser Ala Ile
Glu Asp Val Lys Lys Ile Thr Ala Glu Arg His Gly Thr Val Val Lys
Val Lys Arg Ala Glu Lys Val Gln Lys Lys Phe Leu Gly Arg Pro Val
Glu Val Trp Lys Leu Tyr Phe Thr His Pro Gln Asp Val Pro Ala Ile
Arg Asp Lys Ile Arg Lys His Pro Ala Val Ile Asp Ile Tyr Glu Tyr
Asp Ile Pro Phe Ala Lys Arg Tyr Leu Ile Asp Lys Gly Leu Ile Pro
Met Glu Gly Glu Glu Glu Leu Lys Met Leu Ala Phe Asp Ile Glu Thr
Leu Tyr His Glu Gly Glu Glu Phe Ala Glu Gly Pro Ile Leu Met Ile
Ser Tyr Ala Asp Glu Ser Glu Ala Arg Val Ile Thr Trp Lys Lys Ile
Asp Leu Pro Tyr Val Asp Val Val Ser Thr Glu Lys Glu Met Ile Lys
Arg Phe Leu Arg Val Val Lys Glu Lys Asp Pro Asp Val Leu Ile Thr
Tyr Asn Gly Asp Asn Phe Asp Phe Ala Tyr Leu Lys Lys Arg Cys Glu
Lys Leu Gly Ile Asn Phe Leu Leu Gly Arg Asp Gly Ser Glu Pro Lys
Ile Gln Arg Met Gly Asp Arg Phe Ala Val Glu Val Lys Gly Arg Ile
His Phe Asp Leu Tyr Pro Val Ile Arg Arg Thr Ile Asn Leu Pro Thr
Tyr Met Leu Glu Ala Val Tyr Glu Ala Ile Phe Gly Lys Pro Lys Glu
Lys Val Tyr Ala Glu Glu Ile Ala Thr Ala Trp Glu Thr Gly Glu Gly
Leu Glu Arg Val Ala Arg Tyr Ser Met Glu Asp Ala Lys Val Thr Phe
Glu Leu Gly Lys Glu Phe Phe Pro Met Glu Ala Gln Leu Ser Arg Leu
Val Gly Gln Ser Phe Trp Asp Val Ala Arg Ser Ser Thr Gly Asn Leu
Val Glu Trp Phe Leu Leu Arg Lys Ala Tyr Glu Arg Asn Glu Leu Ala
Pro Asn Lys Pro Ser Gly Arg Glu Tyr Asp Glu Arg Arg Gly Gly Tyr
Ala Gly Gly Tyr Val Lys Glu Pro Glu Lys Gly Leu Trp Glu Asn Ile
Val Tyr Leu Asp Tyr Lys Ser Leu Tyr Pro Ser Ile Ile Ile Thr His
Asn Val Ser Pro Asp Thr Leu Asn Arg Glu Gly Cys Lys Glu Tyr Asp
Val Ala Pro Gln Val Gly His Arg Phe Cys Lys Asp Phe Pro Gly Phe
Ile Pro Ser Leu Leu Gly Asp Leu Leu Glu Glu Arg Gln Lys Ile Lys
Arg Lys Met Lys Ala Thr Ile Asp Pro Ile Glu Arg Lys Leu Leu Asp
Tyr Arg Gln Arg Ala Ile Lys Ile Leu Leu Asn Ser Phe Tyr Gly Tyr
Tyr Gly Tyr Ala Arg Ala Arg Trp Tyr Cys Lys Glu Cys Ala Glu Ser
Val Thr Ala Trp Gly Arg Glu Tyr Ile Thr Met Thr Ile Arg Glu Ile
Glu Glu Lys Tyr Gly Phe Lys Val Leu Tyr Ala Asp Thr Asp Gly Phe
Phe Ala Thr Ile Pro Gly Asp Ala Glu Thr Ile Lys Lys Arg Ala
Met Glu Phe Leu Lys Tyr Ile Asn Ala Lys Leu Pro Gly Ala Leu Glu
Leu Glu Tyr Glu Asp Phe Tyr Arg Arg Gly Phe Phe Val Thr Lys Lys
Lys Tyr Ala Val Ile Asp Glu Glu Gly Lys Ile Thr Thr Arg Gly Leu
Glu Ile Val Arg Arg Asp Trp Ser Glu Ile Ala Lys Glu Thr Gln Ala
Arg Val Leu Glu Ala Leu Leu Lys Asp Gly Asp Val Glu Glu Ala Val
Ser Ile Val Lys Glu Val Thr Glu Lys Leu Ser Lys Tyr Glu Val Pro
Pro Glu Lys Leu Val Ile His Glu Gln Ile Thr Arg Glu Leu Lys Asp
Tyr Lys Ala Thr Gly Pro His Val Ala Ile Ala Lys Arg Leu Ala Ala
Arg Gly Val Lys Ile Arg Pro Gly Thr Val Ile Ser Tyr Ile Val Leu
Lys Gly Ser Gly Arg Ile Gly Asp Arg Ala Ile Pro Phe Asp Glu Phe
Asp Pro Thr Lys His Lys Tyr Asp Ala Glu Tyr Tyr Ile Glu Asn Gln
Val Leu Pro Ala Val Glu Arg Ile Leu Lys Ala Phe Gly Tyr Arg Gly
Glu Glu Leu Arg Tyr Gln Lys Thr Arg Gln Val Gly Leu Gly Ala Trp
Leu Lys Pro Lys Gly Lys Gly
```

FIG. 3 (cont.)

SEQ ID NO: 7 - polypeptide sequence of DNA polymerase from Thermococcus kodakarensis

```
Met Ile Leu Asp Thr Asp Tyr Ile Thr Glu Asp Gly Lys Pro Val Ile
Arg Ile Phe Lys Lys Glu Asn Gly Glu Phe Lys Ile Glu Tyr Asp Arg
Thr Phe Glu Pro Tyr Phe Tyr Ala Leu Leu Lys Asp Asp Ser Ala Ile
Glu Glu Val Lys Lys Ile Thr Ala Glu Arg His Gly Thr Val Val Thr
Val Lys Arg Val Glu Lys Val Gln Lys Lys Phe Leu Gly Arg Pro Val
Glu Val Trp Lys Leu Tyr Phe Thr His Pro Gln Asp Val Pro Ala Ile
Arg Asp Lys Ile Arg Glu His Pro Ala Val Ile Asp Ile Tyr Glu Tyr
Asp Ile Pro Phe Ala Lys Arg Tyr Leu Ile Asp Lys Gly Leu Val Pro
Met Glu Gly Asp Glu Glu Leu Lys Met Leu Ala Phe Asp Ile Glu Thr
Leu Tyr Glu Glu Gly Glu Glu Phe Ala Glu Gly Pro Ile Leu Met Ile
Ser Tyr Ala Asp Glu Glu Gly Ala Arg Val Ile Thr Trp Lys Asn Val
Asp Leu Pro Tyr Val Asp Val Val Ser Thr Glu Arg Glu Met Ile Lys
Arg Phe Leu Arg Val Val Lys Glu Lys Asp Pro Asp Val Leu Ile Thr
Tyr Asn Gly Asp Asn Phe Asp Phe Ala Tyr Leu Lys Lys Arg Cys Glu
Lys Leu Gly Ile Asn Phe Ala Leu Gly Arg Asp Gly Ser Glu Pro Lys
Ile Gln Arg Met Gly Asp Arg Phe Ala Val Glu Val Lys Gly Arg Ile
His Phe Asp Leu Tyr Pro Val Ile Arg Arg Thr Ile Asn Leu Pro Thr
Tyr Thr Leu Glu Ala Val Tyr Glu Ala Val Phe Gly Gln Pro Lys Glu
Lys Val Tyr Ala Glu Glu Ile Thr Thr Ala Trp Glu Thr Gly Glu Asn
Leu Glu Arg Val Ala Arg Tyr Ser Met Glu Asp Ala Lys Val Thr Tyr
Glu Leu Gly Lys Glu Phe Leu Pro Met Glu Ala Gln Leu Ser Arg Leu
Ile Gly Gln Ser Leu Trp Asp Val Ser Arg Ser Ser Thr Gly Asn Leu
Val Glu Trp Phe Leu Leu Arg Lys Ala Tyr Glu Arg Asn Glu Leu Ala
Pro Asn Lys Pro Asp Glu Lys Glu Leu Ala Arg Arg Arg Gln Ser Tyr
Glu Gly Gly Tyr Val Lys Glu Pro Glu Arg Gly Leu Trp Glu Asn Ile
Val Tyr Leu Asp Phe Arg Ser Leu Tyr Pro Ser Ile Ile Ile Thr His
Asn Val Ser Pro Asp Thr Leu Asn Arg Glu Gly Cys Lys Glu Tyr Asp
Val Ala Pro Gln Val Gly His Arg Phe Cys Lys Asp Phe Pro Gly Phe
Ile Pro Ser Leu Leu Gly Asp Leu Leu Glu Glu Arg Gln Lys Ile Lys
Lys Lys Met Lys Ala Thr Ile Asp Pro Ile Glu Arg Lys Leu Leu Asp
Tyr Arg Gln Arg Ala Ile Lys Ile Leu Ala Asn Ser Tyr Tyr Gly Tyr
Tyr Gly Tyr Ala Arg Ala Arg Trp Tyr Cys Lys Glu Cys Ala Glu Ser
Val Thr Ala Trp Gly Arg Glu Tyr Ile Thr Met Thr Ile Lys Glu Ile
Glu Glu Lys Tyr Gly Phe Lys Val Ile Tyr Ser Asp Thr Asp Gly Phe
Phe Ala Thr Ile Pro Gly Ala Asp Ala Glu Thr Val Lys Lys Lys Ala
Met Glu Phe Leu Lys Tyr Ile Asn Ala Lys Leu Pro Gly Ala Leu Glu
Leu Glu Tyr Glu Gly Phe Tyr Glu Arg Gly Phe Phe Val Thr Lys Lys
Lys Tyr Ala Val Ile Asp Glu Glu Gly Lys Ile Thr Thr Arg Gly Leu
Glu Ile Val Arg Arg Asp Trp Ser Glu Ile Ala Lys Glu Thr Gln Ala
Arg Val Leu Glu Ala Leu Leu Lys Asp Gly Asp Val Glu Lys Ala Val
Arg Ile Val Lys Glu Val Thr Glu Lys Leu Ser Lys Tyr Glu Val Pro
Pro Glu Lys Leu Val Ile His Glu Gln Ile Thr Arg Asp Leu Lys Asp
Tyr Lys Ala Thr Gly Pro His Val Ala Val Ala Lys Arg Leu Ala Ala
Arg Gly Val Lys Ile Arg Pro Gly Thr Val Ile Ser Tyr Ile Val Leu
Lys Gly Ser Gly Arg Ile Gly Asp Arg Ala Ile Pro Phe Asp Glu Phe
Asp Pro Thr Lys His Lys Tyr Asp Ala Glu Tyr Tyr Ile Glu Asn Gln
Val Leu Pro Ala Val Glu Arg Ile Leu Arg Ala Phe Gly Tyr Arg Lys
Glu Asp Leu Arg Tyr Gln Lys Thr Arg Gln Val Gly Leu Ser Ala Trp
Leu Lys Pro Lys Gly Thr
```

FIG. 3 (cont.)

SAMPLE TAG SEQUENCES

| SEQ ID Number | Sample tag sequence |
|---|---|
| 8 | TAGAATTGAAGAA |
| 9 | TGGCCATAGCTAC |
| 10 | GTCATCTGCGACC |
| 11 | TTCGCGCTTGGAC |
| 12 | CGCGAACCGTTAG |
| 13 | TTGCAGCCTCTAA |
| 14 | TCTACTAGTACGA |
| 15 | GTAGGTTCTACTG |
| 16 | GCCAATATCAAGT |
| 17 | CTATCTTGCTGGT |
| 18 | GTTCTCATAGGTA |
| 19 | GTCTATGAACCAA |
| 20 | CGGAGCGCTTATT |
| 21 | TATGCCATGAGGA |
| 22 | ATACGACTCGGAG |
| 23 | GATGGAACTCAGC |
| 24 | GGACCTGCATGAA |
| 25 | TAGACTGGAACTT |
| 26 | GAATTACCTCGTT |
| 27 | AGGATCAGGCTAC |
| 28 | ACGCGTAGAAGAG |
| 29 | CTTCGAGACTTAC |
| 30 | GACGGCTAACTCC |
| 31 | TTAGCATTCTCTT |

FIG. 3 (cont.)

| 32 | GCAAGGCATAGTA |
|---|---|
| 33 | ACCTAGATATGGA |
| 34 | ACGCCAAGGCGTA |
| 35 | TATGACGGATCCG |
| 36 | CCTCCATTAGAGA |
| 37 | ATTGAATACTCTG |
| 38 | GAGATGAGAAGAA |
| 39 | TCTGAGTAGCCGG |
| 40 | AATAGGTAGTACG |
| 41 | GTCGAAGAAGTCC |
| 42 | TACTGCATCTCGT |
| 43 | GACGTATTAGAGC |
| 44 | CCTGCATTATTCG |
| 45 | ACGAATGATGCTC |
| 46 | TACTAGCAGAGAT |
| 47 | CTCCTCATCTTCC |
| 48 | TCCTCTGCGCTGC |
| 49 | CCTTCTCAGTCCG |
| 50 | CAGCTTCATAGCG |
| 51 | TTGACTCTCGCGC |
| 52 | TATCCTGAGCGAT |
| 53 | AACGCCTAGCCGA |
| 54 | CCGAAGACGTCAT |
| 55 | GAGTTCTCCAGAT |
| 56 | TGCATCCGCGCTT |
| 57 | CCTGAACTCAAGT |
| 58 | GGTCGTATGCGTA |

FIG. 3 (cont.)

| 59 | AGGCCTCTCTACC |
|---|---|
| 60 | GTACTCCATCCAA |
| 61 | CAGCGGACGCGCT |
| 62 | ATCTCTCTTAGCA |
| 63 | AAGCAATAATAAT |
| 64 | AAGGCGACTCCGA |
| 65 | ACGTCTCTAGGAG |
| 66 | CCATCAGACCTCT |
| 67 | ACTTAATCGTACT |
| 68 | TGGAATTCTCCAA |
| 69 | CCATACGATCAGG |
| 70 | TTATGGAGCAATA |
| 71 | GCTCGGCGTTCGA |
| 72 | TTGGCCAGTCGCT |
| 73 | CAGATACGTAGAG |
| 74 | AATGCTATTATCC |
| 75 | GCAGCATGCCGAT |
| 76 | GGAGAGTTACCTC |
| 77 | GAGAGTCCATGAT |
| 78 | CAATCTATTCTGA |
| 79 | GCTCTTAGTATCC |
| 80 | CCATAGTTATGGT |
| 81 | TGCGAGATCGAAG |
| 82 | AGAGAAGTCGAGT |
| 83 | GGTAACTCCATAT |
| 84 | TGCTATTCCAGGC |
| 85 | AACCGCGAGGCTC |

FIG. 3 (cont.)

| 86 | TTCTAGAGATACC |
| --- | --- |
| 87 | TTCGCTCAAGTAT |
| 88 | CAGAGAAGGCGCA |
| 89 | TAGAATTGGCCTC |
| 90 | GGCCATTCTCCAG |
| 91 | TCCAACGCGCGTT |
| 92 | GCCGCAGATTACG |
| 93 | GCAGTTCGAACGC |
| 94 | TTCTCTCTGCAGG |
| 95 | TAAGCTACCAGCG |
| 96 | CTGCATGAGGTTG |
| 97 | TTGCCTAGCGAGG |
| 98 | CAACTGAATTAGG |
| 99 | AAGCGGTCCTCTT |
| 100 | AATGGAAGGACCG |
| 101 | GAGTTAGTAAGTT |
| 102 | TTCCTAATTCCAA |
| 103 | GTTCTGGTTCGCT |
| 104 | GTTCATCTCTTCC |
| 105 | ATTCCGAGGAAGA |
| 106 | CTTAGCCGAGAGA |
| 107 | GTCTGCTACGCTT |
| 108 | ATGGCGCCGCGCA |
| 109 | TAATTGGTTATCT |
| 110 | TCGGTTATAAGTC |
| 111 | TGCCTGAGAACGT |
| 112 | AGATGCGGTTAAC |

FIG. 3 (cont.)

| 113 | ATGGAATAGGCGA |
|---|---|
| 114 | AGAGATGCGATCG |
| 115 | CTCCAACTAACGT |
| 116 | GCCTTGCTACTGG |
| 117 | CTTCGTCTCTACG |
| 118 | ACGCTCATAGCCT |
| 119 | GTCGAAGATAAGG |
| 120 | GCCGGAGTCCTCG |
| 121 | TATACGGCGACCT |
| 122 | AGGTAGATATTCG |
| 123 | TTAAGGTACTGCT |
| 124 | CGGATCTGGTATA |
| 125 | GAGGTCTCGGAGG |
| 126 | GGCATCGATGGAC |
| 127 | GATCTCCGATATA |
| 128 | GATTCGGAATACT |
| 129 | CTGCGATCCGGCC |
| 130 | GATCCGGTTGCAA |
| 131 | CGTCAGGCTTGAC |
| 132 | TCGGCAAGGCGAG |
| 133 | GAACGGCGAACGC |
| 134 | CCTCAAGCGGACT |
| 135 | GAAGCCAGATGGT |
| 136 | TGCTCATACCAAT |

METHOD FOR INTRODUCING MUTATIONS

CROSS-REFERENCE TO RELATED APPLICATIONS

This application claims priority to U.S. application Ser. No. 16/971,293, which is a 371 filing of International Application No. PCT/GB2019/050443, filed Feb. 19, 2019, which claims priority to British Application No. 1802744.1, filed Feb. 20, 2018, each of which application is herein incorporated by reference in its entirety.

INCORPORATION OF SEQUENCE LISTING

This application contains a sequence listing submitted electronically via EFS-web, which serves as both the paper copy and the computer readable form (CRF) and consists of a file entitled "SeqListing06172022," which was created on Jun. 17, 2022, which is 61.5 KB in size, and which is herein incorporated by reference in its entirety.

FIELD

This invention relates to a method for introducing mutations into one or more nucleic acid molecule(s), a use of a low bias DNA polymerase in a method for introducing mutations into one or more nucleic acid molecule(s), a group of sample tags, a method for designing the group of sample tags, a computer readable medium and a method for preferentially amplifying target nucleic acid molecules.

BACKGROUND

DNA polymerases can be used to introduce mutations into nucleic acid sequences. This can be useful in multiple applications. For example mutagenesis techniques can be useful in applications including sequencing assisted by mutagenesis (SAM) techniques and for introducing mutations into protein sequences to find mutations that affect the activity of the protein.

Mutations may be introduced using DNA polymerases that have low fidelity. Low fidelity DNA polymerases make mistakes during replication that result in the introduction of mutations. However, many low fidelity DNA polymerases only introduce mutations at a rate of less than 2% per mutation reaction (round of replication), and for some applications higher mutagenesis rates are useful. In addition, low fidelity DNA polymerases may introduce mutations in a biased manner. Such DNA polymerases can be referred to as high bias DNA polymerases.

Mutations may be introduced by replicating sequences, using DNA polymerases, in the presence of nucleotide analogs such as dPTP. DNA polymerases may incorporate the nucleotide analogs in place of a natural nucleotide. Then, in a subsequent cycle of replication, the nucleotide analog can pair with a natural nucleotide that was not present in the original sequence, thereby introducing a mutation. Introducing mutations by replicating sequences in the presence of nucleotide analogs can be used to achieve higher mutations rates.

Commonly used DNA polymerases (such as Taq polymerase) can be used to incorporate nucleotide analogs in place of a natural nucleotide. However, these polymerases are high bias polymerases. High bias DNA polymerases may display two possible biases: mutation bias and template amplification bias.

Some high bias polymerases have high mutation bias, as they do not mutate all four natural nucleotides (adenine, cytosine, guanine and thymine) uniformly at random. For example, high bias DNA polymerases may mutate some nucleotides with a greater frequency than others. Adenine/thymine pairs are connected by two hydrogen bonds, whereas guanine/cytosine pairs are connected by three hydrogen bonds. Thus, it is possible that high bias DNA polymerases are more likely to introduce mutations into adenine/thymine pairs than guanine/cytosine pairs.

High bias polymerases, having high mutation bias, may fail to incorporate nucleotide analogs randomly. For example, high bias polymerases may favour replacing certain bases with nucleotide analogs. DPTP can interconvert between two different tautomeric forms, an imino form and an amino form. The imino tautomer can form Watson-Crick base pairs with adenine, whilst the amino form can form Watson-Crick base pairs with guanine (Kong Thoo Lin P, Brown D M (1989). "*Synthesis and duplex stability of oligonucleotides containing cytosine-thymine analogues*". Nucleic Acids Research. 17: 10373-10383; Stone M J et al. (1991). "*Molecular basis for methoxyamine-initiated mutagenesis: $^1H$ nuclear magnetic resonance studies of base-modified oligodeoxynucleotides*." Journal of Molecular Biology. 222: 711-723; Nedderman A N R et al. (1993). "*Molecular basis for methoxyamine initiated mutagenesis: $^1H$ nuclear magnetic resonance studies of oligonucleotide duplexes containing base-modified cytosine residues*". Journal of Molecular Biology. 230: 1068-1076; Moore M H et al. (1995). "*Direct observation of two base-pairing modes of a cytosine-thymine analogue with guanine in a DNAZ-form duplex. Significance for base analogue mutagenesis*". Journal of Molecular Biology. 251: 665-673). This effectively means that replication in the presence of dPTPs can be used to introduce substitutions in place of adenine, cytosine, guanine or thymine in a nucleotide sequence. However, in aqueous solution, the ratio of the imino to amino forms of dPTP has been shown to be around 10:1 (Harris V H et al. (2003). "*The effect of tautomeric constant on the specificity of nucleotide incorporation during DNA replication: support for the rare tautomer hypothesis of substitution mutagenesis*". Journal of Molecular Biology. 326: 1389-1401). Accordingly, when a polymerase such as Taq polymerase is used to introduce mutations using dPTP, it introduces substitutions of adenine and thymine much more frequently than substitutions of guanine and cytosine (Zaccolo M et al. (1996). "*An approach to random mutagenesis of DNA using mixtures of triphosphate derivatives of nucleoside analogues*". Journal of Molecular Biology. 255: 589-603; Harris V H et al. (2003). "*The effect of tautomeric constant on the specificity of nucleotide incorporation during DNA replication: support for the rare tautomer hypothesis of substitution mutagenesis*". Journal of Molecular Biology. 326: 1389-1401).

Secondly, high bias polymerases may demonstrate template amplification bias, i.e. they may replicate some template nucleic acid molecules with a higher success rate per PCR cycle than others. Over many cycles of PCR this bias can create extreme differences in copy number amongst templates. Regions of a template nucleic acid molecule may form secondary structures or may contain a higher proportion of some nucleotides (for example guanine or cytosine nucleotides) than others. A high bias polymerase may be more effective to amplify, for example, guanine and cytosine rich template nucleic acid molecules compared to adenine and thymine rich template nucleic acid molecules, or may be more effective to amplify template nucleic acid molecules that do not form secondary structures.

Many of the applications of mutagenesis are more effective if mutagenesis can be performed with low bias (both mutation bias and template amplification).

The accurate assembly of genome sequences has proven difficult as many second generation sequencing platforms are only capable of sequencing short nucleic acid fragments, and require the target nucleic acid sequences to be amplified during the sequencing process in order to provide sufficient nucleic acid molecules for the sequencing step. If the user desires to sequence a larger nucleic acid sequence, this can be achieved by sequencing regions of the target nucleic acid molecules. The user must then computationally assemble the sequence of the full nucleic acid sequence from the sequences of the regions.

Assembling a nucleic acid sequence using sequences of regions can be difficult. In particular, where long regions of the sequences are very similar to one another it may be difficult to determine whether sequences of two regions are both sequences of replicates of the same original template nucleic acid molecule or correspond to sequences from two different original template nucleic acid molecules. Similarly, it may be difficult to determine whether sequences of two regions correspond to sequences of replicates of the same portion of a template nucleic acid molecule, or actually correspond to two different repeats within the template nucleic acid molecule. These difficulties can be circumvented by introducing mutations into the target nucleic acid molecules prior to amplification. The user may then identify that fragments having the same mutation patterns are likely to have originated from the same portion of the same original template nucleic acid molecule. This type of sequencing method is sometimes referred to as sequencing aided by mutagenesis (SAM).

SUMMARY

The sequencing methods described above are more effective when the mutations that are introduced into the target nucleic acid molecules are uniformly random. If the mutations are uniformly random, then the likelihood, for example, that any given portion of a template nucleic acid molecule would have a unique mutation pattern is higher. Thus, there is a need for the identification of DNA polymerases that are able to introduce mutations uniformly at random (have low mutation bias).

In addition, sequencing methods using DNA polymerases having high template amplification bias may be limited. DNA polymerases having high template amplification bias will replicate and/or mutate some target nucleic acid molecules better than others, and so a sequencing method that uses such a high bias DNA polymerase may not be able to sequence some target nucleic acid molecules well.

The present inventors have identified polymerases that are low bias polymerases (have both low template amplification bias and low mutation bias), and so are particularly useful in a method for introducing mutations into at least one target nucleic acid molecule.

The user may wish to use the methods of the invention on more than one sample at once. In such cases, it would be advantageous for the user to be able to identify which target nucleic acid molecule came from which original sample. Such identification could be achieved by labelling the target nucleic acid molecules with sample tags. However, the sample tags may, themselves, be mutated during the method and so the present inventors have determined how to design sample tags that can be distinguished from one another even if they are mutated.

The user may also wish to ensure that the methods of the invention are used to mutate and amplify long target nucleic acid molecules in preference compared to short nucleic acid molecules. The present inventors have found that this can be achieved by introducing special primer binding sites into each end of the target nucleic acid molecules.

Thus, in a first aspect of the invention, there is provided a method for introducing mutations into at least one target nucleic acid molecule comprising:
  a. providing at least one sample comprising at least one target nucleic acid molecule; and
  b. amplifying the at least one target nucleic acid molecule using a low bias DNA polymerase.

In a second aspect of the invention, there is provided a use of a low bias DNA polymerase in a method for introducing mutations into at least one target nucleic acid molecule.

In a third aspect of the invention, there is provided a method for determining a sequence of at least one target nucleic acid molecule comprising the method for introducing mutations of the invention.

In a fourth aspect of the invention, there is provided a method for engineering a protein comprising the method for introducing mutations of the invention.

In a fifth aspect of the invention, there is provided a group of sample tags, wherein each sample tag differs from substantially all other sample tags in the group by at least one low probability mutation difference or at least three high probability mutation differences.

In a sixth aspect of the invention, there is provided a method for designing a group of sample tags suitable for use in a method for introducing mutations into at least one target nucleic acid molecule comprising:
  a. analysing the method for introducing mutations into at least one target nucleic acid molecule and determining the average number of low probability mutations that take place during the method for introducing mutations into at least one target nucleic acid molecule; and
  b. determining sequences for a group of sample tags wherein each sample tag differs from substantially all sample tags in the group by more low probability differences than the average number of low probability mutations that take place during the method for introducing mutations into at least one target nucleic acid molecule.

In a seventh aspect of the invention, there is provided a method for introducing mutations into at least one target nucleic acid molecule comprising:
  a. providing at least one sample comprising at least one target nucleic acid molecule; and
  b. introducing mutations into the at least one target nucleic acid molecule by amplifying the at least one target nucleic acid molecule using a DNA polymerase to provide a mutated at least one target nucleic acid molecule,
wherein step b. is carried out using dNTPs at unequal concentrations.

In an eighth aspect of the invention, there is provided a group of sample tags obtainable by the method for designing a group of sample tags of the invention.

In a ninth aspect of the invention, there is provided a computer readable medium configured to perform the method for designing a group of sample tags of the invention.

In a tenth aspect of the invention, there is provided a method for preferentially amplifying target nucleic acid molecules that are larger than 1 kbp in length comprising:
  a. providing at least one sample comprising target nucleic acid molecules;
  b. introducing a first adapter at the 3' end of target nucleic acid molecules and a second adapter at the 5' end of target nucleic acid molecules; and
  c. amplifying the target nucleic acid molecules using primers that are complementary to a portion of the first adapter,
wherein the first adapter and the second adapter can anneal to one another.

BRIEF DESCRIPTION OF THE DRAWINGS

FIG. 3 is a sequence listing.

DETAILED DESCRIPTION OF THE PREFERRED EMBODIMENT

General Definitions

Figure 1:
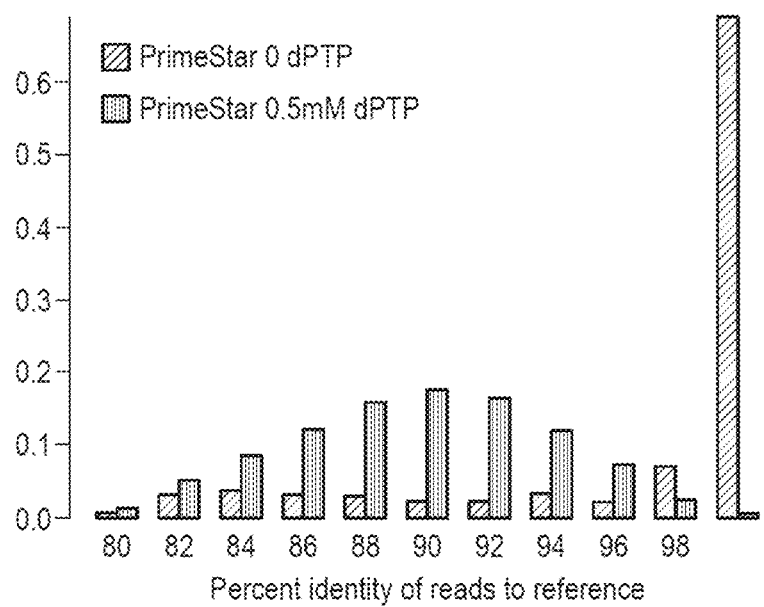
FIG. 1 shows the level of mutation achieved with three different polymerases in the presence or absence of dPTP. Panel A shows data obtained using Taq (Jena Biosciences), panel B shows data obtained using LongAmp (New England Biolabs) and panel C shows data using Primestar GXL (Takara). The dark grey bars show the results obtained in the absence of dPTP and the pale grey bars show the results obtained in the presence of 0.5 mM dPTP.

Unless defined otherwise, technical and scientific terms used herein have the same meaning as commonly understood by a person skilled in the art to which this invention belongs.

In general, the term "comprising" is intended to mean including, but not limited to. For example, the phrase "a method for introducing mutations into at least one target nucleic acid molecule comprising" certain steps should be interpreted to mean that the method includes the recited steps, but that additional steps may be performed.

In some embodiments of the invention, the word "comprising" is replaced with the phrase "consisting of". The term "consisting of" is intended to be limiting. For example, the phrase "a method for introducing mutations into at least one target nucleic acid molecule consisting of" certain steps should be understood to mean that the method includes the recited steps, and that no additional steps are performed.

For the purpose of this invention, in order to determine the percent identity of two sequences (such as two polynucleotide sequences), the sequences are aligned for optimal comparison purposes (e.g., gaps can be introduced in a first sequence for optimal alignment with a second sequence). The nucleotide or amino acid residues at each of the positions are then compared. When a position in the first sequence is occupied by the same residue as the corresponding position in the second sequence, then the residues are identical at that position. The percent identity between the two sequences is a function of the number of identical positions shared by the sequences (i.e., % identity=number of identical positions/total number of positions×100). Typically the sequence comparison is carried out over the length of the reference sequence. For example, to assess whether a test sequence is at least 95% identical to SEQ ID NO. 2 (the reference sequence), the skilled person would carry out an alignment over the length of SEQ ID NO. 2, and identify how many positions in the test sequence were identical to those of SEQ ID NO. 2. If at least 80% of the positions are identical, the test sequence is at least 80% identical to SEQ ID NO. 2. If the sequence is shorter than SEQ ID NO. 2, the gaps should be considered to be non-identical positions.

The skilled person is aware of different computer programs that are available to determine the homology or identity between two sequences. For instance, a comparison of sequences and determination of percent identity between two sequences can be accomplished using a mathematical algorithm. In an embodiment, the percent identity between two amino acid or nucleic acid sequences is determined using the Needleman and Wunsch (1970) algorithm which has been incorporated into the GAP program in the Accelrys GCG software package (available at http://www.accelrys-.com/products/gcg/), using either a Blosum 62 matrix or a PAM250 matrix, and a gap weight of 16, 14, 12, 10, 8, 6, or 4 and a length weight of 1, 2, 3, 4, 5, or 6.

A Method for Introducing Mutations into at Least One Target Nucleic Acid Molecule In one aspect, the invention provides a method for introducing mutations into at least one target nucleic acid molecule. In a further aspect, the invention provides a use of a low bias DNA polymerase in a method for introducing mutations into at least one target nucleic acid molecule.

The mutations may be substitution mutations, insertion mutations or deletion mutations. For the purposes of the present invention, the term "substitution mutation" should be interpreted to mean that a nucleotide is replaced with a different nucleotide. For example, the conversion of the sequence ATCC to the sequence AGCC is a substitution mutation. For the purposes of the present invention, the term "insertion mutation" should be interpreted to mean that at least one nucleotide is added to a sequence. For example, conversion of the sequence ATCC to the sequence ATTCC is an example of an insertion mutation (with an additional T nucleotide being inserted). For the purposes of the present invention, the term "deletion mutation" should be interpreted to mean that at least one nucleotide is removed from a sequence. For example, conversion of the sequence ATTCC to ATCC is an example of a deletion mutation (with a T nucleotide being removed). Preferably the mutations are substitution mutations.

For the purposes of the present invention, a "nucleic acid molecule" refers to a polymeric form of nucleotides of any length. The nucleotides may be deoxyribonucleotides, ribonucleotides or analogs thereof. Preferably, the target nucleic acid molecule is made up of deoxyribonucleotides or ribonucleotides. Even more preferably, the target nucleic acid molecule is made up of deoxyribonucleotides, i.e. the target nucleic acid molecule is a DNA molecule.

The at least one "target nucleic acid molecule" can be any nucleic acid molecule into which the user of the method would like to introduce mutations. The target nucleic acid molecule may form part of a larger nucleic acid molecule such as a chromosome. The target nucleic acid molecule may comprise a gene, multiple genes or a fragment of a gene. The target nucleic acid molecule may be greater than 1 kbp, greater than 1.5 kbp, greater than 2 kbp, greater than 4 kbp, greater than 5 kbp, greater than 7 kbp, greater than 8 kbp, between 1 kbp and 50 kbp, or between 1 kbp and 20 kbp in size.

The term "at least one target nucleic acid molecule" is considered to be interchangeable with the term "at least one target nucleic acid molecules".

The "at least one target nucleic acid molecule" can be single stranded, or may be part of a double stranded complex. For example, if the at least one target nucleic acid molecule is made up of deoxyribonucleotides, it may form part of a double stranded DNA complex. In which case, one strand (for example the coding strand) will be considered to be the at least one target nucleic acid molecule, and the other strand is a nucleic acid molecule that is complementary to the at least one target nucleic acid molecule.

The method for introducing mutations into at least one target nucleic acid molecule may comprise:
  a. providing at least one sample comprising at least one target nucleic acid molecule; and
  b. amplifying the at least one target nucleic acid molecule using a low bias DNA polymerase.

Providing at Least One Sample Comprising at Least One Target Nucleic Acid Molecule The method for introducing mutations into at least one target nucleic acid molecule may comprise a step of providing at least one sample comprising at least one target nucleic acid molecule.

The at least one sample may comprise any sample that comprises at least one target nucleic acid molecule. The at least one sample may be obtained from any source. For example, the at least one sample may comprise a sample of nucleic acids derived from a human, for example a sample extracted from a skin swab of a human patient. Alternatively, the at least one sample may be derived from other sources such as a sample from a water supply. Such a sample could contain billions of template nucleic acid molecules. It would be possible to mutate each of these billions of target nucleic acid molecules simultaneously using the methods of the invention, and so there is no upper limit on the number of target nucleic acid molecules which could be used in the methods of the invention.

In an embodiment, step a. comprises providing more than one sample. For example, step a. may comprise providing 2, 3, 4, 5, 6, 7, 8, 9, 10, 11, 15, 20, 25, 50, 75, or 100 samples. Optionally, step a. comprises providing less than 2000, less than 1000, less than 750, or less than 500 samples. In a further embodiment, step a. comprises providing between 2 and 100, between 2 and 75, between 2 and 50, between 2 and 25, between 5 and 15, or between 7 and 15 samples.

Amplifying the at Least One Target Nucleic Acid Molecule Using a Low Bias DNA Polymerase The methods of the invention may comprise amplifying the at least one target nucleic acid molecule using a low bias DNA polymerase.

Amplifying the at least one target nucleic acid molecule refers to replicating the at least one target nucleic acid molecule to provide at least one nucleic acid molecule that is complementary to the at least one target nucleic acid molecule and/or replicates of the at least one target nucleic acid molecule. Amplifying the at least one target nucleic acid molecule using a low bias DNA polymerase, increases the number of replicates of the at least one target nucleic acid molecule, and introduces mutations into the at least one target nucleic acid molecule. Since mutations are introduced, the replicates are not necessarily identical to the original at least one target nucleic acid molecule. The original at least one target nucleic acid molecule and the replicates of the at least one target nucleic acid molecule may be referred to collectively as "at least one mutated target nucleic acid molecule".

For example, amplifying the at least one target nucleic acid molecule using a low bias DNA polymerase may comprise incubating the sample comprising the at least one target nucleic acid molecule with the low bias DNA polymerase and suitable primers under conditions suitable for the low bias DNA polymerase to catalyse the generation of replicates of the at least one target nucleic acid molecule.

Suitable primers comprise short nucleic acid molecules complementary to regions flanking the at least one target nucleic acid molecules or to regions flanking nucleic acid molecules that are complementary to the at least one target nucleic acid molecule. For example, if the target nucleic acid molecule is part of a chromosome, the primers may be complementary to regions of the chromosome immediately 3' to the 3' end of the target nucleic acid molecule and nucleic acid molecules complementary to regions immediately 5' to the 5' end of the target nucleic acid molecule, or the primers will be complementary to regions of the chromosome immediately 3' to the 3' end of a nucleic acid molecule complementary to the target nucleic acid molecule and nucleic acid molecules complementary to regions immediately 5' to the 5' end of a nucleic acid molecule complementary to the target nucleic acid molecule. Alternatively, the user may introduce primer binding sites (short nucleic acid sequences) into regions flanking the at least one target nucleic acid molecules. This is described in more detail in the section entitled "barcodes, samples and adapters".

Suitable conditions include a temperature at which the low bias DNA polymerase can catalyse the generation of replicates of the at least one target nucleic acid molecule. For example, a temperature of between 40° C. and 90° C., between 50° C. and 80° C., between 60° C. and 70° C., or around 68° C. may be used.

The step of amplifying the at least one target nucleic acid molecule may comprise multiple rounds of replication. For example, the step of amplifying the at least one target nucleic acid molecule preferably comprises:
  i) a round of replicating the at least one target nucleic acid molecule to provide at least one nucleic acid molecule that is complementary to the at least one target nucleic acid molecule; and
  ii) a round of replicating the at least one target nucleic acid molecule to provide replicates of the at least one target nucleic acid molecule.

Optionally, the step of amplifying the at least one target nucleic acid molecule comprises at least 2, at least 4, at least 6, at least 8, or at least 10 rounds of replicating the at least one target nucleic acid molecule. Some of these rounds of replicating the at least one target nucleic acid molecule may take place in the presence of nucleotide analogs. Optionally, the step of amplifying the at least one target nucleic acid molecule comprises at least 1, at least 2, at least 3, at least 4, at least 5, or at least 6 rounds of replication at a temperature between 60° C. and 80° C.

Optionally, the step of amplifying the at least one target nucleic acid molecule is carried out using the polymerase chain reaction (PCR). PCR is a process that involves multiple rounds of the following steps for replicating a nucleic acid molecule:
a) melting;
b) annealing;
c) extension; and
d) elongation.

The nucleic acid molecule (such as the at least one target nucleic acid molecule) is mixed with suitable primers and a polymerase, such as a low bias DNA polymerase of the invention. In the melting step, the nucleic acid molecule is heated to a temperature above 90° C. such that a double-stranded nucleic acid molecule will denature (separate into two strands). In the annealing step, the nucleic acid molecule is cooled to a temperature below 75° C., for example between 55° C. and 70° C., around 55° C., or around 68° C. to allow the primers to anneal to the nucleic acid molecule. In the extension step, the nucleic acid molecule is heated to a temperature greater than 60° C. to allow the DNA polymerase to catalyse primer extension, the addition of nucleotides complementary to the template strand. In the elongation step, the nucleic acid molecule is heated to a temperature at which the DNA polymerase has high activity, such as a temperature between 60° C. and 70° C., to catalyse addition of further complementary nucleic acids in order to complete the new nucleic acid strand.

Optionally, the method of the invention comprises multiple rounds of PCR using the low bias DNA polymerase.

The Low Bias DNA Polymerase

The methods of the invention may comprise a step of amplifying the at least one target nucleic acid molecule using a low bias DNA polymerase.

According to the present invention, a "low bias DNA polymerase" is a DNA polymerase that (a) exhibits low mutation bias, and/or (b) exhibits low template amplification bias.

Low Mutation Bias

A low bias DNA polymerase that exhibits low mutation bias is a DNA polymerase that is able to mutate adenine and thymine, adenine and guanine, adenine and cytosine, thymine and guanine, thymine and cytosine, or guanine and cytosine at similar rates. In an embodiment, the low bias DNA polymerase is able to mutate adenine, thymine, guanine, and cytosine at similar rates.

Optionally, the low bias DNA polymerase is able to mutate adenine and thymine, adenine and guanine, adenine and cytosine, thymine and guanine, thymine and cytosine, or guanine and cytosine at a rate ratio of 0.5-1.5:0.5-1.5, 0.6-1.4:0.6-1.4, 0.7-1.3:0.7-1.3, 0.8-1.2:0.8-1.2, or around 1:1 respectively. Preferably, the low bias DNA polymerase is able to mutate guanine and adenine at a rate ratio of 0.5-1.5:0.5-1.5, 0.6-1.4:0.6-1.4, 0.7-1.3:0.7-1.3, 0.8-1.2:0.8-1.2, or around 1:1 respectively. Preferably, the low bias DNA polymerase is able to mutate thymine and cytosine at a rate ratio of 0.5-1.5:0.5-1.5, 0.6-1.4:0.6-1.4, 0.7-1.3:0.7-1.3, 0.8-1.2:0.8-1.2, or around 1:1 respectively.

In such embodiments, in a step of amplifying the at least one target nucleic acid molecule using a low bias DNA polymerase, the DNA polymerase mutates adenine and thymine, adenine and guanine, adenine and cytosine, thymine and guanine, thymine and cytosine, or guanine and cytosine nucleotides in the at least one target nucleic acid molecule at a rate ratio of 0.5-1.5:0.5-1.5, 0.6-1.4:0.6-1.4, 0.7-1.3:0.7-1.3, 0.8-1.2:0.8-1.2, or around 1:1 respectively. Preferably, the low bias DNA polymerase mutates guanine and adenine nucleotides in the at least one target nucleic acid molecule at a rate ratio of 0.5-1.5:0.5-1.5, 0.6-1.4:0.6-1.4, 0.7-1.3:0.7-1.3, 0.8-1.2:0.8-1.2, or around 1:1 respectively. Preferably, the low bias DNA polymerase mutates thymine and cytosine nucleotides in the at least one target nucleic acid molecule at a rate ratio of 0.5-1.5:0.5-1.5, 0.6-1.4:0.6-1.4, 0.7-1.3:0.7-1.3, 0.8-1.2:0.8-1.2, or around 1:1 respectively.

Optionally, the low bias DNA polymerase is able to mutate adenine, thymine, guanine, and cytosine at a rate ratio of 0.5-1.5:0.5-1.5:0.5-1.5:0.5-1.5, 0.6-1.4:0.6-1.4:0.6-1.4:0.6-1.4, 0.7-1.3:0.7-1.3:0.7-1.3:0.7-1.3, 0.8-1.2:0.8-1.2:0.8-1.2:0.8-1.2, or around 1:1:1:1 respectively. Preferably, the low bias DNA polymerase is able to mutate adenine, thymine, guanine and cytosine at a rate ratio of 0.7-1.3:0.7-1.3:0.7-1.3:0.7-1.3.

In such embodiments, in a step of amplifying the at least one target nucleic acid molecule using a low bias DNA polymerase, the DNA polymerase may mutate adenine, thymine, guanine, and cytosine nucleotides in the at least one target nucleic acid molecule at a rate ratio of 0.5-1.5:0.5-1.5:0.5-1.5:0.5-1.5, 0.6-1.4:0.6-1.4:0.6-1.4:0.6-1.4, 0.7-1.3:0.7-1.3:0.7-1.3:0.7-1.3, 0.8-1.2:0.8-1.2:0.8-1.2:0.8-1.2, or around 1:1:1:1 respectively. Preferably, the low bias DNA polymerase mutates adenine, thymine, guanine, and cytosine nucleotides in the at least one target nucleic acid molecule at a rate ratio of 0.7-1.3:0.7-1.3:0.7-1.3:0.7-1.3.

The adenine, thymine, cytosine, and/or guanine may be substituted with another nucleotide. For example, if the low bias DNA polymerase is able to mutate adenine, amplifying the at least one target nucleic acid molecule in the presence of the low bias DNA polymerase may substitute at least one adenine nucleotide in the nucleic acid molecule with thymine, guanine, or cytosine. Similarly, if the low bias DNA polymerase is able to mutate thymine, amplifying the at least one target nucleic acid molecule in the presence of the low bias DNA polymerase may substitute at least one thymine nucleotide with adenine, guanine, or cytosine. If the low bias DNA polymerase is able to mutate guanine, amplifying the at least one target nucleotide in the presence of the low bias DNA polymerase may substitute at least one guanine nucleotide with thymine, adenine, or cytosine. If the low bias DNA polymerase is able to mutate cytosine, amplifying the at least one target nucleotide in the presence of the low bias DNA polymerase may substitute at least one cytosine nucleotide with thymine, guanine, or adenine.

The low bias DNA polymerase may not be able to substitute a nucleotide directly, but it may still be able to mutate that nucleotide by replacing the corresponding nucleotide on the complementary strand. For example, if the target nucleic acid molecule comprises thymine, there will be an adenine nucleotide present in the corresponding position of the at least one nucleic acid molecule that is complementary to the at least one target nucleic acid molecule. The low bias DNA polymerase may be able to replace the adenine nucleotide of the at least one nucleic acid molecule that is complementary to the at least one target nucleic acid molecule with a guanine and so, when the at least one nucleic acid molecule that is complementary to the at least one target nucleic acid molecule is replicated, this will result in a cytosine being present in the corresponding replicated at least one target nucleic acid molecule where there was originally a thymine (a thymine to cytosine substitution).

In an embodiment, the low bias DNA polymerase mutates between 1% and 15%, between 2% and 10%, or around 8% of the nucleotides in the at least one target nucleic acid. In such embodiments, the step of amplifying the at least one target nucleic acid molecule using a low bias DNA polymerase is carried out in such a way that between 1% and 15%, between 2% and 10%, or around 8% of the nucleotides in the at least one target nucleic acid are mutated. For example, if the user wishes to mutate around 8% of the nucleotides in the target nucleic acid molecule, and the low bias DNA polymerase mutates around 1% of the nucleotides per round of replication, the step of amplifying the at least one target nucleic acid molecule using a low bias DNA polymerase may comprise 8 rounds of replication.

In an embodiment, the low bias DNA polymerase is able to mutate between 0% and 3%, between 0% and 2%, between 0.1% and 5%, between 0.2% and 3%, or around 1.5% of the nucleotides in the at least one target nucleic acid molecule per round of replication. In an embodiment, the low bias DNA polymerase mutates between 0% and 3%, between 0% and 2%, between 0.1% and 5%, between 0.2% and 3%, or around 1.5% of the nucleotides in the at least one target nucleic acid molecule per round of replication. The actual amount of mutation that takes place each round may vary, but may average to between 0% and 3%, between 0% and 2%, between 0.1% and 5%, between 0.2% and 3%, or around 1.5%.

Whether a DNA Polymerase is Able to Mutate a Nucleotide and, if so, at What Rate Whether the low bias DNA polymerase is able to mutate a certain percentage of the nucleotides in the at least one target nucleic acid molecule per round of replication can be determined by amplifying a nucleic acid molecule of known sequence in the presence of the low bias DNA polymerase for a set number of rounds of replication. The resulting amplified nucleic acid molecule can then be sequenced, and the percentage of nucleotides that are mutated per round of replication calculated. For example, the nucleic acid molecule of known sequence can be amplified using 10 rounds of PCR in the presence of the low bias DNA polymerase. The resulting nucleic acid molecule can then be sequenced. If the resulting nucleic acid molecule comprises 10% nucleotides that are different in corresponding nucleotides in the original known sequence, then the user would understand that the low bias DNA polymerase is able to mutate 1% of the nucleotides in the at least one target nucleic acid molecule on average per round of replication. Similarly, to see whether the low bias DNA polymerase mutates a certain percentage of the nucleotides in the at least one target nucleic acid molecule in a given method, the user could perform the method on a nucleic acid molecule of known sequence and use sequencing to determine the percentage of nucleotides that are mutated once the method is completed.

The low bias DNA polymerase is able to mutate a nucleotide such as adenine, if, when used to amplify a nucleic acid molecule, it provides a nucleic acid molecule in which some instances of that nucleotide are substituted or deleted. Preferably, the term "mutate" refers to introduction of substitution mutations, and in some embodiments the term "mutate" can be replaced with "introduces substitutions of".

The low bias DNA polymerase mutates a nucleotide such as adenine in at least one target nucleic acid molecule in the method of the invention if, when the step of amplifying the at least one target nucleic acid molecule using a low bias DNA polymerase is carried out, this step results in a mutated at least one target nucleic acid molecule in which some instances of that nucleotide are mutated. For example, if the low bias DNA polymerase mutates adenine in the at least one target nucleic acid molecule, when the step of amplifying the at least one target nucleic acid molecule using a low bias DNA polymerase is carried out, this step results in a mutated at least one target nucleic acid molecule in which at least one adenine has been substituted or deleted.

To determine whether a DNA polymerase is able to introduce certain mutations, the skilled person merely needs to test the DNA polymerase using a nucleic acid molecule of known sequence. A suitable nucleic acid molecule of known sequence is a fragment from a bacterial genome of known sequence, such as E. coli MG1655. The skilled person could amplify the nucleic acid molecule of known sequence using PCR in the presence of the low bias DNA polymerase. The skilled person could then sequence the amplified nucleic acid molecule and determine whether its sequence is the same as the original known sequence. If not, the skilled person could determine the nature of the mutations. For example, if the skilled person wished to determine whether a DNA polymerase is able to mutate adenine using a nucleotide analog, the skilled person could amplify the nucleic acid molecule of known sequence using PCR in the presence of the nucleotide analog, and sequence the resulting amplified nucleic acid molecule. If the amplified DNA has mutations in positions corresponding to adenine nucleotides in the known sequence, then the skilled person would know that the DNA polymerase could mutate adenine using a nucleotide analog.

Rate ratios can be calculated in a similar manner. For example, if the skilled person wishes to determine the rate ratio at which guanine and cytosine nucleotides are mutated, the skilled person could amplify a nucleic acid molecule having a known sequence using PCR in the presence of the low bias DNA polymerase. The skilled person could then sequence the resulting amplified nucleic acid molecule and identify how many of the guanine nucleotides have been substituted or deleted and how many of the cytosine nucleotides have been substituted or deleted. The rate ratio is the ratio of the number of guanine nucleotides that have been substituted or deleted to the number of cytosine nucleotides that have been substituted or deleted. For example, if 16 guanine nucleotides have been replaced or deleted and 8 cytosine nucleotides have been replaced or deleted, the guanine and cytosine nucleotides have been mutated at a rate ratio of 16:8 or 2:1 respectively.

Using Nucleotide Analogs

The low bias DNA polymerase may not be able to replace nucleotides with other nucleotides directly (at least not with high frequency), but the low bias DNA polymerase may still be able to mutate a nucleic acid molecule using a nucleotide analog. The low bias DNA polymerase may be able to replace nucleotides with other natural nucleotides (i.e. cytosine, guanine, adenine or thymine) or with nucleotide analogs.

For example, the low bias DNA polymerase may be a high fidelity DNA polymerase. High fidelity DNA polymerases tend to introduce very few mutations in general, as they are highly accurate. However, the present inventors have found that some high fidelity DNA polymerases may still be able to mutate a target nucleic acid molecule, as they may be able to introduce nucleotide analogs into a target nucleic acid molecule.

In an embodiment, in the absence of nucleotide analogs, the high fidelity DNA polymerase introduces less than 0.01%, less than 0.0015%, less than 0.001%, between 0% and 0.0015%, or between 0% and 0.001% mutations per round of replication.

In an embodiment, the low bias DNA polymerase is able to incorporate nucleotide analogs into the at least one target nucleic acid molecule. In an embodiment, the low bias DNA polymerase incorporates nucleotide analogs into the at least one target nucleic acid molecule. In an embodiment, the low bias DNA polymerase can mutate adenine, thymine, guanine, and/or cytosine using a nucleotide analog. In an embodiment, the low bias DNA polymerase mutates adenine, thymine, guanine, and/or cytosine in the at least one target nucleic acid molecule using a nucleotide analog. In an embodiment, the DNA polymerase replaces guanine, cytosine, adenine and/or thymine with a nucleotide analog. In an embodiment, the DNA polymerase can replace guanine, cytosine, adenine and/or thymine with a nucleotide analog.

Figure 6:
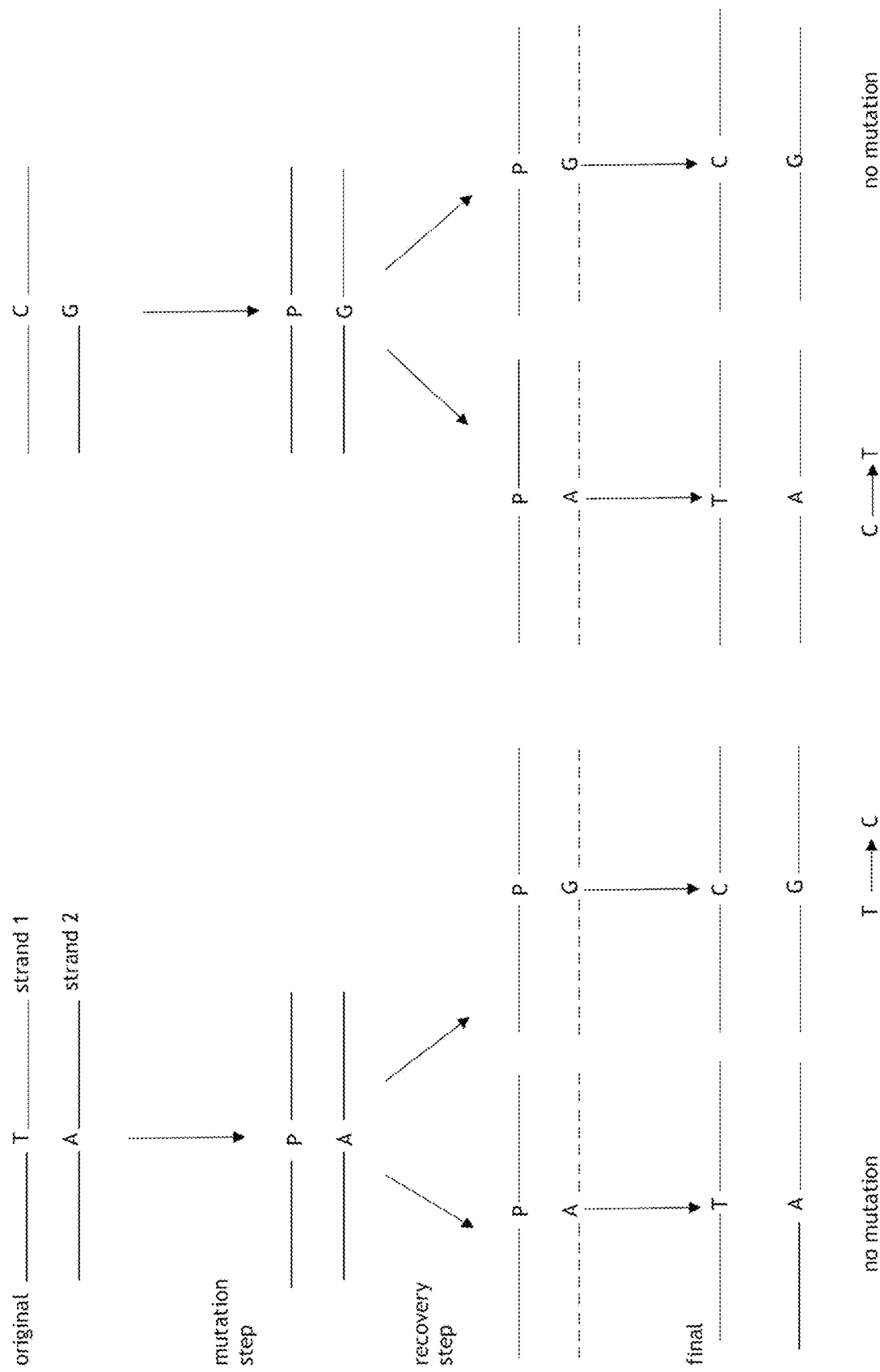
FIG. 6 provides a pictorial representation of mutation using the nucleotide analog dPTP (referred to as "P" in FIG. 6).

Incorporating nucleotide analogs into the at least one target nucleic acid molecule can be used to mutate nucleotides, as they may be incorporated in place of existing nucleotides and they may pair with nucleotides in the opposite strand. For example dPTP can be incorporated into a nucleic acid molecule in place of a pyrimidine nucleotide (may replace thymine or cytosine); please see FIG. 6. Once in a nucleic acid strand, it may pair with adenine when in an imino tautomeric form. Thus, when a complementary strand is formed, that complementary strand may have an adenine present at a position complementary to the dPTP. Similarly, once in a nucleic acid strand, it may pair with guanine when in an amino tautomeric form. Thus, when a complementary strand is formed, that complementary strand may have a guanine present at a position complementary to the dPTP.

For example, if a dPTP is introduced into the at least one target nucleic acid molecule of the invention, when an at least one nucleic acid molecule complementary to the at least one target nucleic acid molecule is formed, the at least one nucleic acid molecule complementary to the at least one target nucleic acid molecule will comprise an adenine or a guanine at a position complementary to the dPTP in the at least one target nucleic acid molecule (depending on whether the dPTP is in its amino or imino form). When the at least one nucleic acid molecule complementary to the at least one target nucleic acid molecule is replicated, the resulting replicate of the at least one target nucleic acid molecule will comprise a thymine or a cytosine in a position corresponding to the dPTP in the at least one target nucleic acid molecule. Thus, a mutation to thymine or cytosine can be introduced into the mutated at least one target nucleic acid molecule.

Alternatively, if a dPTP is introduced in at least one nucleic acid molecule complementary to the at least one target nucleic acid molecule, when a replicate of the at least one target nucleic acid molecule is formed, the replicate of the at least one target nucleic acid molecule will comprise an adenine or a guanine at a position complementary to the dPTP in the at least one nucleic acid molecule complementary to the at least one target nucleic acid molecule (depending on the tautomeric form of the dPTP). Thus, a mutation to adenine or guanine can be introduced into the mutated at least one target nucleic acid molecule.

In an embodiment, the low bias DNA polymerase can replace cytosine or thymine with a nucleotide analog. In a further embodiment, the low bias DNA polymerase introduces guanine or adenine nucleotides using a nucleotide analog at a rate ratio of 0.5-1.5:0.5-1.5, 0.6-1.4:0.6-1.4, 0.7-1.3:0.7-1.3, 0.8-1.2:0.8-1.2, or around 1:1 respectively. The guanine or adenine nucleotides may be introduced by the low bias DNA polymerase pairing them opposite a nucleotide analog such as dPTP. In a further embodiment, the low bias DNA polymerase introduces guanine or adenine nucleotides using a nucleotide analog at a rate ratio of 0.7-1.3:0.7-1.3 respectively.

The skilled person can determine, using conventional methods, whether the low bias DNA polymerase is able to incorporate nucleotide analogs into the at least one target nucleic acid molecule or mutate adenine, thymine, guanine, and/or cytosine in the at least one target nucleic acid molecule using a nucleotide analog using conventional methods.

For example, in order to determine whether the low bias DNA polymerase is able to incorporate nucleotide analogs into the at least one target nucleic acid molecule, the skilled person could amplify a nucleic acid molecule using a low bias DNA polymerase for two rounds of replication. The first round of replication should take place in the presence of the nucleotide analog, and the second round of replication should take place in the absence of the nucleotide analog. The resulting amplified nucleic acid molecules could be sequenced to see whether mutations have been introduced, and if so, how many mutations. The user should repeat the experiment without the nucleotide analog, and compare the number of mutations introduced with and without the nucleotide analog. If the number of mutations that have been introduced with the nucleotide analog is significantly higher than the number of mutations that have been introduced without the nucleotide analog, the user can conclude that the low bias DNA polymerase is able to incorporate nucleotide analogs. Similarly, the skilled person can determine whether a DNA polymerase incorporates nucleotide analogs or mutates adenine, thymine, guanine, and/or cytosine using a nucleotide analog. The skilled person merely need perform the method in the presence of nucleotide analogs, and see whether the method leads to mutations at positions originally occupied by adenine, thymine, guanine, and/or cytosine.

If the user wishes to mutate the at least one target nucleic acid molecule using a nucleotide analog, the method may comprise a step of amplifying the at least one target nucleic acid molecule using a low bias DNA polymerase, where the step of amplifying the at least one target nucleic acid molecule using a low bias DNA polymerase is carried out in the presence of the nucleotide analog, and the step of amplifying the at least one target nucleic acid molecule provides at least one target nucleic acid molecule comprising the nucleotide analog.

Suitable nucleotide analogs include dPTP (2'deoxy-P-nucleoside-5'-triphosphate), 8-Oxo-dGTP (7,8-dihydro-8-oxoguanine), 5Br-dUTP (5-bromo-2'-deoxy-uridine-5'-triphosphate), 2OH-dATP (2-hydroxy-2'-deoxyadenosine-5'-triphosphate), dKTP (9-(2-Deoxy-β-D-ribofuranosyl)-N6-methoxy-2,6,-diaminopurine-5'-triphosphate) and dITP (2'-deoxyinosine 5'-trisphosphate). The nucleotide analog may be dPTP. The nucleotide analogs may be used to introduce the substitution mutations described in Table 1.

TABLE 1

| Nucleotide | Substitution |
| --- | --- |
| 8-oxo-dGTP | A:T to C:G and T:A to G:C |
| dPTP | A:T to G:C and G:C to A:T |
| 5Br-dUTP | A:T to G:C and T:A to C:G |
| 2OH-dATP | A:T to C:G, G:C to T:A and A:T to G:C |
| dITP | A:T to G:C and G:C to A:T |
| dKTP | A:T to G:C and G:C to A:T |

The different nucleotide analogs can be used, alone or in combination, to introduce different mutations into the at least one target nucleic acid molecule. Accordingly, the low bias DNA polymerase may introduce guanine to adenine substitution mutations, cytosine to thymine substitution mutations, adenine to guanine substitution mutations, and thymine to cytosine substitution mutations using a nucleotide analog. The low bias DNA polymerase may be able to introduce guanine to adenine substitution mutations, cytosine to thymine substitution mutations, adenine to guanine substitution mutations, and thymine to cytosine substitution mutations, optionally using a nucleotide analog.

The low bias DNA polymerase may be able to introduce guanine to adenine substitution mutations, cytosine to thymine substitution mutations, adenine to guanine substitution mutations, and thymine to cytosine substitution mutations at a rate ratio of 0.5-1.5:0.5-1.5:0.5-1.5:0.5-1.5, 0.6-1.4:0.6-1.4:0.6-1.4:0.6-1.4, 0.7-1.3:0.7-1.3:0.7-1.3:0.7-1.3, 0.8-1.2:0.8-1.2:0.8-1.2:0.8-1.2, or around 1:1:1:1 respectively. Preferably, the low bias DNA polymerase is able to introduce guanine to adenine substitution mutations, cytosine to thymine substitution mutations, adenine to guanine substitution mutations, and thymine to cytosine substitution mutations at a rate ratio of 0.7-1.3:0.7-1.3:0.7-1.3:0.7-1.3 respectively. Suitable methods for determining whether the low bias DNA polymerase is able to introduce substitution mutations and at what rate ratio are described under the heading "whether a DNA polymerase is able to mutate a nucleotide and, if so, at what rate".

In some methods the low bias DNA polymerase introduces guanine to adenine substitution mutations, cytosine to thymine substitution mutations, adenine to guanine substitution mutations, and thymine to cytosine substitution mutations at a rate ratio of 0.5-1.5:0.5-1.5:0.5-1.5:0.5-1.5, 0.6-1.4:0.6-1.4:0.6-1.4:0.6-1.4, 0.7-1.3:0.7-1.3:0.7-1.3:0.7-1.3, 0.8-1.2:0.8-1.2:0.8-1.2:0.8-1.2, or around 1:1:1:1 respectively. Preferably, the low bias DNA polymerase introduces guanine to adenine substitution mutations, cytosine to thymine substitution mutations, adenine to guanine substitution mutations, and thymine to cytosine substitution mutations at a rate ratio of 0.7-1.3:0.7-1.3:0.7-1.3:0.7-1.3 respectively. Suitable methods for determining whether substitution mutations are introduced and at what rate ratio are described under the heading "whether a DNA polymerase is able to mutate a nucleotide and, if so, at what rate".

Generally, when a low bias DNA polymerase uses a nucleotide analog to introduce a mutation, this requires more than one round of replication. In the first round of replication the low bias DNA polymerase introduces the nucleotide analog in place of a nucleotide, and in a second round of replication, that nucleotide analog pairs with a natural nucleotide to introduce a substitution mutation in the complementary strand. The second round of replication may be carried out in the presence of the nucleotide analog. However, the method may further comprise a step of amplifying the at least one target nucleic acid molecule comprising nucleotide analogs in the absence of nucleotide analogs. The step of amplifying the at least one target nucleic acid molecule comprising nucleotide analogs in the absence of nucleotide analogs may be carried out using the low bias DNA polymerase.

Optionally, the method provides a mutated at least one target nucleic acid molecule and the method comprises a further step of amplifying the mutated at least one target nucleic acid molecule using the low bias DNA polymerase.

Low Template Amplification Bias

The low bias DNA polymerase may have low template amplification bias. A low bias DNA polymerase has low template amplification bias if it is able to amplify different target nucleic acid molecules with similar degrees of success per cycle. High bias DNA polymerases may struggle to amplify template nucleic acid molecules that comprise a high G:C content or contain a large degree of secondary structure. In an embodiment, the low bias DNA polymerase of the invention has low template amplification bias for template nucleic acid molecules that are less than 25000, less than 10000, between 1 and 15000, or between 1 and 10000 nucleotides in length.

In an embodiment, to determine whether a DNA polymerase has low template amplification bias, the skilled person could amplify a range of different sequences using the DNA polymerase, and see whether the different sequences are amplified at different levels by sequencing the resultant amplified DNA. For example, the skilled person could select a range of short (possibly 50 nucleotide) nucleic acid molecules having different characteristics, including a nucleic acid molecule having high GC content, a nucleic acid molecule having low GC content, a nucleic acid molecule having a large degree of secondary structure and a nucleic acid molecule have a low degree of second structure. The user could then amplify those sequences using the DNA polymerase and quantify the level at which each of the nucleic acid molecules is amplified to. In an embodiment, if the levels are within 25%, 20%, 10%, or 5% of one another, then the DNA polymerase has low template amplification bias.

Alternatively, in an embodiment, a DNA polymerase has low template amplification bias if it is able to amplify 7-10 kbp fragments with a Kolmolgorov-Smirnov D of less than 0.1, less than 0.09, or less than 0.08. The Kolmolgorov-Smirnov D with which a particular low bias DNA polymerase is able to amplify 7-10 kbp fragments may be determined using an assay provided in Example 4.

The low bias DNA polymerase may be a high fidelity DNA polymerase. A high fidelity DNA polymerase is a DNA polymerase which is not highly error-prone, and so does not generally introduce a large number of mutations when used to amplify a target nucleic acid molecule in the absence of nucleotide analogs. High fidelity DNA polymerases are not generally used in methods for introducing mutations, as it is generally considered that error-prone DNA polymerases are more effective. However, the present application demonstrates that certain high fidelity polymerases are able to introduce mutations using a nucleotide analog, and that those mutations may be introduced with lower bias compared to error-prone DNA polymerases such as Taq polymerase.

High fidelity DNA polymerases have an additional advantage. High fidelity DNA polymerases can be used to introduce mutations when used with nucleotide analogs, but in the absence of nucleotide analogs they can replicate a target nucleic acid molecule highly accurately. This means that the user can mutate the at least one target nucleic acid molecule to high effect and amplify the mutated at least one target nucleic acid molecule with high accuracy using the same DNA polymerase. If a low fidelity DNA polymerase is used to mutate the target nucleic acid molecule, it may need to be removed from the reaction mixture before the target nucleic acid molecule is amplified.

High fidelity DNA polymerases may have a proof-reading activity. A proof-reading activity may help the DNA polymerase to amplify a target nucleic acid sequence with high accuracy. For example, a low bias DNA polymerase may comprise a proof-reading domain. A proof reading domain may confirm whether a nucleotide that has been added by the polymerase is correct (checks that it correctly pairs with the corresponding nucleic acid of the complementary strand) and, if not, excises it from the nucleic acid molecule. The inventors have surprisingly found that in some DNA polymerases, the proof-reading domain will accept pairings of natural nucleotides with nucleotide analogs. The structure and sequence of suitable proof-reading domains are known to the skilled person. DNA polymerases that comprise a proof-reading domain include members of DNA polymerase families I, II and III, such as Pfu polymerase (derived from *Pyrococcus furiosus*), T4 polymerase (derived from bacteriophage T4) and the Thermococcal polymerases that are described in more detail below.

In an embodiment, in the absence of nucleotide analogs, the high fidelity DNA polymerase introduces less than 0.01%, less than 0.0015%, less than 0.001%, between 0% and 0.0015%, or between 0% and 0.001% mutations per round of replication.

In addition, the low bias DNA polymerase may comprise a processivity enhancing domain. A processivity enhancing domain allows a DNA polymerase to amplify a target nucleic acid molecule more quickly. This is advantageous as it allows the methods of the invention to be performed more quickly.

Thermococcal Polymerases

In an embodiment, the low bias DNA polymerase is a fragment or variant of a polypeptide comprising SEQ ID NO. 2, SEQ ID NO. 4, SEQ ID NO. 6 or SEQ ID NO.7. The polypeptides of SEQ ID NO. 2, 4, 6 and 7 are thermococcal polymerases. The polymerases of SEQ ID NO. 2, SEQ ID NO. 4, SEQ ID NO. 6 or SEQ ID NO. 7 are low bias DNA polymerases having high fidelity, and they can mutate target nucleic acid molecules by incorporating a nucleotide analog such as dPTP. The polymerases of SEQ ID NO. 2, SEQ ID NO. 4, SEQ ID NO. 6 or SEQ ID NO. 7 are particularly advantageous as they have low mutation bias and low template amplification bias. They are also highly processive and are high fidelity polymerases comprising a proof-reading domain, meaning that, in the absence of nucleotide analogs, they can amplify mutated target nucleic acid molecules quickly and accurately.

The low bias DNA polymerase may comprise a fragment of at least 400, at least 500, at least 600, at least 700, or at least 750 contiguous amino acids of:
a. a sequence of SEQ ID NO. 2;
b. a sequence at least 95%, at least 98%, or at least 99% identical to SEQ ID NO. 2;
c. a sequence of SEQ ID NO. 4;
d. a sequence at least 95%, at least 98%, or at least 99% identical to SEQ ID NO. 4;
e. a sequence of SEQ ID NO. 6;
f. a sequence at least 95%, at least 98%, or at least 99% identical to SEQ ID NO. 6;
g. a sequence of SEQ ID NO. 7; or
h. a sequence at least 95%, at least 98%, or at least 99% identical to SEQ ID NO. 7.

Preferably, the low bias DNA polymerase comprises a fragment of at least 700 contiguous amino acids of:
a. a sequence of SEQ ID NO. 2;
b. a sequence at least 98%, or at least 99% identical to SEQ ID NO. 2;
c. a sequence of SEQ ID NO. 4;
d. a sequence at least 98%, or at least 99% identical to SEQ ID NO. 4;
e. a sequence of SEQ ID NO. 6;
f. a sequence at least 98%, or at least 99% identical to SEQ ID NO. 6;
g. a sequence of SEQ ID NO. 7; or
h. a sequence at least 98%, or at least 99% identical to SEQ ID NO. 7.

The low bias DNA polymerase may comprise:
a. a sequence of SEQ ID NO. 2;
b. a sequence at least 95%, at least 98%, or at least 99% identical to SEQ ID NO. 2;
c. a sequence of SEQ ID NO. 4;
d. a sequence at least 95%, at least 98%, or at least 99% identical to SEQ ID NO. 4;
e. a sequence of SEQ ID NO. 6;
f. a sequence at least 95%, at least 98%, or at least 99% identical to SEQ ID NO. 6;
g. a sequence of SEQ ID NO. 7; or
h. a sequence at least 95%, at least 98%, or at least 99% identical to SEQ ID NO. 7.

Preferably, the low bias DNA polymerase comprises:
a. a sequence of SEQ ID NO. 2;
b. a sequence at least 98%, or at least 99% identical to SEQ ID NO. 2;
c. a sequence of SEQ ID NO. 4;
d. a sequence at least 98%, or at least 99% identical to SEQ ID NO. 4;
e. a sequence of SEQ ID NO. 6;
f. a sequence at least 98%, or at least 99% identical to SEQ ID NO. 6;
g. a sequence of SEQ ID NO. 7; or
h. a sequence at least 98%, or at least 99% identical to SEQ ID NO. 7.

The low bias DNA polymerase may be a thermococcal polymerase, or derivative thereof. The DNA polymerases of SEQ ID NO 2, 4, 6 and 7 are thermococcal polymerases. Thermococcal polymerases are advantageous, as they are generally high fidelity polymerases that can be used to introduce mutations using a nucleotide analog with low mutation and template amplification bias.

A thermococcal polymerase is a polymerase having the polypeptide sequence of a polymerase isolated from a strain of the *Thermococcus* genus. A derivative of a thermococcal polymerase may be a fragment of at least 400, at least 500, at least 600, at least 700, or at least 750 contiguous amino acids of a thermococcal polymerase, or at least 95%, at least 98%, at least 99%, or 100% identical to a fragment of at least 400, at least 500, at least 600, at least 700, or at least 750 contiguous amino acids of a thermococcal polymerase. The derivative of a thermococcal polymerase may be at least 95%, at least 98%, at least 99%, or 100% identical to a thermococcal polymerase. The derivative of a thermococcal polymerase may be at least 98% identical to a thermococcal polymerase.

A thermococcal polymerase from any strain may be effective in the context of the present invention. In an embodiment, the thermococcal polymerase is derived from a thermococcal strain selected from the group consisting of *T. kodakarensis, T. celer, T. siculi*, and *T. sp* KS-1. Thermocoeccal polymerases from these strains are described in SEQ ID NO. 2, SEQ ID NO. 4, SEQ ID NO. 6 and SEQ ID NO. 7.

Optionally, the low bias DNA polymerase is a polymerase that has high catalytic activity at temperatures between 50° C. and 90° C., between 60° C. and 80° C., or around 68° C.

Barcodes, Sample Tags and Adapters

The method may further comprise introducing barcodes into the target nucleic acid molecules. For the purposes of the present invention, a barcode is a degenerate or randomly generated sequence of nucleotides. The term "barcode" is synonymous with the terms "unique molecular identifiers" (UMIs) or "unique molecular tags" (UMTs). The method may comprise introducing 1, 2 or more barcodes into the target nucleic acid molecules. In a preferred embodiment, the method comprises introducing a variety of barcodes into the target nucleic acid molecules, such that, after the barcodes are introduced, most of the original target nucleic acid molecules comprise unique barcodes compared to other original target nucleic acid molecules.

Introducing barcodes into the target nucleic acid molecules may be useful if the method for introducing mutations of the invention is used as part of a method for determining a sequence. The use of barcodes may help the user to identify which of the original at least one target nucleic acid molecules each sequence of at least one of target nucleic acid molecule (or amplified or fragmented at least one target nucleic acid molecule) was derived from. If the barcodes used in each original target nucleic acid molecule are different, the user can sequence the barcodes or the target nucleic acid molecules, and sequences of target nucleic acid molecules comprising the same barcodes are likely to be sequences of target nucleic acid molecules that originated from the same original target nucleic acid molecule.

The method for introducing mutations into at least one target nucleic acid molecule may comprise introducing sample tags into the target nucleic acid molecules. A sample tag is a short series of nucleic acids of known (specified) sequence. For example, the method of the invention may be performed on multiple target nucleic acid molecules taken from different samples. Those samples may be pooled, but prior to pooling, a sample tag may introduced into the target nucleic acid molecules in a sample (the target nucleic acid molecules are labelled with a sample tag). Target nucleic acid molecules from different samples may be labelled with different sample tags. Optionally, target nucleic acid molecules from the same sample are labelled with the same sample tag or a sample tag from the same sub-group of sample tags. For example, if the user decides to use two samples, the target nucleic acid molecules in the first sample may be labelled with a first sample tag having a specified sequence and the target nucleic acid molecules in the second sample may be tagged with a second sample tag having a second specified sequence. Similarly, if the user decides to use two samples, the target nucleic acid molecules in the first sample may be labelled with a sample tag from a first sub-group of sample tags and the target nucleic acid molecules in the second sample may be labelled with a sample tag from a second sub-group of sample tags. The user would understand that any target nucleic acid molecules comprising the first sample tag or a sample tag from the first sub-group of sample tags originated from the first sample, and any target nucleic acid molecules comprising the second sample tag or a sample tag from the second sub-group of sample tags originated from the second sample. It is possible to determine which tag has been used to label a target nucleic acid sequence by sequencing the target nucleic acid sequence. Suitable sequencing methods are described in more detail below.

In an embodiment, the sample tags are introduced (the target nucleic acid molecules are labelled with a sample tag) prior to the step of amplifying the at least one target nucleic acid molecule using a low bias DNA polymerase. This is advantageous as it means that samples may be pooled at an early stage in the method, reducing handling time, the number of reagents required and the possibility of introducing sample handling mistakes. However, if the sample tags are introduced prior to the step of amplifying the at least one target nucleic acid molecule using a low bias DNA polymerase, it is possible that the sample tags will be mutated by the low bias DNA polymerase. The present inventors have designed groups of samples tags that are designed such that they may be distinguished from one another even if they have been mutated.

In an embodiment, a group of sample tags is used and target nucleic acid molecules from different samples are labelled with different sample tags from the group. Target nucleic acid molecules from the same sample may be labelled with the same sample tag from the group or with a sample tag from the same sub-group of samples tags from the group. For example, if the group of sample tags comprises sample tags named A, B, C and D, all target nucleic acid molecules in a first sample may be labelled using A or A/B, and all the target nucleic acid molecules in a second sample may be labelled using C or C/D. Each sample tag in the group of sample tags may differ from substantially all other sample tags in the group by at least 1 low probability mutation difference. Each sample tag in the group of sample tags may differ from all other sample tags in the group by at least 1 low probability mutation difference.

In an aspect, the invention provides a group of sample tags, wherein each sample tag in the group differs from substantially all other sample tags in the group by at least 1 low probability mutation difference. Each sample tag may differ from all other sample tags in the group by at least 1 low probability mutation difference.

By the term "differs from substantially all other sample tags in the group by at least 1 low probability mutation difference" we mean that each tag has been designed such that if the sample tags are mutated by at least 1 low probability mutation, the tags will still be different to one another almost (substantially all or all other tags). In an embodiment, the term "substantially all other sample tags" refers to at least 90%, at least 95%, or at least 98% of the other sample tags. A low probability mutation is a mutation that occurs infrequently in the method for introducing mutations of the invention. For example, a low probability mutation may be a transversion mutation, or an indel mutation. Transversion mutations and indel mutations occur infrequently when the method for introducing mutations of the invention is performed using dPTP as a nucleotide analog. A transversion mutation is a replacement of a purine nucleotide with a pyrimidine nucleotide (adenine to cytosine, adenine to thymine, guanine to cytosine or guanine to thymine), or a pyrimidine nucleotide with a purine nucleotide (cytosine to adenine, cytosine to guanine, thymine to adenine, or thymine to guanine). An indel mutation is a deletion mutation or an insertion mutation. Suitable tags may be designed computationally using statistical methods. For example, the skilled person would be able to determine what type of mutation is a low probability mutation in a method for introducing mutations of the invention. The skilled person can perform the method for introducing mutations of the invention, and determine the types of mutations that have been introduced by sequencing the nucleic acid molecule product. The mutations that occur most frequently are high probability mutations, and the mutations that occur least frequently are low probability mutations.

The user could generate suitable sample tags using the method for designing a group of sample tags of the invention.

Optionally, each sample tag differs from substantially all other sample tags in the group by at least 2, at least 3, at least 4, at least 5, between 3 and 50, between 3 and 25, or between 3 and 10 low probability mutation differences. Optionally, each sample tag differs from all other sample tags in the group by at least 2, at least 3, at least 4, at least 5, between 3 and 50, between 3 and 25, or between 3 and 10 low probability mutation differences.

Each sample tag may differ from substantially all other sample tags in the group by at least 2 high probability mutation differences. A high probability mutation difference, is a mutation that occurs frequently in a method for introducing mutations of the invention. For example, a high probability mutation difference may be a transition mutation. A transition mutation is a replacement of a purine nucleotide with another purine nucleotide (adenine to guanine or guanine to adenine), or a pyrimidine nucleotide with another pyrimidine nucleotide (cytosine to thymine or thymine to cytosine).

Each sample tag may differ from all other sample tags in the group by at least 2 high probability mutation differences, i.e. each sample tag has been designed such that if the sample tags are mutated by at least 2 high probability mutations, the tags will still be different to one another.

Optionally, each sample tag differs from substantially all other sample tags in the group by at least 3, between 2 and 50, between 3 and 25, or between 3 and 10 high probability mutation differences. Optionally, each sample tag differs from all other sample tags in the group by at least 3, between 2 and 50, between 5 and 25, or between 5 and 10 high probability mutation differences.

In an embodiment, each sample tag is at least 8 nucleotides, at least 10 nucleotides, at least 12 nucleotides, between 8 and 50 nucleotides, between 10 and 50 nucleotides, or between 10 and 50 nucleotides in length.

Suitable sample tags are those of SEQ ID NOs: 8-136.

The method may further comprise introducing adapters into each of the target nucleic acid molecules. The adapters may comprise a primer binding site. For the purposes of the invention, primer binding sites are known sequences of nucleotides that are sufficiently long for primers to specifically hybridise to. Optionally, the primer binding sites are at least 8, at least 10, at least 12, between 8 and 50, or between 10 and 25 nucleotides in length.

The method may comprise introducing a first adapter at the 3' end of the at least one target nucleic acid molecule and a second adapter at the 5' end of the at least one target nucleic acid molecule, wherein the first adapter and the second adapter can anneal to one another.

In an aspect, the invention provides a method for preferentially amplifying nucleic acid molecules that are larger than 1 kbp in length comprising:
a. providing at least one sample comprising target nucleic acid molecules;
b. introducing a first adapter at the 3' end of the target nucleic acid molecules and a second adapter at the 5' end of the target nucleic acid molecules; and
c. amplifying the target nucleic acid molecules using primers that are complementary to a portion of the first adapter,
wherein the first adapter and the second adapter can anneal to one another.

The second adapter may comprise a portion that is complementary to a first primer binding site and the first adapter may comprise the first primer binding site.

Figure 4:
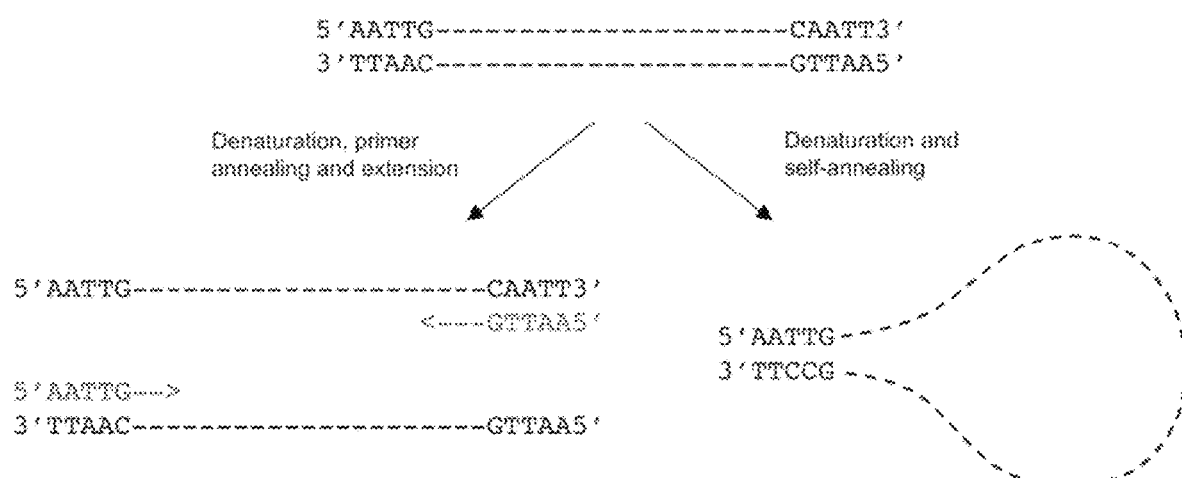
FIG. 4 depicts self annealing of nucleic acid molecules when a first primer binding site and a second primer binding site that anneal to one another are used.

The present inventors have found that by introducing a first adapter and a second adapter that can anneal to one another into the at least one target nucleic acid molecule, they can ensure that the methods of the invention preferentially amplify and/or mutate long target nucleic acid molecules. If the first adapter can anneal to the second adapter, then they may do so in the methods of the invention resulting in a self-annealed at least one target nucleic acid molecule (as indicated in FIG. 4). Self-annealed target nucleic acid molecules are not replicated and so will not be amplified and/or mutated by the methods of the invention. The likelihood that the first adapter and the second adapter anneal to one another during the methods of the invention will be higher for shorter target nucleic acid molecules than for longer target nucleic acid molecules. For these reasons, the addition of a first adapter and a second adapter to the at least one target nucleic acid molecule of the invention can be used to preferentially amplify larger at least one target nucleic acid molecules.

The method for preferentially amplifying nucleic acid molecules may be a method for preferentially amplifying target nucleic acid molecules that are longer than 1.5 kbp. The method may further comprise a step of sequencing the target nucleic acid molecules. Examples of possible sequencing methods include Maxam Gilbert Sequencing, Sanger Sequencing, nanopore sequencing or sequencing comprising bridge PCR. In a typical embodiment, the sequencing steps involve bridge PCR. Optionally, the bridge PCR step is carried out using an extension time of greater than 5, greater than 10, greater than 15 or greater than 20 seconds. An example of the use of bridge PCR is in Illumina Genome Analyzer Sequencers.

It is possible for a user to determine whether a first adapter and a second adapter can anneal to one another. In an embodiment, the user may identify whether a first adapter and a second adapter can anneal to one another by providing a nucleic acid molecule comprising the first adapter, and seeing whether a primer comprising the second adapter is capable of initiating replication of the nucleic acid molecule under PCR conditions.

Alternatively, in an embodiment, the first adapter and the second adapter can be considered to be able to anneal to one another if they hybridise under the following conditions: equimolar concentrations of the two primers are combined (e.g. 50 µM), then incubated at a high temperature such as 95° C. for 5 minutes to ensure that the primers are single-stranded. The solution is then slowly cooled to room temperature (25° C.) over a period of approximately 45 minutes.

The methods may comprise amplifying the target nucleic acid molecules using primers that are identical to one another, or substantially identical to one another. The primers may be complementary to a portion of the first adapter. Two primers are "substantially identical" to one another if they have an identical sequence, or a sequence that differs by 1, 2 or 3 nucleotides. In a preferred embodiment, the methods of the invention comprise amplifying the target nucleic acid molecules using primers that are identical in sequence or differ by a single nucleotide difference.

In an embodiment, the first adapter and the second adapter comprise sequences that are complementary to one another, or substantially complementary to one another. The first adapter may be substantially complementary to the second adapter if the first adapter is complementary to a nucleic acid molecule that is at least 80%, at least 90%, at least 95%, or at least 99% identical to the second adapter.

The user may use primers that comprise primer binding sites, and these primers may be used to preferentially amplify replicates of the at least one target nucleic acid molecule that were generated in the last round of replication. For example, a first set of primers comprising a third primer binding site may be used in a round of replication. In a further round of replication a second set of primers may be used that bind to the third primer binding site. The second set of primers will only replicate replicates of the at least one target nucleic acid molecule that were generated in a previous round of replication, using the first set of primers.

Third and further sets of primers may be used. Preferentially replicating replicates of a previous round of replication is advantageous as it can ensure that each amplified target nucleic acid molecule comprises a high level of mutation (since only at least one target nucleic acid molecules that have been exposed to at least one round of amplification by the low bias DNA polymerase will be replicated).

Accordingly, the methods of the invention may comprise:
(a) introducing a first adapter comprising a first primer binding site at the 3' end of the at least one target nucleic acid molecule or target nucleic acid molecules and a second adapter comprising a portion that is complementary to the first primer binding site at the 5' end of the at least one target nucleic acid molecule or target nucleic acid molecules, wherein the first adapter and the second adapter can anneal to one another;
(b) amplifying the target nucleic acid molecules using a first set of primers that are complementary to the first primer binding site and comprise a second primer binding site, optionally using a low bias DNA polymerase; and
(c) amplifying the target nucleic acid molecules using a second set of primers that are complementary to the second primer binding site, optionally using a low bias DNA polymerase.

The second set of primers may comprise a third primer binding site, and further amplification steps may be carried out using a third or further sets of primers that are complementary to the third or further primer binding sites.

The barcodes, sample tags and/or adapters may be introduced using any suitable method including PCR, tagmentation and physical shearing or restriction digestion of target nucleic acids combined with subsequent adapter ligation (optionally sticky-end ligation). For example, PCR can be carried out on the at least one target template nucleic acid molecule using a first set of primers capable of hybridising to the at least one target nucleic acid molecule. The barcodes, sample tags and adapters may be introduced into each of the at least one target nucleic acid molecules by PCR using primers comprising a portion (a 5' end portion) comprising a barcode, a sample tag and/or an adapter, and a portion (a 3' end portion) having a sequence that is capable of hybridising to (optionally complementary to) the at least one target nucleic acid molecule. Such primers will hybridise to a target nucleic acid molecule, PCR primer extension will then provide a nucleic acid molecule which comprises a barcode, sample tag and/or an adapter. A further cycle of PCR with these primers can be used to add a barcode, sample tag and/or an adapter to the other end of the at least one target nucleic acid molecule. The primers may be degenerate, i.e. the 3' end portion of the primers may be similar but not identical to one another.

The barcodes, sample tags and/or adapters may be introduced using tagmentation. The barcodes, sample tags and/or adapters can be introduced using direct tagmentation, or by introducing a defined sequence by tagmentation followed by two cycles of PCR using primers that comprise a portion capable of hybridising to the defined sequence, and a portion comprising a barcode, a sample tag and/or an adapter. The barcodes, sample tags and/or adapters can be introduced by restriction digestion of the original at least one target nucleic acid molecule followed by ligation of nucleic acids comprising the barcode, sample tag and/or an adapter. The restriction digestion of the original at least one nucleic acid molecule should be performed such that the digestion results in a nucleic acid molecule comprising the region to be sequenced (the at least one target template nucleic acid molecule). The barcodes, sample tags and/or adapters may be introduced by shearing the at least one target nucleic acid molecule, followed by end repair, A-tailing and then ligation of nucleic acids comprising the barcode, sample tag and/or an adapter.

A Method for Determining a Sequence of at Least One Target Nucleic Acid Molecule One aspect of the invention relates to a method for determining a sequence of at least one target nucleic acid molecule comprising the method for introducing mutations of the invention.

As described above, the method for introducing mutations of the invention can be useful as part of a method for determining a sequence of at least one target nucleic acid molecule, as the mutations can enable the skilled person to assemble sequences.

As described in the background section, sequencing methods can be improved by incorporating steps that introduce mutations into at least one target nucleic acid molecule that is to be sequenced. A user will often amplify and/or fragment the at least one target nucleic acid molecule prior to sequencing it. The user will then assemble a consensus sequence for at least one of the target nucleic acid molecules from the sequences of regions of the amplified or fragmented at least one target nucleic acid molecule. Introducing mutations into the at least one target nucleic acid molecules prior to amplification or fragmentation can help the user to identify which of the original at least one template nucleic acid molecules each sequence of regions of amplified or fragmented at least one target nucleic acid molecule was derived from, and so improve the accuracy of the consensus sequences.

The more random the mutations that are introduced, the easier it is to identify which of the original at least one target nucleic acid molecule each sequence of amplified or fragmented at least one target nucleic acid molecule was derived from. The method of introducing mutations of the invention, which utilises a low bias DNA polymerase, can be used to introduce mutations in a substantially random way, and so is ideal for inclusion in a method for determining a sequence of at least one target nucleic acid molecule.

The method for determining a sequence of at least one target nucleic acid molecule may comprise steps of:
a. performing the method for introducing mutations into at least one target nucleic acid molecule of the invention to provide at least one mutated target nucleic acid molecule;
b. sequencing regions of the least one mutated target nucleic acid molecule to provide mutated sequence reads; and
c. assembling a sequence for at least a portion of the at least one target nucleic acid molecule using the mutated sequence reads.

In general, sequencing steps can be carried out using any method of sequencing. Examples of possible sequencing methods include Maxam Gilbert Sequencing, Sanger Sequencing, nanopore sequencing, or sequencing comprising bridge PCR. In a typical embodiment, the sequencing steps involve bridge PCR. Optionally, the bridge PCR step is carried out using an extension time of greater than 5, greater than 10, greater than 15 or greater than 20 seconds. An example of the use of bridge PCR is in Illumina Genome Analyzer Sequencers.

The method may comprise sequencing regions of at least one mutated target nucleic acid molecule to provide mutated sequence reads. The regions may correspond to a fragment that may comprise a substantial portion of the at least one mutated target nucleic acid molecule. It may be that the entire at least one mutated target nucleic acid molecule cannot be sequenced for some reason, but the user may still find the sequence of a portion of the at least one mutated target nucleic acid molecule to be useful. The regions of the at least one mutated target nucleic acid molecule may comprise the entire length of the at least one mutated target nucleic acid molecule.

The method may comprise assembling a sequence for at least a portion of the at least one target nucleic acid molecule from the mutated sequence reads. The sequence may be assembled by aligning the mutated sequence reads and grouping together reads that share the same mutation pattern. A sequence will be assembled from mutated sequence reads in the same group. The assembly may be carried out using software such as Clustal W2, IDBA-UD or SOAPdenovo.

The method for determining a sequence of at least one target nucleic acid molecule may comprise steps of:
a. performing the method for introducing mutations into at least one target nucleic acid molecule of the invention to provide at least one mutated target nucleic acid molecule;
b. fragmenting and/or amplifying the at least one mutated target nucleic acid molecule to provide at least one fragmented and/or amplified mutated target nucleic acid molecule;
c. sequencing regions of the at least one fragmented and/or amplified mutated target nucleic acid molecule to provide mutated sequence reads; and
d. assembling a sequence for at least a portion of the at least one target nucleic acid molecule using the mutated sequence reads.

A step of amplifying the at least one mutated target nucleic acid molecule could be performed by any suitable amplification technique such as PCR. Suitably, the PCR is carried out using the low bias DNA polymerase under conditions such as those described under the heading "amplifying the at least one target nucleic acid molecule using a low bias DNA polymerase".

A step of fragmenting the at least one mutated target nucleic acid molecule could be carried out using any appropriate method. For example, fragmentation can be carried out using restriction digestion or using PCR with primers complementary to at least one internal region of the at least one mutated target nucleic acid molecule. Preferably, fragmentation is carried out using a technique that produces arbitrary fragments. The term "arbitrary fragment" refers to a randomly generated fragment, for example a fragment generated by tagmentation. Fragments generated using restriction enzymes are not "arbitrary" as restriction digestion occurs at specific DNA sequences defined by the restriction enzyme that is used. Even more preferably, fragmentation is carried out by tagmentation. If fragmentation is carried out by tagmentation, the tagmentation reaction optionally introduces an adapter region into the at least one mutated target nucleic acid molecule. This adapter region is a short DNA sequence which may encode, for example, adapters to allow the at least one mutated target nucleic acid molecule to be sequenced using Illumina technology.

The fragmentation step may comprise a further step of enriching the at least one mutated fragmented target nucleic acid molecule. The step of enriching the at least one mutated fragmented target nucleic acid molecule may be carried out by PCR. Suitably, the PCR is carried out using the low bias DNA polymerase under conditions such as those described under the heading "amplifying the at least one target nucleic acid molecule using a low bias DNA polymerase".

A Method for Engineering a Protein

The method for introducing mutations of the invention may be useful as part of a method for engineering a protein. For example, protein engineering may involve searching for mutations that increase or decrease the activity of a protein, or change its structure. As part of protein engineering, a user may wish to randomly mutate the protein and see how the mutations effect the activity or structure of the protein. The present method is a method that results in highly random mutagenesis, and so can advantageously be used as part of a method for engineering a protein.

Accordingly, in one aspect of the invention there is provided a method for engineering a protein comprising the method for introducing mutations of the invention.

The method may comprise steps of:
a. performing a method for introducing mutations of the invention to provide at least one mutated target nucleic acid molecule;
b. inserting the at least one mutated target nucleic acid molecule into a vector; and
c. expressing a protein encoded by the at least one mutated target nucleic acid molecule.

The method may comprise steps of:
a. performing a method for introducing mutations of the invention to provide at least one mutated target nucleic acid molecule;
b. amplifying the at least one target nucleic acid molecule using a low bias DNA polymerase in the presence of a nucleotide analog to provide target nucleic acid molecules comprising a nucleotide analog;
c. amplifying the target nucleic acid molecules comprising a nucleotide analog in the absence of nucleotide analogs to provide at least one mutated target nucleic acid molecule;
d. inserting the at least one mutated target nucleic acid molecule into a vector; and
e. expressing a protein encoded by the at least one mutated target nucleic acid molecule.

Any suitable vector can be used. Optionally the vector is a plasmid, a virus, a cosmid or an artificial chromosome. Typically, the vector further comprises a control sequence operably linked to the inserted sequence, thus allowing for expression of a polypeptide. Preferably, the vector of the invention further comprises appropriate initiators, promoters, enhances and other elements which may be necessary and which are positioned in the correct orientation, in order to allow for expression of a polypeptide.

Optionally, the step of expressing the at least one mutated target nucleic acid molecule is achieved by transforming bacterial cells, transfecting eukaryotic cells or transducing eukaryotic cells with the vector. Optionally, the bacterial cells are *Escherichia coli* (*E. coli*) cells.

For example, the step of expressing the at least one mutated target nucleic acid molecule may comprise inserting the at least one mutated target nucleic acid molecule into a plasmid vector and transforming *E. coli* with the plasmid. The plasmid may comprise control elements suitable for expressing in *E. coli* such as a lac or T7 promoter (Dubendorff J W, Studier F W (1991). "*Controlling basal expression in an inducible T7 expression system by blocking the target T7 promoter with lac repressor*". Journal of Molecular Biology. 219 (1): 45-59.)). Suitable expression techniques are described in Sambrook, J. et al., (1989) Molecular Cloning: A Laboratory Manual Second Ed., Cold Spring Harbor Laboratory Press, Cold Spring Harbor, New York.

Alternatively, the step of expressing the at least one mutated target nucleic acid molecule may comprise expressing fragments produced directly from the step of amplifying the target nucleic acid molecules using an in vitro method.

The method may further comprise a step of testing the activity or assessing the structure of the protein encoded by the at least one mutated target nucleic acid molecule.

The step of testing the activity or assessing the structure of the protein encoded by the at least one mutated target nucleic acid molecule may be carried out using any number of well-known techniques. For example, the skilled person would be aware of suitable techniques for assessing the structure of a protein, including nuclear magnetic resonance (NMR) techniques, microscopy techniques such as cryo-electron microscopy, small angle x-ray scattering techniques, or X-ray crystallography.

Similarly, the skilled person would be aware of techniques that could be used for assessing the activity of a protein. The method used will depend on the protein that is encoded by the at least one mutated target nucleic acid molecule. For example, if the protein that is encoded by the at least one mutated target nucleic acid molecule is a blood clotting factor, the skilled person would test the protein for clotting activity, for example using a chromogenic clotting assay. Alternatively, if the protein that is encoded by the at least one mutated target nucleic acid molecule is an enzyme, the skilled person could test the activity of the enzyme by measuring the rate at which it catalyses its reaction, for example by measuring reduction in concentration of a starting product or increase in concentration of an end product of the reaction catalysed by the enzyme.

A Method for Designing a Group of Sample Tags

In an aspect, the invention further provides a method for designing a group of sample tags suitable for use in a method for introducing mutations into at least one target nucleic acid molecule comprising:
 a. analysing the method for introducing mutations into at least one target nucleic acid molecule and determining the average number of low probability mutations that take place during the method for introducing mutations into at least one target nucleic acid molecule; and
 b. determining sequences for a group of sample tags wherein each sample tag differs from substantially all sample tags in the group by more low probability mutation differences than the average number of low probability mutations that take place during the method for introducing mutations into at least one target nucleic acid molecule.

For example, the user may generate a first putative sample tag by using a computer programme to generate a random sequence. The first putative sample tag is added to the group of sample tags. The user may then generate a second putative sample tag in the same manner, and compare the sequence of the second putative sample tag to the first putative sample tag to see whether the second sample tag differs from the first sample tag such that even if the relevant number of low probability mutations were introduced into the second putative sample tag it would still differ from the first putative sample tag. If yes, then the second putative sample tag is added to the group of sample tags. If no, then the second putative sample tag is discarded. This may be repeated for third and further putative sample tags.

As discussed above, it is advantageous for sample tags to be added to at least one target nucleic acid molecule in a method for introducing mutations into at least one target nucleic acid molecule. However, if the sample tags are added prior to the mutations being introduced, this may mean that the sample tags are mutated and cannot then be used to distinguish target nucleic acid molecules that originated from the same or different samples. This can be avoided by designing the sample tags such that even if they are mutated they are sufficiently different from one another for the user to be able to distinguish between them.

The method may further comprise:
 a. (i) analysing the method for introducing mutations into at least one target nucleic acid molecule and determining the average number of high probability mutations that take place during the method for introducing mutations into at least one target nucleic acid molecule; and
 (ii) determining sequences for a group of sample tags wherein each sample tag differs from substantially all sample tags in the group by more high probability mutation differences than the average number of high probability mutations that take place during the method for introducing mutations into at least one target nucleic acid molecule.

A low probability mutation may be a transversion mutation or an indel mutation. A high probability mutation may be a transition mutation.

The method may be a computer implemented method.

In a further aspect of the invention, there is a provided a computer-readable medium configured to perform the method for designing a group of sample tags suitable for use in a method for introducing mutations into at least one target nucleic acid molecule.

In a further aspect of the invention, there is provided a group of sample tags obtainable by the method for designing sample tags of the invention. Optionally, the group of sample tags are obtained by the method for designing sample tags of the invention.

Using dNTPs at Unequal Concentrations

The step of amplifying the at least one target nucleic acid using a low bias DNA polymerase may be carried out using dNTPs at unequal concentrations.

In an aspect of the invention, there is provided a method for introducing mutations into at least one target nucleic acid molecule comprising:
 a. providing at least one sample comprising at least one target nucleic acid molecule; and
 b. introducing mutations into the at least one target nucleic acid molecule by amplifying the at least one target nucleic acid molecule using a DNA polymerase to provide a mutated at least one target nucleic acid molecule,
wherein step b. is carried out using dNTPs at unequal concentrations.

In order to be able to amplify the at least one target nucleic acid using a DNA polymerase (such as a low bias DNA polymerase), the target nucleic acid may be exposed to the DNA polymerase and dNTPs under conditions suitable for DNA replication to take place, for example in a PCR machine. If a step of amplifying the at least one target nucleic acid is carried out using dNTPs at unequal concentrations, the target nucleic acid is exposed to a DNA polymerase (such as a low bias DNA polymerase) and dNTPs, wherein the concentrations of the dNTPs are different relative to one another.

The term dNTPs is intended to refer to deoxynucleotides. Specifically, in the context of the present application, the term "dNTPs" is intended to refer to a solution comprising dTTP (deoxythymidine triphosphate) or dUTP (deoxyuridine), dGTP (deoxyguanidine triphosphate), dCTP (deoxycytidine triphosphate), and dATP (deoxyadenosine triphosphate). Optionally, "dNTPs" refers to a solution comprising dTTP (deoxythymidine triphosphate), dGTP (deoxyguanidine triphosphate), dCTP (deoxycytidine triphosphate), and dATP (deoxyadenosine triphosphate).

By the phrase "dNTPs at unequal concentrations" is meant that the four dNTPs are present in solution at different concentrations relative to one another. For example, one dNTP may be present at a higher concentration compared to (than) the other three dNTPs, two dNTPs may be present at a higher concentration compared to (than) the other two dNTPS, or three dNTPs may be present at a higher concentration compared to (than) the other one dNTP.

DGTP may be present at a higher concentration compared to (than) dCTP, dTTP and dATP, dGTP may be present at a higher concentration compared to (than) dTTP and dATP, dGTP may be present at a higher concentration compared to (than) dATP, dGTP may be present at a higher concentration compared to (than) dTTP, dCTP may be present at a higher concentration compared to (than) dGTP, dTTP and dATP, dCTP may be present at a higher concentration compared to (than) dTTP and dATP, dCTP may be present at a higher concentration compared to (than) dATP, dCTP may be present at a higher concentration compared to (than) dTTP, dTTP may be present at a higher concentration compared to (than) dGTP, dCTP and dATP, dTTP may be present at a higher concentration compared to (than) dGTP and dCTP, dTTP may be present at a higher concentration compared to (than) dCTP, dTTP may be present at a higher concentration compared to (than) dGTP, dATP may be present at a higher concentration compared to (than) dGTP, dTTP and dCTP, dATP may be present at a higher concentration compared to (than) dGTP and dCTP, dATP may be present at a higher concentration compared to (than) dGTP, dATP may be present at a higher concentration compared to dGTP, dCTP and dATP may be present at a higher concentration compared to (than) dGTP and dCTP, or dGTP and dCTP may be present at a higher concentration compared to (than) dATP and dTTP.

The user may prepare solutions of dNTPs at unequal concentrations in any convenient manner. DATP, dTTP, dGTP and dTTP solutions are readily commercially available, and the user merely needs to mix these in an appropriate ratio.

Optionally, the method:
(i) comprises a further step of amplifying the at least one target nucleic acid molecule comprising nucleotide analogs in the absence of nucleotide analogs and the further step of amplifying the at least one target nucleic acid molecule comprising nucleotide analogs in the absence of nucleotide analogs is carried out using dNTPs at unequal concentrations; or
(ii) provides a mutated at least one target nucleic acid molecule, and comprises a further step of amplifying the mutated at least one target nucleic acid molecule using the low bias DNA polymerase and the further step of amplifying the mutated at least one target nucleic acid molecule using the low bias DNA polymerase is carried out using dNTPs at unequal concentrations.

Optionally, introducing mutations into the at least one target nucleic acid molecule by amplifying the at least one target nucleic acid molecule using a DNA polymerase to provide a mutated at least one target nucleic acid molecule is carried out in the presence of a nucleotide analog. Optionally, the method for introducing mutations into at least one target nucleic acid molecule comprises a step of amplifying the mutated at least one target nucleic acid molecule in the absence of the nucleotide analog, and optionally this step is carried out using dNTPs at unequal concentrations.

When a nucleotide analog is used to introduce mutations into at least one target nucleic acid molecule, this will generally involve two amplification steps. In the first amplification step, the nucleotide analog is incorporated into the target nucleic acid molecule (a mutation step). In the second amplification step, the nucleotide analog pairs with a natural nucleotide, thereby introducing a mutation into one strand of the target nucleic acid molecule (a recovery step). When the target nucleic acid molecule is further amplified, this mutation will be transmitted to both strands of the target nucleic acid molecule. Optionally, both the first (mutation) amplification step and the second (recovery) amplification step may be carried out using dNTPs at unequal concentrations. Optionally the dNTPs at unequal concentrations are different in the first (mutation) amplification step and the second (recovery) amplification step. For example, the dNTPs at unequal concentrations may comprise dTTP at a lower concentration than other dNTPs in the first (mutation) amplification step and the dNTPs at unequal concentrations may comprise dATP at a lower concentration than other dNTPs in the second (recovery) amplification step. The step of amplifying the at least one target nucleic acid molecule using a low bias DNA polymerase or steps that provide a mutated at least one target nucleic acid molecule may correspond to one or more "mutation steps". A further step of amplifying the at least one target nucleic acid molecule comprising nucleotide analogs in the absence of nucleotide analogs or a further step of amplifying the mutated at least one target nucleic acid molecule may correspond to one or more "recovery steps".

Optionally, the nucleotide analog is dPTP.

In an embodiment, dNTPs at unequal concentrations are used to alter the profile of mutations that are introduced. The dNTPs at unequal concentrations are used in methods comprising introducing mutations into at least one target nucleic acid molecule. Thus, the methods result in target nucleic acid molecules comprising mutations (such as the mutated target nucleic acid molecules described herein). The number of mutations, type of mutations, and position of each mutations that are introduced into a given target nucleic acid molecule by the methods may be referred to as the "profile of mutations" that is introduced. The term "type of mutation" is intended to refer to the nature of the mutation, i.e. is it a substitution mutation, an addition mutation or a deletion mutation, and if it is a substitution mutation what was the starting nucleotide and what was the starting nucleotide mutated to (e.g. an A to G mutation has an A starting nucleotide which is mutated to G)?

The user may determine the "profile of mutations" that is introduced by a given method by replicating a test target nucleic acid molecule, then subjecting some of the replicates to the methods comprising introducing mutations of the invention, but reserving some of the replicates (without mutating them). The user may then sequence the replicates that have been subjected to the methods comprising introducing mutations of the invention, and the reserved replicates. Finally, the user can align the sequences of the replicates that have been subjected to the methods comprising introducing mutations of the invention, and the reserved replicates to determine the number of mutations, type of mutations and position of each mutation that have been introduced. Alternatively, the user may use a test target nucleic acid molecule of known sequence. The user will then merely need to subject the test target nucleic acid molecule to the methods comprising introducing mutations of the invention, and then sequence the resultant mutated target nucleic acid molecule to see what profile of mutations has been introduced.

The user may wish to alter the mutation profile in a number of ways. For example, as discussed above, it is advantageous to be able to reduce mutation bias. Accordingly, in an embodiment, dNTPs at unequal concentrations are used to reduce bias in the profile of mutations that are introduced. In a further embodiment, the method is a method for introducing mutations in a low bias mutation profile.

The present application demonstrates that using dNTPs at unequal concentrations can be used to reduce bias in the profile of mutations that are introduced. For example, if a DNA polymerase (such as a low bias DNA polymerase described above) is used to mutate a target nucleic acid molecule, and introduces a higher number of G to A mutations compared to other mutations, the user can reduce the concentration of dATPs relative to other dNTPs, and this may decrease the frequency at which A nucleotides are incorporated in place of dGTPs and so decrease the number of G to A mutations.

Similarly, if a nucleotide analog is used when introducing mutations into a target nucleic acid molecule, altering the relative concentrations of the dNTPs can be used to alter the mutation profile. For example, dPTP can be used to introduce G to A, C to T, A to G and T to C mutations. As described in more detail above, dPTP can replace a T nucleotide or a C nucleotide, and depending on whether the dPTP is in its amino or imino form, it can subsequently pair with an A nucleotide or a G nucleotide. This leads to two scenarios. In the first scenario, the dPTP replaces T in (for example) the sense strand (mutation step), it can then pair with A (no mutation) or G (A to G mutation) in the antisense strand. If dPTP replaces T and pairs with G in the antisense strand, the mutant G will pair with a C to introduce a T to C mutation in a replicate of the sense strand (recovery step). Conversely, dPTP may replace T in the antisense strand, which may lead to an A to G mutation in the sense strand and a T to C mutation in a replicate of the antisense strand. In the second scenario, the dPTP replaces C in the (for example) sense strand, it can then pair with A (G to A mutation) or G (no mutation) in the antisense strand (mutation step). If dPTP replaces C and pairs with A in the antisense strand, the mutant A will pair with a T to introduce a C to T mutation in a replicate of the sense strand (recovery step). Conversely, dPTP may replace C in the antisense strand, which may lead to a G to A mutation in the sense strand and a C to T mutation in a replicate of the antisense strand.

The present application demonstrates that if the rate of G to A and C to T mutations is higher than the rate of A to G and T to C mutations, then reducing the concentration of dTTPs compared to the other dNTPs (and preferably compared to the concentration of dCTP) will encourage dPTP to be incorporated in place of dTTP, increasing the instances of the first scenario set out above relative to the second scenario, meaning that the A to G and T to C mutations introduced in the first scenario will be increased. Similarly, the present application demonstrates that if the level of dATPs is reduced during the recovery step, then the level of G to A and C to T mutations increases. This is because in scenario 2 above, if dATP is present at a lower concentration compared to the other dNTPs (and preferably compared to the concentration of dGTP), this will mean that dPTP that has incorporated in place of a C nucleotide will pair more frequently with G and fewer G to A or C to T mutations will be introduced. The two scenarios are set out in FIG. 6.

Even the low bias DNA polymerases disclosed herein introduce mutations into a target nucleic acid molecule with a small bias. The present application demonstrates that using unequal concentrations of dNTPs with a low bias DNA polymerase can virtually eliminate any mutation bias.

Based on the information provided in the present application, it is within the abilities of the skilled person to determine how altering the concentrations of various dNTPs will affect the mutation profile depending on whether a nucleotide analog is used, and if so which one. Accordingly, in some embodiments, the methods which use dNTPs at unequal concentrations comprise a step of identifying a dNTP whose level should be increased or decreased in order to reduce bias in the profile of mutations that are introduced.

Optionally, the dNTPs at unequal concentrations comprise dTTP at a lower concentration than other dNTPs. As described above, this can increase the rate of T to C and A to G mutations that are introduced when dPTP is used as a nucleotide analog. Optionally, the dNTPs at unequal concentrations comprise dTTP at a concentration less than 75%, less than 70%, less than 60%, less than 55%, between 25% and 75%, between 25% and 70, between 25% and 60%, or around 50% of the concentration of dATP, dCTP or dGTP. Optionally, the dNTPs at unequal concentrations comprise dTTP at a concentration less than 60% of the concentration of dCTP. Optionally, the dNTPs at unequal concentrations comprise dTTP at a concentration between 25% and 60% of the concentration of dCTP.

Optionally, the dNTPs at unequal concentrations comprises dATP at a lower concentration compared to other dNTPs. As described above, this can decrease the rate of G to A or C to T mutations that are introduced when dPTP is used as a nucleotide analog. Optionally, the dNTPs at unequal concentrations comprises dATP at a concentration less than 75%, less than 70%, less than 60%, less than 55%, between 25% and 75%, between 25% and 70, between 25% and 60%, or around 50% of the concentration of dTTP, dCTP or dGTP. Optionally, the dNTPs at unequal concentrations comprises dATP at a concentration less than 75%, less than 70%, less than 60%, less than 55%, between 25% and 75%, between 25% and 70, between 25% and 60%, or around 50% of the concentration of dGTP. Optionally, the dNTPs at unequal concentrations comprises dATP at a concentration less than 60% of the concentration of dGTP. Optionally, the dNTPs at unequal concentrations dNTPs comprises dATP at a concentration between 25% and 60% of the concentration of dGTP.

As set out in the two scenarios above, when using dPTP as a nucleotide analog, reducing dTTPs increases T to C and A to G mutations by encouraging the replacement of T nucleotides in the target nucleic acid molecule with dPTP. Thus, dNTPs at unequal concentrations which comprise dTTP at a lower concentration than other dNTPs are preferably used in a mutagenesis step (for example a step of PCR in the presence of dPTPs). Similarly, when using dPTP as a nucleotide analog, reducing dATPs reduces the number of dPTPs that have replaced C nucleotides and pair with dATP and so increases G to A and C to T mutations. Since dPTP pairing with dATP tends to occur during a recovery step, reducing dATPs during the recovery step increases the number of G to A and C to T mutations. Optionally, therefore, the step of amplifying the at least one target nucleic acid molecule comprising nucleotide analogs in the absence of nucleotide analogs or amplifying the mutated at least one target nucleic acid molecule in the absence of the nucleotide analog is carried out using dNTPs at unequal concentrations, and the dNTPs at unequal concentrations comprises dATP at a lower concentration compared to other dNTPs.

EXAMPLES

Example 1—Mutating Nucleic Acid Molecules Using PrimeStar GXL of Other Polymerases DNA molecules were fragmented to the appropriate size (e.g. 10 kb) and a defined sequence priming site (adapter) was attached on each end using tagmentation.

The first step is a tagmentation reaction to fragment the DNA. 50 ng high molecular weight genomic DNA in 4 µl or less volume of one or more bacterial strains was subjected to tagmentation under the following conditions. 50 ng DNA is combined with 4 µl Nextera Transposase (diluted to 1:50), and 8 µl 2× tagmentation buffer (20 mM Tris [pH7.6], 20 mM MgCl, 20% (v/v) dimethylformamide) in a total volume of 16 µl. The reaction was incubated at 55° C. for 5 minutes, 4 µl of NT buffer (or 0.2% SDS) was added to the reaction and the reaction was incubated at room temperature for 5 minutes.

The tagmentation reaction was cleaned using SPRIselect beads (Beckman Coulter) following the manufacturer's instructions for a left side size selection using 0.6 volume of beads, and the DNA was eluted in molecular grade water.

This was followed by PCR with a combination of standard dNTPs and dPTP for a limited 6 cycles. Using Primestar GXL, 12.5 ng of tagmented and purified DNA was added to a total reaction volume of 25 µl, containing 1×GXL buffer, 200 M each of dATP, dTTP, dGTP and dCTP, as well as 0.5 mM dPTP, and 0.4 M custom primers (Table 2).

TABLE 2

Custom primers used for mutagenesis PCR on 10 kbp templates.
XXXXXX is a defined, sample-specific 6-8 nt barcode sequence.
NNNNNN is a 6 nt region of random nucleotides.

| i7 custom index primer (SEQ ID NO: 137) | CAAGCAGAAGACGGCA TACGAGAT | NNN NNN | XXX XXX | GTCTCGTGG GCTCGG |
|---|---|---|---|---|
| i5 custom index primer (SEQ ID NO: 138) | AATGATACGGCGACCA CCGAGATCTACAC | XXX XXX | NNN NNN | TCGTCGGCA GCGTC | random nucleotides.

The reaction was subject to the following thermal cycling in the presence of Primestar GXL. Initial gap extension at 68° C. for 3 minutes, followed by 6 cycles of 98° C. for 10 seconds, 55° C. for 15 seconds and 68° C. for 10 minutes.

The next stage is a PCR without dPTP, to remove dPTP from the templates and replace them with a transition mutation ("recovery PCR"). PCR reactions were cleaned with SPRIselect beads to remove excess dPTP and primers, then subjected to a further 10 rounds (minimum 1 round, maximum 20) of amplification using primers that anneal to the fragment ends introduced during the dPTP incorporation cycles (Table 3).

TABLE 3

| i7 flow cell primer (SEQ ID NO: 139) | CAAGCAGAAGAC GGCATACGA |
|---|---|

TABLE 3-continued

| i5 flow cell primer (SEQ ID NO: 140) | AATGATACGGCG ACCACCGA |
|---|---|

This was followed by a gel extraction step to size select amplified and mutated fragments in a desired size range, for example from 7-10 kb. The gel extraction can be done manually or via an automated system such as a BluePippin. This was followed by an additional round of PCR for 16-20 cycles ("enrichment PCR").

After amplifying a defined number of long mutated templates, random fragmentation of the templates was carried out to generate a group of overlapping shorter fragments for sequencing. Fragmentation was performed by tagmentation.

Long DNA fragments from the previous step were subject to a standard tagmentation reaction (e.g. Nextera XT or Nextera Flex), except that the reaction was split into three pools for the PCR amplification. This enables selective amplification of fragments derived from each end of the original template (including the sample barcode) as well as internal fragments from the long template that have been newly tagmented at both ends. This effectively creates three pools for sequencing on an Illumina instrument (e.g. MiSeq or HiSeq).

The method was repeated using a standard Taq (Jena Biosciences) and a blend of Taq and a proofreading polymerase (DeepVent) called LongAmp (New England Biolabs).

The data obtained from this experiment is depicted in FIG. 1. No dPTP was used a control. Reads were mapped against the *E. coli* genome, and a median mutation rate of ~8% was achieved.

Example 2—Comparison of Mutation Frequencies of Different DNA Polymerases

Mutagenesis was performed with a range of different DNA polymerases (Table 4). Genomic DNA from *E. coli* strain MG1655 was tagmented to produce long fragments and bead cleaned as described in the method of Example 1. This was followed by "mutagenesis PCR" for 6 cycles in the presence of 0.5 mM dPTP, SPRIselect bead purification and an additional 14-16 cycles of "recovery PCR" in the absence of dPTP. The resulting long mutated templates were then subjected to a standard tagmentation reaction (see Example 1) and "internal" fragments were amplified and sequenced on an Illumina MiSeq instrument.

The mutation rates are described in Table 4, which normalized frequencies of base substitution via dPTP mutagenesis reactions as measured using Illumina sequencing of DNA from the known reference genome. For Taq polymerase, only ~12% of mutations occur at template G+C sites, even when used in buffer optimised for *Thermococcus* polymerases. *Thermococcus*-like polymerases result in 58-69% of mutations at template G+C sites, while polymerase derived from *Pyrococcus* gives 88% of mutations at template G+C sites.

Enzymes were obtained from Jena Biosciences (Taq), Takara (Primestar variants), Merck Millipore (KOD DNA Polymerase) and New England Biolabs (Phusion).

Taq was tested with the supplied buffer, and also with Primestar GXL Buffer (Takara) for this experiment. All other reactions were carried out with the standard supplied buffer for each polymerase.

TABLE 4

| Polymerase[1] | Origin | Mutation frequency (% of total observed mutations) | | | | |
|---|---|---|---|---|---|---|
| | | A→G | T→C | G→A | C→T | Other (transversion) |
| Taq (standard buffer) | *Thermus aquaticus* | 43.1 | 41.7 | 6.3 | 6.1 | 2.7 |
| Taq (*Thermococcus* buffer[2]) | *Thermus aquaticus* | 48.9 | 47.5 | 2.9 | 0.7 | 0.0 |
| Prime star GXL | *Thermococcus* | 21.5 | 20.1 | 29.5 | 28.9 | 0.0 |
| Prime star HS | *Thermococcus* | 16.3 | 15.2 | 30.1 | 38.4 | 0.0 |
| Primestar Max | *Thermococcus* | 16.5 | 14.6 | 33.2 | 35.7 | 0.0 |
| KOD DNA polymerase | *Thermococcus* | 20.5 | 16.1 | 31.8 | 31.5 | 0.0 |
| Phusion | *Pyrococcus* | 5.4 | 6.4 | 44.1 | 44.1 | 0.0 |

Example 3—Determining dPTP Mutagenesis Rates

Figure 2:
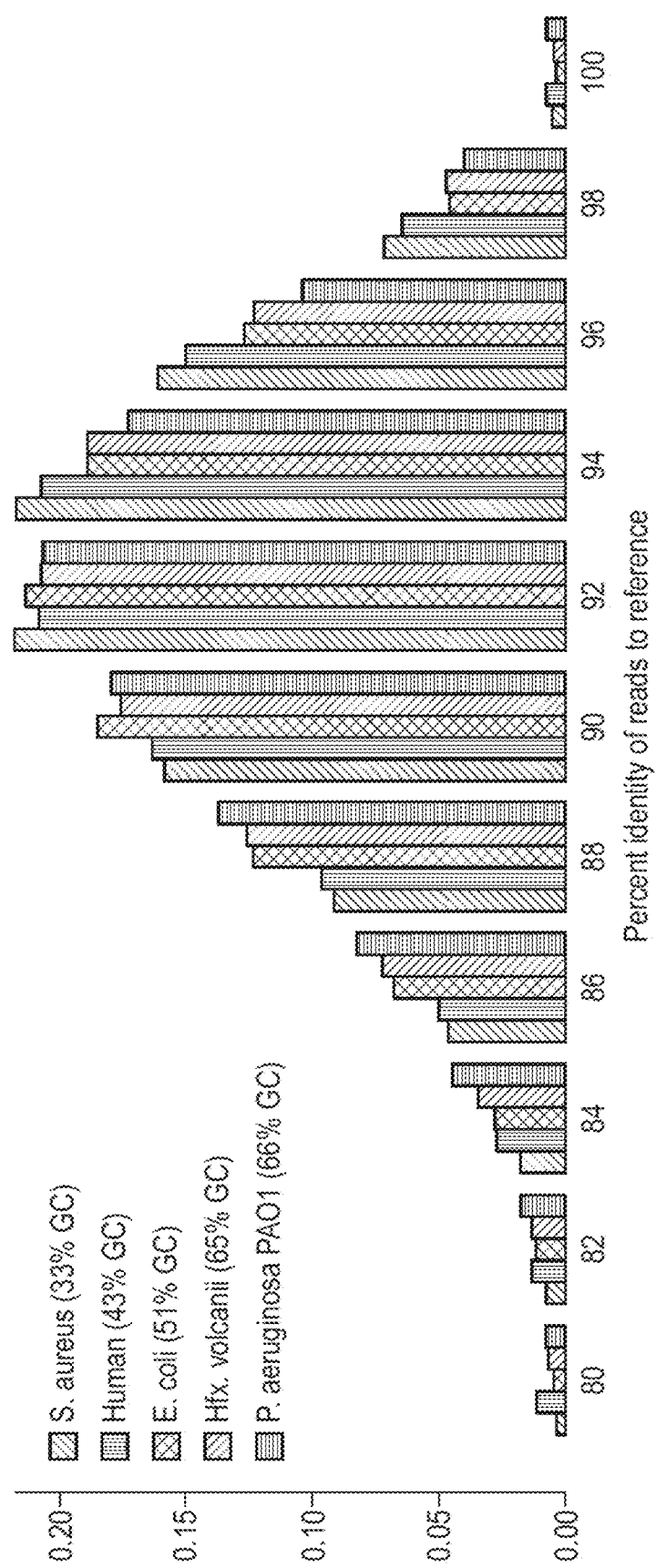
FIG. 2 describes the mutation rates obtained obtained by dPTP mutagenesis using a *Thermococcus* polymerase (Primestar GXL; Takara) on templates with diverse G+C content. The median observed rate of mutations was ~7% for low GC templates from *S. aureus* (33% GC), while the median for other templates was about 8%.

We performed dPTP mutagenesis on a range of genomic DNA samples with different levels of G+C content (33-66%) using a *Thermococcus* polymerase (Primestar GXL; Takara) under a single set of reaction conditions. Mutagenesis and sequencing was performed as described in the method of example 3, except that 10 cycles of "recovery PCR" were performed. As predicted, mutation rates were roughly similar between samples (median rate 7-8%) despite the diversity of G+C content (FIG. 2).

Example 4—Measuring Template Amplification Bias

Template amplification bias was measured for two polymerases: Kapa HiFi, which is a proofreading polymerase commonly used in Illumina sequencing protocols, and PrimeStar GXL, which is a KOD family polymerase known for its ability to amplify long fragments. In the first experiment Kapa HiFi was used to amplify a limited number of *E. coli* genomic DNA templates with sizes around 2 kbp. The ends of these amplified fragments were then sequenced. A similar experiment was done with PrimeStar GXL on fragments around 7-10 kbp from *E. coli*. The positions of each end sequence read were determined by mapping to the *E. coli* reference genome. The distances between neighboring fragment ends was measured. These distances were compared to a set of distances randomly sampled from the uniform distribution. The comparison was carried out via the nonparametric Kolmolgorov-Smirnov test, D. When two samples come from the same distribution, the value of D approaches zero. For the low bias PrimeStar polymerase, we observed D=0.07 when measured on 50,000 fragment ends, compared to a uniform random sample of 50,000 genomic positions. For the Kapa HiFi polymerase we observed D=0.14 on 50,000 fragment ends.

Example 5—Using Two Identical Primer Binding Sites and a Single Primer Sequence for Preferential Amplification of Longer Templates As described above, tagmentation can be used to fragment DNA molecules and simultaneously introduce primer binding sites (adapters) onto the ends of the fragments. The Nextera tagmentation system (Illumina) utilises transposase enzymes loaded with one of two unique adapters (referred to here as X and Y). This generates a random mixture of products, some with identical end sequences (X-X, Y-Y) and some with unique ends (X-Y). Standard Nextera protocols use two distinct primer sequences to selectively amplify "X-Y" products containing different adapters on each end (as required for sequencing with Illumina technology). However, it is also possible to use a single primer sequence to amplify "X-X" or "Y-Y" fragments with identical end adapters.

To generate long mutated templates containing identical end adapters, 50 ng of high molecular weight genomic DNA (*E. coli* strain MG1655) was first subjected to tagmentation and then cleaned with SPRIselect beads as described in Example 1. This was followed by 5 cycles of "mutagenesis PCR" with a combination of standard dNTPs and dPTP, which was performed as detailed in Example 1 except that a single primer sequence was used (Table 5).

The PCR reaction was cleaned with SPRIselect beads to remove excess dPTP and primers, then subjected to a further 10 cycles of "recovery PCR" in the absence of dPTP to replace dPTP in the templates with transition mutations. Recovery PCR was performed with a single primer that anneals to the fragment ends introduced during the dPTP incorporation cycles, thereby enabling selective amplification of mutated templates generated in the previous PCR step.

TABLE 5

| Primer name | Step | Sequence | | | |
|---|---|---|---|---|---|
| single_mut (SEQ ID NO: 141) | mutagenesis | TCGGTCTGCGCC TCTAGC | NNN | XXXXXX XXXXXX X | GTCTCGTG GGCTCGG AG |

TABLE 5-continued

| Primer name | Step | Sequence |
|---|---|---|
| single_rec (SEQ ID NO: 142) | recovery | CAAGCAGAAGA CGGCATACGAG AT TCGGTCTGCGCCTCTAGC |

Primers used to generate mutated templates with the same basic adapter structure on both ends. Primer "single_mut" was used for mutagenesis PCR on DNA fragments generated by Nextera tagmentation. This primer contains a 5' portion that introduces an additional primer binding site at the fragment ends. Primer "single_rec" is capable of annealing to this site, and was used during recovery PCR to selectively amplify mutated templates generated with the single_mut primer. XXXXXXXXXXXXX is a defined, sample-specific 13 nt barcode sequence. NNN is a 3 nt region of random nucleotides.

As a control, mutated templates with different adapters on each end were generated using an identical protocol to that described above, except that two distinct primer sequences were used during both mutagenesis PCR (shown in Table 2) and recovery PCR (Table 3). Final PCR products were cleaned with SPRIselect beads and analysed on a High Sensitivity DNA Chip using the 2100 Bioanalzyer System (Agilent). The templates generated with identical end adapters were significantly longer on average than the control sample containing dual adapters. Control templates could be detected down to a minimum size of ~800 bp, while no templates below 2000 bp were observed for the single adapter sample.

Figure 5:
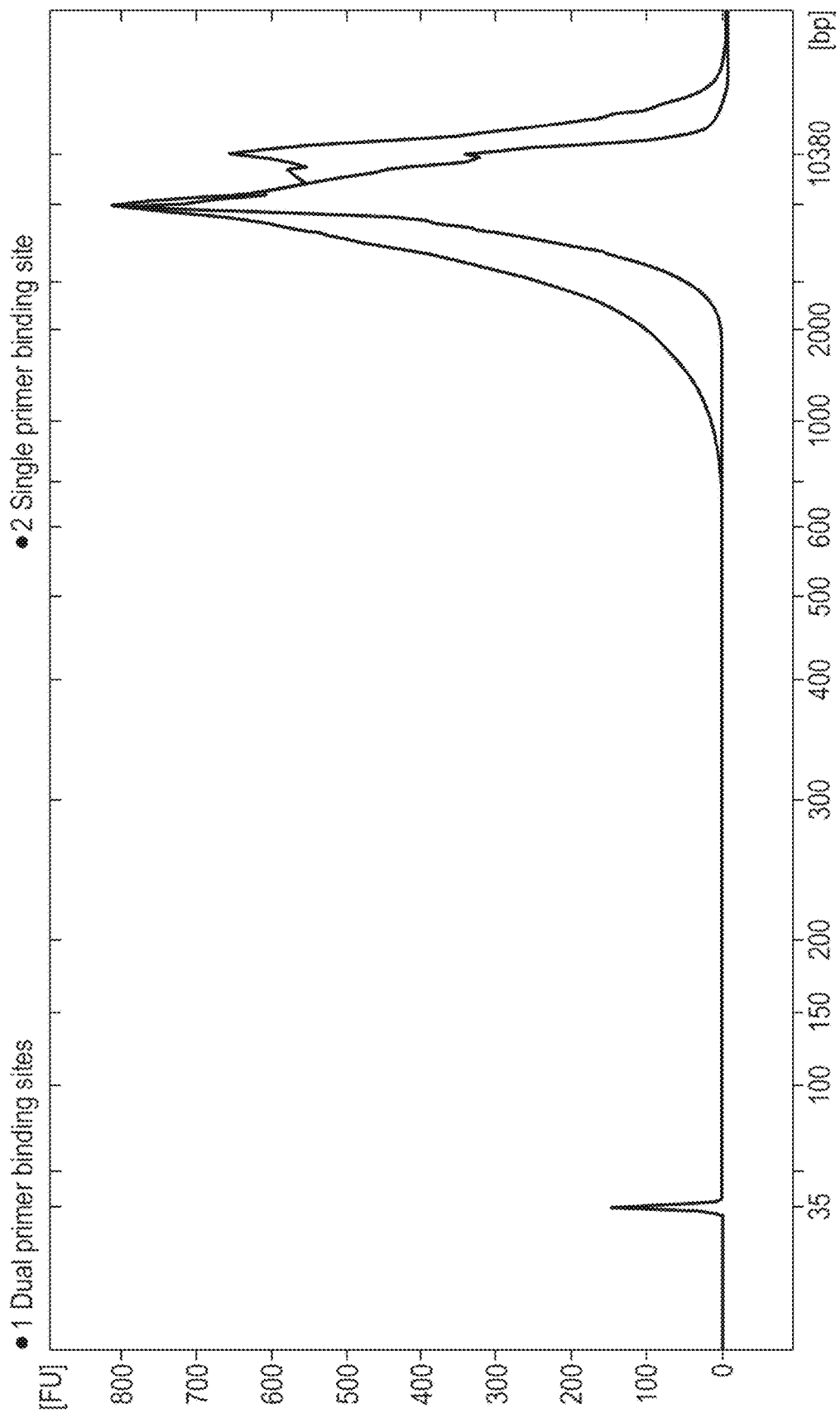
FIG. 5 depicts the sizes of target nucleic acid molecules amplified using adapters that anneal to one another (right line) or using standard adapters (left line).

Mutated templates with identical end adapters (blue) and control templates with dual adapters were run on an Agilent 2100 Bioanalyzer (High Sensitivity DNA Kit) to compare size profiles. The use of identical end adapters inhibits the amplification of templates <2 kbp. The data is presented in FIG. 5.

Example 8—Further Reducing the Mutation Bias of *Thermococcus* Polymerases by Altering Natural dNTP Levels During PCR Although *Thermococcus* polymerases generate a much more balanced mutation profile compared to other DNA polymerases, they do exhibit a small amount of bias towards mutations at G and C sites (see Table 4). To eliminate this residual bias, we tested the effect of altering the concentrations of natural dNTPs during the mutagenesis and recovery PCR steps to influence the relative incorporation rates of the different nucleotides.

First, long mutated templates were prepared from bacterial genomic DNA (*E. coli* strain MG1655) using the approach outlined in Example 5, except that the concentration of individual nucleotides in the PCR reactions were varied. This was achieved by adding individual solutions of the four natural nucleotides (purchased from New England Biolabs) separately to the PCR mixture, either at a standard final concentration of 200 M or at a lower concentration of 160 M (80% relative to standard) or 100 M (50%). Only one nucleotide was varied per reaction. As a control, all natural nucleotides were added to the same final concentration of 200 M, using an equimolar dNTP mixture provided with the Primestar GXL polymerase (Takara). Five mutagenesis PCR cycles and twelve recovery cycles were performed using primers shown in Table 5. The resulting long mutated templates were then subjected to a standard tagmentation reaction (see Example 1) and "internal" fragments were amplified and sequenced on an Illumina MiSeq instrument. Mutation frequencies were determined by comparison against the known reference sequence.

As shown in Table 6 changes in the concentration of individual dNTPs during mutagenesis and/or recovery PCR altered the observed profile of mutations. Importantly, limiting the amount of dTTP by 50% during mutagenesis was found to produce virtually identical mutation frequencies for each nucleotide (Table 3). This confirms that the residual mutation bias of *Thermococcus* polymerases can be eliminated through changes in dNTP levels.

TABLE 6

| Treatment | Mutation frequency (% of total observed mutations) | | | |
|---|---|---|---|---|
| | A → G | T → C | G → A | C → T |
| Equimolar dNTP control | 17.4 | 16.8 | 32.1 | 33.7 |
| 80% dTTP (mutagenesis) | 13.9 | 13.8 | 36.1 | 36.2 |
| 50% dTTP (mutagenesis) | 23.7 | 24.9 | 25.3 | 26.2 |
| 80% dATP (recovery) | 13.4 | 12.5 | 36.7 | 37.3 |
| 50% dATP (recovery) | 18.9 | 19.1 | 31.4 | 30.6 |
| 80% dTTP (mutagenesis) and 80% dATP (recovery) | 17.8 | 15.0 | 34.0 | 33.2 |
| 50% dTTP (mutagenesis) and 50% dATP (recovery) | 34.4 | 34.7 | 15.4 | 15.5 |

What is claimed is:

1. A method for determining a sequence of at least one target nucleic acid molecule, the method comprising:

a. providing at least one sample comprising at least one target nucleic acid molecule;

b. introducing mutations into the at least one target nucleic acid molecule, wherein introducing mutations comprises amplifying the at least one target nucleic acid molecule for 2 to 20 rounds using a high-fidelity low-bias DNA polymerase, unequal concentrations of dNTPs, and a nucleotide analog, to provide a mutated at least one target nucleic acid molecule;

c. amplifying and fragmenting the mutated at least one target nucleic acid molecule;

d. sequencing regions of the mutated at least one target nucleic acid molecule to provide mutated sequence reads; and e. assembling a sequence for at least a portion of the at least one target nucleic acid molecule using the mutated sequence reads.

2. The method of claim 1, wherein the dNTPs at unequal concentrations comprise dATP, dCTP, dTTP and dGTP and one or two of dATP, dCTP, dTTP or dGTP are at a lower concentration compared to other dNTPs.

3. The method of claim 2, wherein the dNTPs at unequal concentrations comprise dTTP at a lower concentration than other dNTPs.

4. The method of claim 3, wherein the dNTPs at unequal concentrations comprise dATP at a lower concentration compared to other dNTPs.

5. The method of claim 1, wherein the method further comprises a step of identifying a dNTP whose level should be increased or decreased in order to reduce bias in the profile of mutations that are introduced.

6. The method of claim 1, wherein the low bias DNA polymerase has a low template amplification bias.

7. The method of claim 1, wherein the DNA polymerase mutates adenine, thymine, guanine, and cytosine nucleotides in the at least one target molecule at a rate ratio of 0.5-1.5: 0.5-1.5:0.5-1.5:0.5-1.5 respectively.

8. The method of claim 1, wherein the DNA polymerase mutates between 1% and 15% of the nucleotides in the at least one target DNA molecule or wherein the DNA polymerase mutates between 0% and 3%, or 2% of the nucleotides in the at least one target DNA molecule per round of replication.

9. The method of claim 1, wherein the DNA polymerase introduces guanine or adenine nucleotides using a nucleotide analog at a rate ratio of 0.5-1.5:0.5-1.5, respectively, or wherein the DNA polymerase introduces guanine or adenine nucleotides using a nucleotide analog at a rate ratio of 0.7-1.3:0.7-1.3 respectively.

10. The method of claim 1, wherein the DNA polymerase mutates between 1% and 15% of the nucleotides in the at least one target DNA molecule, or wherein the DNA polymerase mutates between 0% and 3%, of 2% of the nucleotides in the at least one target DNA molecule per round of replication.

11. The method of claim 1, wherein the nucleotide analog is dPTP.

12. The method of claim 1, wherein the DNA polymerase comprises a proof-reading domain or a processivity enhancing domain, or
    wherein the DNA polymerase comprises a fragment of at least 400 contiguous amino acids of:
    a. a sequence of SEQ ID NO. 2;
    b. a sequence at least 95% identical to SEQ ID NO. 2;
    c. a sequence of SEQ ID NO. 4;
    d. a sequence at least 95% identical to SEQ ID NO. 4;
    e. a sequence of SEQ ID NO. 6;
    f. a sequence at least 95% identical to SEQ ID NO. 6;
    g. a sequence of SEQ ID NO. 7; or
    h. a sequence at least 95% identical to SEQ ID NO. 7.

13. The method of claim 12, wherein the low bias DNA polymerase is a thermococcal polymerase, or derivative thereof.

14. The method of claim 1,
    wherein the DNA polymerase comprises:
    a. a sequence of SEQ ID NO. 2;
    b. a sequence at least 95% identical to SEQ ID NO. 2;
    c. a sequence of SEQ ID NO. 4;
    d. a sequence at least 95% identical to SEQ ID NO. 4;
    e. a sequence of SEQ ID NO. 6;
    f. a sequence at least 95% identical to SEQ ID NO. 6;
    g. a sequence of SEQ ID NO. 7; or
    h. a sequence at least 95% identical to SEQ ID NO. 7.

15. The method of claim 1, wherein:
    i) the DNA polymerase comprises a sequence at least 98% identical to SEQ ID NO. 2;
    ii) the DNA polymerase comprises a sequence at least 98% identical to SEQ ID NO. 4;
    iii) the DNA polymerase comprises a sequence at least 98% identical to SEQ ID NO. 6; or
    iv) the DNA polymerase comprises a sequence at least 98% identical to SEQ ID NO. 7.

16. The method of claim 1, wherein the low bias DNA polymerase is a thermococcal polymerase, or derivative thereof.

17. The method of claim 1, wherein the at least one target nucleic acid molecule is greater than 1 kbp.

18. The method of claim 1, wherein the DNA polymerase introduces guanine to adenine substitution mutations, cytosine to thymine substitution mutations, adenine to guanine substitution mutations, and thymine to cytosine substitution mutations.

19. The method of claim 1, wherein the DNA polymerase introduces guanine to adenine substitution mutations, cytosine to thymine substitution mutations, adenine to guanine substitution mutations, and thymine to cytosine substitution mutations at a rate ratio of 0.5-1.5:0.5-1.5:0.5-1.5:0.5-1.5, respectively.

20. The method of claim 1, wherein the DNA polymerase introduces guanine to adenine substitution mutations, cytosine to thymine substitution mutations, adenine to guanine substitution mutations, and thymine to cytosine substitution mutations at a rate ratio of 0.7-1.3:0.7-1.3:0.7-1.3:0.7-1.3 respectively.

21. The method of claim 16, wherein the thermococcal polymerase is derived from a thermococcal strain selected from the group consisting of *T. kodakarensis, T. siculi, T. celer* and *T. sp* KS-1.

22. The method of claim 3, wherein the dNTPs at unequal concentrations comprise dTTP at a concentration less than 75% of the concentration of dATP, dCTP or dGTP.

23. The method of claim 3, wherein the dNTPs at unequal concentrations comprise dTTP at a concentration less than 75% of the concentration of dCTP.

24. The method of claim 3, wherein the dNTPs at unequal concentrations comprise dTTP at a concentration less than 60% of the concentration of dCTP.

25. The method of claim 3, wherein the dNTPs at unequal concentrations comprise dTTP at a concentration between 25% and 60% of the concentration of dCTP.

26. The method of claim 4, wherein the dNTPs at unequal concentrations comprise dATP at a concentration less than 75% of the concentration of dTTP, dCTP or dGTP.

27. The method of claim 4, wherein the dNTPs at unequal concentrations of dNTPs comprise dATP at a concentration less than 75% of the concentration of dGTP.

28. The method of claim 4, wherein the dNTPs at unequal concentrations comprise dATP at a concentration less than 60% of the concentration of dGTP.

29. The method of claim 4, wherein the dNTPs at unequal concentrations comprise dATP at a concentration between 25% and 60% of the concentration of dGTP.

* * * * *

SEQUENCE LISTING

<160> NUMBER OF SEQ ID NOS: 142

<210> SEQ ID NO 1
<211> LENGTH: 2325
<212> TYPE: DNA
<213> ORGANISM: Artificial Sequence
<220> FEATURE:
<223> OTHER INFORMATION: DNA polymerase from Thermococcus sp. KS-1

<400> SEQUENCE: 1

```
atgatcctcg acactgacta cataactgag aatggaaaac ccgtcataag gatttttcaag    60
aaggagaacg gcgagtttaa gattgagtac gataggactt ttgaaccccta catttacgcc   120
ctcctgaagg acgattctgc cattgaggag gtcaagaaga taaccgccga gaggcacgga   180
acggttgtaa cggttaagcg ggctgaaaag gttcagaaga agttcctcgg gagaccagtt   240
gaggtctgga aactctactt tactcaccct caggacgtcc cagcgataag ggacaagata   300
cgagagcatc cagcagttat tgacatctac gagtacgaca tacccttcgc caagcgctac   360
ctcatagaca agggattagt gccaatggaa ggcgacgagg agctgaaaat gcttgccttt   420
gatatcgaga cgctctacca tgagggcgag gagttcgccg aggggccaat ccttatgata   480
agctacgccg acgaggaagg ggccagggtg ataacgtgga agaacgcgga tctgccctac   540
gttgacgtcg tctcgacgga gagggagatg ataaagcgct tcctaaaggt ggtcaaagag   600
aaagatcctg acgtcctaat aacctacaac ggcgacaact tcgacttcgc ctacctaaaa   660
aaacgctgtg aaaagcttgg aataaacttc acgctcggaa gggacggaag cgagccgaag   720
attcagagga tgggcgacag gtttgccgtc gaagtgaagg gacggataca cttcgatctc   780
tatcctgtga taagacggac gataaacctg cccacataca cgcttgaggc cgtttatgaa   840
gccgtcttcg gtcagccgaa ggagaaggtc tacgctgagg agatagctac agcttgggag   900
agcggtgaag gccttgagag agtagccaga tactcgatgg aagatgcgaa ggtcacatac   960
gagcttggga aggagttttt ccctatggag gcccagcttt ctcgcttaat cggccagtcc  1020
ctctgggacg tctcccgctc cagcactggc aacctcgttg agtggttcct cctcaggaag  1080
gcctacgaga ggaatgagct ggccccgaac aagcccgatg aaaaggagct ggccagaaga  1140
cgacagagct atgaaggagg ctatgtaaaa gagcccgaga gagggttgtg ggagaacata  1200
gtgtacctag atttagatc tctgtacccc tcaatcatca tcacccacaa cgtctcgccg  1260
gatactctca acagggaagg atgcaaggaa tatgacgttg cccccccaggt cggtcaccgc  1320
ttctgcaagg acttcccagg atttatcccg agcctgcttg gagacctcct agaggagagg  1380
cagaagataa agaagaagat gaaggccacg attgacccga tcgagaggaa gctcctcgat  1440
tacaggcaga gggccatcaa gatcctggcc aacagctact acggttacta cggctatgca  1500
agggcgcgct ggtactgcaa ggagtgtgca gagagcgtaa cggcctgggg aagggagtac  1560
ataacgatga ccatcagaga gatagaggaa aagtacggct ttaaggtaat ctacagcgac  1620
accgacggat tttttgccac aatacctgga gccgatgctg aaaccgtcaa aaagaaggcg  1680
atggagttcc tcaagtatat caacgccaaa ctcccgggcg cgcttgagct cgagtacgag  1740
ggcttctaca acgcggctt cttcgtcacg aagaagaagt acgcggtgat agacgaggaa  1800
ggcaagataa caacgcgcgg acttgagatt gtgaggcgcg actggagcga gatagcgaaa  1860
gagacgcagg cgagggttct tgaagctttg ctaaaggacg gtgacgtcga aaggccgtg  1920
aggatagtca agaagttac cgaaaagctg agcaagtacg aggttccgcc ggagaagctg  1980
gtgatccacg agcagataac gagggattta aaggactaca aggcaaccgg tccccacgtt  2040
gccgttgcca agaggttggc cgcgagagga gtcaaaatac gccctggaac ggtgataagc  2100
tacatcgtgc tcaagggctc tgggaggata ggcgacaggg cgataccgtt cgacgagttc  2160
gacccgacga agcacaagta cgacgccgag tactacattg agaaccaggt tctcccagcc  2220
gttgagagaa ttctgagagc cttcggttac cgcaaggaag acctgcgcta ccagaagacg  2280
agacaggttg gtctgggagc ctggctgaag ccgaagggaa cttga             2325
```

<210> SEQ ID NO 2
<211> LENGTH: 774
<212> TYPE: PRT
<213> ORGANISM: Artificial Sequence
<220> FEATURE:
<223> OTHER INFORMATION: DNA polymerase from Thermococcus sp. KS-1

<400> SEQUENCE: 2

| Met | Ile | Leu | Asp | Thr | Asp | Tyr | Ile | Thr | Glu | Asn | Gly | Lys | Pro | Val | Ile |
|---|---|---|---|---|---|---|---|---|---|---|---|---|---|---|---|
| 1 | | | | 5 | | | | | 10 | | | | | 15 | |

| Arg | Ile | Phe | Lys | Lys | Glu | Asn | Gly | Glu | Phe | Lys | Ile | Glu | Tyr | Asp | Arg |
|---|---|---|---|---|---|---|---|---|---|---|---|---|---|---|---|
| | | | 20 | | | | | 25 | | | | | 30 | | |

| Thr | Phe | Glu | Pro | Tyr | Ile | Tyr | Ala | Leu | Leu | Lys | Asp | Asp | Ser | Ala | Ile |
|---|---|---|---|---|---|---|---|---|---|---|---|---|---|---|---|
| | | 35 | | | | | 40 | | | | | 45 | | | |

| Glu | Glu | Val | Lys | Lys | Ile | Thr | Ala | Glu | Arg | His | Gly | Thr | Val | Val | Thr |
|---|---|---|---|---|---|---|---|---|---|---|---|---|---|---|---|
| | 50 | | | | | 55 | | | | | 60 | | | | |

| Val | Lys | Arg | Ala | Glu | Lys | Val | Gln | Lys | Lys | Phe | Leu | Gly | Arg | Pro | Val |
|---|---|---|---|---|---|---|---|---|---|---|---|---|---|---|---|
| 65 | | | | | 70 | | | | | 75 | | | | | 80 |

| Glu | Val | Trp | Lys | Leu | Tyr | Phe | Thr | His | Pro | Gln | Asp | Val | Pro | Ala | Ile |
|---|---|---|---|---|---|---|---|---|---|---|---|---|---|---|---|
| | | | | 85 | | | | | 90 | | | | | 95 | |

| Arg | Asp | Lys | Ile | Arg | Glu | His | Pro | Ala | Val | Ile | Asp | Ile | Tyr | Glu | Tyr |
|---|---|---|---|---|---|---|---|---|---|---|---|---|---|---|---|
| | | | 100 | | | | | 105 | | | | | 110 | | |

| Asp | Ile | Pro | Phe | Ala | Lys | Arg | Tyr | Leu | Ile | Asp | Lys | Gly | Leu | Val | Pro |
|---|---|---|---|---|---|---|---|---|---|---|---|---|---|---|---|
| | | 115 | | | | | 120 | | | | | 125 | | | |

| Met | Glu | Gly | Asp | Glu | Glu | Leu | Lys | Met | Leu | Ala | Phe | Asp | Ile | Glu | Thr |
|---|---|---|---|---|---|---|---|---|---|---|---|---|---|---|---|
| | 130 | | | | | 135 | | | | | 140 | | | | |

| Leu | Tyr | His | Glu | Gly | Glu | Glu | Phe | Ala | Glu | Gly | Pro | Ile | Leu | Met | Ile |
|---|---|---|---|---|---|---|---|---|---|---|---|---|---|---|---|
| 145 | | | | | 150 | | | | | 155 | | | | | 160 |

| Ser | Tyr | Ala | Asp | Glu | Glu | Gly | Ala | Arg | Val | Ile | Thr | Trp | Lys | Asn | Ala |
|---|---|---|---|---|---|---|---|---|---|---|---|---|---|---|---|
| | | | | 165 | | | | | 170 | | | | | 175 | |

| Asp | Leu | Pro | Tyr | Val | Asp | Val | Val | Ser | Thr | Glu | Arg | Glu | Met | Ile | Lys |
|---|---|---|---|---|---|---|---|---|---|---|---|---|---|---|---|
| | | | 180 | | | | | 185 | | | | | 190 | | |

| Arg | Phe | Leu | Lys | Val | Val | Lys | Glu | Lys | Asp | Pro | Asp | Val | Leu | Ile | Thr |
|---|---|---|---|---|---|---|---|---|---|---|---|---|---|---|---|
| | | 195 | | | | | 200 | | | | | 205 | | | |

| Tyr | Asn | Gly | Asp | Asn | Phe | Asp | Phe | Ala | Tyr | Leu | Lys | Lys | Arg | Cys | Glu |
|---|---|---|---|---|---|---|---|---|---|---|---|---|---|---|---|
| | 210 | | | | | 215 | | | | | 220 | | | | |

| Lys | Leu | Gly | Ile | Asn | Phe | Thr | Leu | Gly | Arg | Asp | Gly | Ser | Glu | Pro | Lys |
|---|---|---|---|---|---|---|---|---|---|---|---|---|---|---|---|
| 225 | | | | | 230 | | | | | 235 | | | | | 240 |

| Ile | Gln | Arg | Met | Gly | Asp | Arg | Phe | Ala | Val | Glu | Val | Lys | Gly | Arg | Ile |
|---|---|---|---|---|---|---|---|---|---|---|---|---|---|---|---|
| | | | | 245 | | | | | 250 | | | | | 255 | |

| His | Phe | Asp | Leu | Tyr | Pro | Val | Ile | Arg | Arg | Thr | Ile | Asn | Leu | Pro | Thr |
|---|---|---|---|---|---|---|---|---|---|---|---|---|---|---|---|
| | | | 260 | | | | | 265 | | | | | 270 | | |

| Tyr | Thr | Leu | Glu | Ala | Val | Tyr | Glu | Ala | Val | Phe | Gly | Gln | Pro | Lys | Glu |
|---|---|---|---|---|---|---|---|---|---|---|---|---|---|---|---|
| | | 275 | | | | | 280 | | | | | 285 | | | |

| Lys | Val | Tyr | Ala | Glu | Glu | Ile | Ala | Thr | Ala | Trp | Glu | Ser | Gly | Glu | Gly |
|---|---|---|---|---|---|---|---|---|---|---|---|---|---|---|---|
| | 290 | | | | | 295 | | | | | 300 | | | | |

| Leu | Glu | Arg | Val | Ala | Arg | Tyr | Ser | Met | Glu | Asp | Ala | Lys | Val | Thr | Tyr |
|---|---|---|---|---|---|---|---|---|---|---|---|---|---|---|---|
| 305 | | | | | 310 | | | | | 315 | | | | | 320 |

| Glu | Leu | Gly | Lys | Glu | Phe | Phe | Pro | Met | Glu | Ala | Gln | Leu | Ser | Arg | Leu |
|---|---|---|---|---|---|---|---|---|---|---|---|---|---|---|---|
| | | | | 325 | | | | | 330 | | | | | 335 | |

| Ile | Gly | Gln | Ser | Leu | Trp | Asp | Val | Ser | Arg | Ser | Ser | Thr | Gly | Asn | Leu |
|---|---|---|---|---|---|---|---|---|---|---|---|---|---|---|---|
| | | | 340 | | | | | 345 | | | | | 350 | | |

| Val | Glu | Trp | Phe | Leu | Leu | Arg | Lys | Ala | Tyr | Glu | Arg | Asn | Glu | Leu | Ala |
|---|---|---|---|---|---|---|---|---|---|---|---|---|---|---|---|
| | | 355 | | | | | 360 | | | | | 365 | | | |

| Pro | Asn | Lys | Pro | Asp | Glu | Lys | Glu | Leu | Ala | Arg | Arg | Arg | Gln | Ser | Tyr |
|---|---|---|---|---|---|---|---|---|---|---|---|---|---|---|---|

```
            370                 375                 380
Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
                435                 440                 445

Ile Pro Ser Leu Leu Gly Asp Leu Leu Glu Glu Arg Gln Lys Ile Lys
                450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
                500                 505                 510

Val Thr Ala Trp Gly Arg Glu Tyr Ile Thr Met Thr Ile Arg Glu Ile
                515                 520                 525

Glu Glu Lys Tyr Gly Phe Lys Val Ile Tyr Ser Asp Thr Asp Gly Phe
530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
                580                 585                 590

Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
                610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
                660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
                690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Arg Gln Val Gly Leu Gly Ala Trp
                755                 760                 765

Leu Lys Pro Lys Gly Thr
                770

<210> SEQ ID NO 3
```

<211> LENGTH: 2325
<212> TYPE: DNA
<213> ORGANISM: Artificial Sequence
<220> FEATURE:
<223> OTHER INFORMATION: DNA polymerase from Thermococcus celer

<400> SEQUENCE: 3

| | | | | | |
|---|---|---|---|---|---|
| atgatcctcg | acgctgacta | catcaccgaa | gatgggaagc | ccgtcgtgag | gatattcagg | 60 |
| aaggagaagg | gcgagttcag | aatcgactac | gacagggact | tcgagcccta | catctacgcc | 120 |
| ctcctgaagg | acgattcggc | catcgaggag | gtgaagagga | taaccgttga | gcgccacggg | 180 |
| aaggccgtca | gggttaagcg | ggtggagaag | gtcgaaaaga | agttcctcaa | caggccgata | 240 |
| gaggtctgga | agctctactt | caatcacccg | caggacgttc | cggcgataag | ggacgagata | 300 |
| aggaagcatc | cggccgtcgt | tgatatctac | gagtacgaca | tcccctccgc | caagcgctac | 360 |
| ctcatcgata | aggggctcgt | cccgatggag | ggggaggagg | agctcaaact | gatggccttc | 420 |
| gacatcgaga | ccctctacca | cgagggagac | gagttcgggg | aggggccgat | cctgatgata | 480 |
| agctacgccg | acgggacgg | ggcgagggtc | ataacctgga | agaagatcga | cctcccctac | 540 |
| gtcgacgtcg | tctcgaccga | gaaggagatg | ataaagcgct | tcctccaggt | ggtgaaggag | 600 |
| aaggacccgg | acgtgctcgt | aacttacaac | ggcgacaact | tcgacttcgc | ctacctgaag | 660 |
| agacgctccg | aggagcttgg | attgaagttc | atcctcggga | gggacgggag | cgagcccaag | 720 |
| atccagcgca | tgggcgaccg | cttcgccgtc | gaggtgaagg | gaaggataca | cttcgacctc | 780 |
| tacccggtga | taaggcgcac | cgtgaacctg | ccgacctaca | cgctcgaggc | ggtctacgag | 840 |
| gccatcttcg | ggaggccaaa | ggagaaggtc | tacgccgggg | agatagtgga | ggcctgggaa | 900 |
| accggcgagg | gtcttgagag | ggttgcccgc | tactccatgg | aggacgcaaa | ggttaccttc | 960 |
| gagctcggga | gggagttctt | cccgatggag | gcccagctct | cgaggctcat | cggccagggt | 1020 |
| ctctgggacg | tctcccgctc | gagcaccggc | aacctggtcg | agtggttcct | cctgaggaag | 1080 |
| gcctacgaga | ggaacgaact | ggccccgaac | aagccgagcg | ccgggaagt | ggagatcagg | 1140 |
| aggcgtggct | acgccggtgg | ttacgttaag | gagccggaga | ggggtttatg | ggagaacatc | 1200 |
| gtgtacctcg | actttcgctc | tctttacccc | tccatcatca | taaccacaa | cgtctcgccc | 1260 |
| gatacccta | acagggaggg | ctgtgagaac | tacgacgtcg | cccccaggt | ggggcataag | 1320 |
| ttctgcaaag | atttccgggg | cttcatcccg | agcctgctcg | gaggcctgct | tgaggagagg | 1380 |
| cagaagataa | agcggaggat | gaaggcctct | gtggatcccg | ttgagcggaa | gctcctcgat | 1440 |
| tacaggcaga | gggccatcaa | gatactggcc | aacagcttct | acggatacta | cggctacgcg | 1500 |
| agggcgaggt | ggtactgcag | ggagtgcgcg | gagagcgtta | ccgcctgggg | cagggagtac | 1560 |
| atcgataggg | tcatcaggga | gctcgaggag | aagttcggct | tcaaggtgct | ctacgcggac | 1620 |
| acggacggac | tgcacgccac | gatccccggg | gcggacgccg | ggaccgtcaa | ggagagggcg | 1680 |
| aggggggttcc | tgagatacat | caaccccaag | ctccccggcc | tcctggagct | cgagtacgag | 1740 |
| gggttctacc | tgagggtgttt | cttcgtgacg | aagaagaagt | acgcggtcat | agacgaggag | 1800 |
| ggcaagataa | ccacgcgcgg | cctcgagata | gtcaggcggg | actggagcga | ggtggccaag | 1860 |
| gagacgcagg | cgagggtcct | ggaggcgata | ctgaggcacg | gtgacgtcga | ggaggccgtt | 1920 |
| agaatcgtca | gggaggtaac | cgaaaagctg | agcaagtacg | aggttccgcc | ggagaaactg | 1980 |
| gtgatccacg | agcagataac | gagggatttg | aggactaca | aagccacggg | accgcacgtg | 2040 |
| gcggtggcga | agcgcctggc | cgggagggggg | gtaaggatac | gccccgggac | ggtgataagc | 2100 |
| tacatcgtcc | tcaagggctc | cggaaggata | ggggacaggg | cgattcccct | cgacgagttc | 2160 |

-continued

```
gacccgacta agcacaggta cgacgccgac tactacatcg agaaccaggt tctgccagcc    2220
gtcgagagga tcctgaaggc cttcggctac cgcaaggagg acctgaaata ccagaagacg    2280
aggcaggtgg gcctgggtgc gtggctcaac gcggggaagg ggtga                    2325
```

<210> SEQ ID NO 4
<211> LENGTH: 774
<212> TYPE: PRT
<213> ORGANISM: Artificial Sequence
<220> FEATURE:
<223> OTHER INFORMATION: DNA polymerase from Thermococcus celer

<400> SEQUENCE: 4

```
Met Ile Leu Asp Ala Asp Tyr Ile Thr Glu Asp Gly Lys Pro Val Val
1               5                  10                  15

Arg Ile Phe Arg Lys Glu Lys Gly Glu Phe Arg Ile Asp Tyr Asp Arg
            20                  25                  30

Asp Phe Glu Pro Tyr Ile Tyr Ala Leu Leu Lys Asp Asp Ser Ala Ile
        35                  40                  45

Glu Glu Val Lys Arg Ile Thr Val Glu Arg His Gly Lys Ala Val Arg
    50                  55                  60

Val Lys Arg Val Glu Lys Val Glu Lys Lys Phe Leu Asn Arg Pro Ile
65                  70                  75                  80

Glu Val Trp Lys Leu Tyr Phe Asn His Pro Gln Asp Val Pro Ala Ile
                85                  90                  95

Arg Asp Glu Ile Arg Lys His Pro Ala Val Val Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Glu Glu Leu Lys Leu Met Ala Phe Asp Ile Glu Thr
    130                 135                 140

Leu Tyr His Glu Gly Asp Glu Phe Gly Glu Gly Pro Ile Leu Met Ile
145                 150                 155                 160

Ser Tyr Ala Asp Gly Asp Gly Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Gln Val Val Lys Glu Lys Asp Pro Asp Val Leu Val Thr
        195                 200                 205

Tyr Asn Gly Asp Asn Phe Asp Phe Ala Tyr Leu Lys Arg Arg Ser Glu
    210                 215                 220

Glu Leu Gly Leu Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Val Asn Leu Pro Thr
            260                 265                 270

Tyr Thr Leu Glu Ala Val Tyr Glu Ala Ile Phe Gly Arg Pro Lys Glu
        275                 280                 285

Lys Val Tyr Ala Gly Glu Ile Val Glu Ala Trp Glu Thr Gly Glu Gly
    290                 295                 300

Leu Glu Arg Val Ala Arg Tyr Ser Met Glu Asp Ala Lys Val Thr Phe
305                 310                 315                 320

Glu Leu Gly Arg Glu Phe Phe Pro Met Glu Ala Gln Leu Ser Arg Leu
                325                 330                 335
```

```
Ile Gly Gln Gly Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Ser Gly Arg Glu Val Glu Ile Arg Arg Gly Tyr
            370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Asn Tyr Asp
            420                 425                 430

Val Ala Pro Gln Val Gly His Lys Phe Cys Lys Asp Phe Pro Gly Phe
            435                 440                 445

Ile Pro Ser Leu Leu Gly Gly Leu Leu Glu Glu Arg Gln Lys Ile Lys
            450                 455                 460

Arg Arg Met Lys Ala Ser Val Asp Pro Val Glu Arg Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Arg Ala Arg Trp Tyr Cys Arg Glu Cys Ala Glu Ser
            500                 505                 510

Val Thr Ala Trp Gly Arg Glu Tyr Ile Asp Arg Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Gly Thr Val Lys Glu Arg Ala
545                 550                 555                 560

Arg Gly Phe Leu Arg Tyr Ile Asn Pro Lys Leu Pro Gly Leu Leu Glu
                565                 570                 575

Leu Glu Tyr Glu Gly Phe Tyr Leu Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Val Ala Lys Glu Thr Gln Ala
610                 615                 620

Arg Val Leu Glu Ala Ile Leu Arg His Gly Asp Val Glu Glu Ala Val
625                 630                 635                 640

Arg Ile Val Arg Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Gly
            675                 680                 685

Arg Gly Val Arg Ile Arg Pro Gly Thr Val Ile Ser Tyr Ile Val Leu
            690                 695                 700

Lys Gly Ser Gly Arg Ile Gly Asp Arg Ala Ile Pro Phe Asp Glu Phe
705                 710                 715                 720

Asp Pro Thr Lys His Arg Tyr Asp Ala Asp Tyr Tyr Ile Glu Asn Gln
                725                 730                 735

Val Leu Pro Ala Val Glu Arg Ile Leu Lys Ala Phe Gly Tyr Arg Lys
            740                 745                 750
```

```
Glu Asp Leu Lys Tyr Gln Lys Thr Arg Gln Val Gly Leu Gly Ala Trp
        755                 760                 765
Leu Asn Ala Gly Lys Gly
    770

<210> SEQ ID NO 5
<211> LENGTH: 2328
<212> TYPE: DNA
<213> ORGANISM: Artificial Sequence
<220> FEATURE:
<223> OTHER INFORMATION: DNA polymerase from Thermococcus siculi

<400> SEQUENCE: 5
atgatcctcg acacggacta catcacggaa gatgggaaac ccgtcataag gatattcaag      60
aaagagaacg gcgagttcaa gatcgagtac gacaggactt tgaacccta catctacgcc     120 ctcctgaagg acgactccgc gattgaggat gttaaaaaga taaccgccga gaggcacgga    180
acggtggtga aggtcaagcg cgccgaaaag gtgcagaaga agttcctagg caggccggtt    240
gaagtctgga agctctactt cacccacccc caagatgtcc cggcgataag ggacaagatt    300
aggaagcatc cagctgtaat tgacatctac gagtacgaca taccattcgc caagcgctac    360
ctcatcgaca agggcctgat tccgatggag ggtgaagaag gcttaagat gctcgccttc    420 gacattgaga cgctctacca tgagggtgag gagttcgccg aggggcctat tctgatgata    480
agctacgccg acgagagcga ggcacgcgtc atcacctgga gaaaatcga cctcccctac    540 gttgacgtcg tctcaacgga gaaggagatg ataaagcgct ccttccgcgt tgtgaaggag    600
aaagatcccg atgtcctcat aacctacaac ggcgacaact tcgacttcgc ctacctgaag    660
aagcgctgtg aaaagcttgg aataaacttc ctccttggaa gggacgggag cgagccgaag    720
atccagagaa tgggtgaccg cttcgccgtt gaggtgaagg gaggatacaa cttcgacctc    780
tatcctgtaa taaggcgcac gataaacctg ccgacctaca tgcttgaggc agtctacgag    840
gccatctttg gaagccaaaa ggagaaggtt tacgccgagg atagccacg cgcttgggaa    900 accggagagg gccttgagag ggtggctcgc tactctatgg aggacgcgaa ggtcacgttt    960
gagcttggaa aggagttctt cccgatggag gcccaacttt cgaggttggt cggccagagc   1020
ttctgggatg tcgcgcgctc aagcacgggc aatctggtcg agtggttcct cctcaggaag   1080
gcctacgaga ggaacgagct ggctccaaac aagccctctg aagggaata tgacgagagg   1140 cgcggtggat acgccggcgg ctacgtcaag gaaccggaaa agggcctgtg ggagaacata   1200
gtctacctcg actataaatc tctctacccc tcaatcatca tcacccacaa cgtctcgccc   1260 gatacccctca accgcgaggg ctgtaaggag tatgacgtag ctccacaggt cggccaccgc   1320
ttctgcaagg actttccagg cttcatcccg agcctgctcg gggatctcct ggaggagagg   1380
cagaagataa agaggaagat gaaggcaaca attgacccga tcgagagaaa gctccttgat   1440
tacaggcaac gggccatcaa gatccttcta aatagttttt acggctacta cggctacgca   1500
agggctcgct ggtactgcaa ggagtgtgcc gagagcgtta cggcatgggg aagggaatat   1560
atcaccatga caatcaggga aatagaagag aagtatggct ttaaagtact ttatgcggac   1620
actgacggct tcttcgcgac gattcccggg aagatgccg agaccatcaa aaagagggcg   1680
atggagttcc tcaagtacat aaacgccaaa ctccccggtg cgctcgaact tgagtacgag   1740
gacttctaca ggcgcggctt cttcgtcacc aagaagaaat acgcggttat cgacgaggag   1800
ggcaagataa caacgcgcgg gctggagatc gtcaggcgcg actggagcga gatagccaag   1860
gagacgcagg cgcgggttct ggaggccctt ctgaaggacg gtgacgtcga gaggccgtg   1920
```

-continued

```
agcatagtca aagaagtgac cgagaagctg agcaagtacg aggttccgcc ggagaagctc    1980
gttatccacg agcagataac gcgcgagctg aaggactaca aggcaacggg accacacgtg    2040
gcgatagcga agaggttagc cgcgagaggc gtcaaaatcc gccccgggac agtcatcagc    2100
tacatcgtgc tcaagggctc cggaggata  ggcgacaggg cgattccctt cgacgagttc    2160
gaccccacga agcacaagta cgatgcagag tactacatcg agaaccaggt tctacctgcc    2220
gtcgagagga ttctgaaggc cttcggctat cgcggtgagg agctcagata ccagaagacg    2280
aggcaggttg gacttggggc gtggctgaag ccgaagggga aggggtga                 2328
```

<210> SEQ ID NO 6
<211> LENGTH: 775
<212> TYPE: PRT
<213> ORGANISM: Artificial Sequence
<220> FEATURE:
<223> OTHER INFORMATION: DNA polymerase from Thermococcus siculi

<400> SEQUENCE: 6

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Val Val Lys
    50                  55                  60

Val Lys Arg Ala Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Leu Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Met Leu Glu Ala Val Tyr Glu Ala Ile Phe Gly Lys Pro Lys Glu
        275                 280                 285
```

```
Lys Val Tyr Ala Glu Glu Ile Ala Thr Ala Trp Glu Thr Gly Gly
    290                 295                 300

Leu Glu Arg Val Ala Arg Tyr Ser Met Glu Asp Ala Lys Val Thr Phe
305                 310                 315                 320

Glu Leu Gly Lys Glu Phe Phe Pro Met Glu Ala Gln Leu Ser Arg Leu
                325                 330                 335

Val Gly Gln Ser Phe Trp Asp Val Ala Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Ser Gly Arg Glu Tyr Asp Arg Arg Gly Gly Tyr
    370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Ile Asp Pro Ile Glu Arg Lys Leu Leu Asp
465                 470                 475                 480

Tyr Arg Gln Arg Ala Ile Lys Ile Leu Leu Asn Ser Phe Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Arg Glu Ile
        515                 520                 525

Glu Glu Lys Tyr Gly Phe Lys Val Leu Tyr Ala Asp Thr Asp Gly Phe
    530                 535                 540

Phe Ala Thr Ile Pro Gly Glu Asp Ala Glu Thr Ile Lys Lys Arg Ala
545                 550                 555                 560

Met Glu Phe Leu Lys Tyr Ile Asn Ala Lys Leu Pro Gly Ala Leu Glu
                565                 570                 575

Leu Glu Tyr Glu Asp Phe Tyr Arg Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Glu Ala Val
625                 630                 635                 640

Ser Ile Val Lys Glu Val Thr Glu Lys Leu Ser Lys Tyr Glu Val Pro
                645                 650                 655

Pro Glu Lys Leu Val Ile His Glu Gln Ile Thr Arg Glu Leu Lys Asp
            660                 665                 670

Tyr Lys Ala Thr Gly Pro His Val Ala Ile Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
```

```
                705                 710                 715                 720

Asp Pro Thr Lys His Lys Tyr Asp Ala Glu Tyr Tyr Ile Glu Asn Gln
                    725                 730                 735

Val Leu Pro Ala Val Glu Arg Ile Leu Lys Ala Phe Gly Tyr Arg Gly
                    740                 745                 750

Glu Glu Leu Arg Tyr Gln Lys Thr Arg Gln Val Gly Leu Gly Ala Trp
                    755                 760                 765

Leu Lys Pro Lys Gly Lys Gly
                    770                 775

<210> SEQ ID NO 7
<211> LENGTH: 774
<212> TYPE: PRT
<213> ORGANISM: Artificial Sequence
<220> FEATURE:
<223> OTHER INFORMATION: DNA polymerase from Thermococcus kodakarensis

<400> SEQUENCE: 7

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
        50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Asp Ile Glu Thr
        130                 135                 140

Leu Tyr Glu Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
                180                 185                 190

Arg Phe Leu Arg Val Val Lys Glu Lys Asp Pro Asp Val Leu Ile Thr
            195                 200                 205

Tyr Asn Gly Asp Asn Phe Asp Phe Ala Tyr Leu Lys Lys Arg Cys Glu
        210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Gln Pro Lys Glu
            275                 280                 285

Lys Val Tyr Ala Glu Glu Ile Thr Thr Ala Trp Glu Thr Gly Glu Asn
```

```
                    290                 295                 300
Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Gln Ser Tyr
370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
            530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Glu Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
                660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Phe Asp Glu Phe
705                 710                 715                 720
```

-continued

Asp Pro Thr Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
        740                 745                 750

Glu Asp Leu Arg Tyr Gln Lys Thr Arg Gln Val Gly Leu Ser Ala Trp
    755                 760                 765

Leu Lys Pro Lys Gly Thr
    770

<210> SEQ ID NO 8
<211> LENGTH: 13
<212> TYPE: DNA
<213> ORGANISM: Artificial Sequence
<220> FEATURE:
<223> OTHER INFORMATION: Sample tag sequence

<400> SEQUENCE: 8
tagaattgaa gaa                                                          13

<210> SEQ ID NO 9
<211> LENGTH: 13
<212> TYPE: DNA
<213> ORGANISM: Artificial Sequence
<220> FEATURE:
<223> OTHER INFORMATION: Sample tag sequence

<400> SEQUENCE: 9
tggccatagc tac                                                          13

<210> SEQ ID NO 10
<211> LENGTH: 13
<212> TYPE: DNA
<213> ORGANISM: Artificial Sequence
<220> FEATURE:
<223> OTHER INFORMATION: Sample tag sequence

<400> SEQUENCE: 10
gtcatctgcg acc                                                          13

<210> SEQ ID NO 11
<211> LENGTH: 13
<212> TYPE: DNA
<213> ORGANISM: Artificial Sequence
<220> FEATURE:
<223> OTHER INFORMATION: Sample tag sequence

<400> SEQUENCE: 11
ttcgcgcttg gac                                                          13

<210> SEQ ID NO 12
<211> LENGTH: 13
<212> TYPE: DNA
<213> ORGANISM: Artificial Sequence
<220> FEATURE:
<223> OTHER INFORMATION: Sample tag sequence

<400> SEQUENCE: 12
cgcgaaccgt tag                                                          13

<210> SEQ ID NO 13
<211> LENGTH: 13
<212> TYPE: DNA
<213> ORGANISM: Artificial Sequence
<220> FEATURE:

```
<223> OTHER INFORMATION: Sample tag sequence

<400> SEQUENCE: 13
ttgcagcctc taa                                                              13

<210> SEQ ID NO 14
<211> LENGTH: 13
<212> TYPE: DNA
<213> ORGANISM: Artificial Sequence
<220> FEATURE:
<223> OTHER INFORMATION: Sample tag sequence

<400> SEQUENCE: 14
tctactagta cga                                                              13

<210> SEQ ID NO 15
<211> LENGTH: 13
<212> TYPE: DNA
<213> ORGANISM: Artificial Sequence
<220> FEATURE:
<223> OTHER INFORMATION: Sample tag sequence

<400> SEQUENCE: 15
gtaggttcta ctg                                                              13

<210> SEQ ID NO 16
<211> LENGTH: 13
<212> TYPE: DNA
<213> ORGANISM: Artificial Sequence
<220> FEATURE:
<223> OTHER INFORMATION: Sample tag sequence

<400> SEQUENCE: 16
gccaatatca agt                                                              13

<210> SEQ ID NO 17
<211> LENGTH: 13
<212> TYPE: DNA
<213> ORGANISM: Artificial Sequence
<220> FEATURE:
<223> OTHER INFORMATION: Sample tag sequence

<400> SEQUENCE: 17
ctatcttgct ggt                                                              13

<210> SEQ ID NO 18
<211> LENGTH: 13
<212> TYPE: DNA
<213> ORGANISM: Artificial Sequence
<220> FEATURE:
<223> OTHER INFORMATION: Sample tag sequence

<400> SEQUENCE: 18
gttctcatag gta                                                              13

<210> SEQ ID NO 19
<211> LENGTH: 13
<212> TYPE: DNA
<213> ORGANISM: Artificial Sequence
<220> FEATURE:
<223> OTHER INFORMATION: Sample tag sequence

<400> SEQUENCE: 19
gtctatgaac caa                                                              13
```

```
<210> SEQ ID NO 20
<211> LENGTH: 13
<212> TYPE: DNA
<213> ORGANISM: Artificial Sequence
<220> FEATURE:
<223> OTHER INFORMATION: Sample tag sequence

<400> SEQUENCE: 20
cggagcgctt att                                                        13

<210> SEQ ID NO 21
<211> LENGTH: 13
<212> TYPE: DNA
<213> ORGANISM: Artificial Sequence
<220> FEATURE:
<223> OTHER INFORMATION: Sample tag sequence

<400> SEQUENCE: 21
tatgccatga gga                                                        13

<210> SEQ ID NO 22
<211> LENGTH: 13
<212> TYPE: DNA
<213> ORGANISM: Artificial Sequence
<220> FEATURE:
<223> OTHER INFORMATION: Sample tag sequence

<400> SEQUENCE: 22
atacgactcg gag                                                        13

<210> SEQ ID NO 23
<211> LENGTH: 13
<212> TYPE: DNA
<213> ORGANISM: Artificial Sequence
<220> FEATURE:
<223> OTHER INFORMATION: Sample tag sequence

<400> SEQUENCE: 23
gatggaactc agc                                                        13

<210> SEQ ID NO 24
<211> LENGTH: 13
<212> TYPE: DNA
<213> ORGANISM: Artificial Sequence
<220> FEATURE:
<223> OTHER INFORMATION: Sample tag sequence

<400> SEQUENCE: 24
ggacctgcat gaa                                                        13

<210> SEQ ID NO 25
<211> LENGTH: 13
<212> TYPE: DNA
<213> ORGANISM: Artificial Sequence
<220> FEATURE:
<223> OTHER INFORMATION: Sample tag sequence

<400> SEQUENCE: 25
tagactggaa ctt                                                        13

<210> SEQ ID NO 26
<211> LENGTH: 13
<212> TYPE: DNA
<213> ORGANISM: Artificial Sequence
<220> FEATURE:
<223> OTHER INFORMATION: Sample tag sequence
```

```
<400> SEQUENCE: 26
gaattacctc gtt                                                          13

<210> SEQ ID NO 27
<211> LENGTH: 13
<212> TYPE: DNA
<213> ORGANISM: Artificial Sequence
<220> FEATURE:
<223> OTHER INFORMATION: Sample tag sequence

<400> SEQUENCE: 27
aggatcaggc tac                                                          13

<210> SEQ ID NO 28
<211> LENGTH: 13
<212> TYPE: DNA
<213> ORGANISM: Artificial Sequence
<220> FEATURE:
<223> OTHER INFORMATION: Sample tag sequence

<400> SEQUENCE: 28
acgcgtagaa gag                                                          13

<210> SEQ ID NO 29
<211> LENGTH: 13
<212> TYPE: DNA
<213> ORGANISM: Artificial Sequence
<220> FEATURE:
<223> OTHER INFORMATION: Sample tag sequence

<400> SEQUENCE: 29
cttcgagact tac                                                          13

<210> SEQ ID NO 30
<211> LENGTH: 13
<212> TYPE: DNA
<213> ORGANISM: Artificial Sequence
<220> FEATURE:
<223> OTHER INFORMATION: Sample tag sequence

<400> SEQUENCE: 30
gacggctaac tcc                                                          13

<210> SEQ ID NO 31
<211> LENGTH: 13
<212> TYPE: DNA
<213> ORGANISM: Artificial Sequence
<220> FEATURE:
<223> OTHER INFORMATION: Sample tag sequence

<400> SEQUENCE: 31
ttagcattct ctt                                                          13

<210> SEQ ID NO 32
<211> LENGTH: 13
<212> TYPE: DNA
<213> ORGANISM: Artificial Sequence
<220> FEATURE:
<223> OTHER INFORMATION: Sample tag sequence

<400> SEQUENCE: 32
gcaaggcata gta                                                          13

<210> SEQ ID NO 33
<211> LENGTH: 13
```

```
<212> TYPE: DNA
<213> ORGANISM: Artificial Sequence
<220> FEATURE:
<223> OTHER INFORMATION: Sample tag sequence

<400> SEQUENCE: 33
acctagatat gga                                                          13

<210> SEQ ID NO 34
<211> LENGTH: 13
<212> TYPE: DNA
<213> ORGANISM: Artificial Sequence
<220> FEATURE:
<223> OTHER INFORMATION: Sample tag sequence

<400> SEQUENCE: 34
acgccaaggc gta                                                          13

<210> SEQ ID NO 35
<211> LENGTH: 13
<212> TYPE: DNA
<213> ORGANISM: Artificial Sequence
<220> FEATURE:
<223> OTHER INFORMATION: Sample tag sequence

<400> SEQUENCE: 35
tatgacggat ccg                                                          13

<210> SEQ ID NO 36
<211> LENGTH: 13
<212> TYPE: DNA
<213> ORGANISM: Artificial Sequence
<220> FEATURE:
<223> OTHER INFORMATION: Sample tag sequence

<400> SEQUENCE: 36
cctccattag aga                                                          13

<210> SEQ ID NO 37
<211> LENGTH: 13
<212> TYPE: DNA
<213> ORGANISM: Artificial Sequence
<220> FEATURE:
<223> OTHER INFORMATION: Sample tag sequence

<400> SEQUENCE: 37
attgaatact ctg                                                          13

<210> SEQ ID NO 38
<211> LENGTH: 13
<212> TYPE: DNA
<213> ORGANISM: Artificial Sequence
<220> FEATURE:
<223> OTHER INFORMATION: Sample tag sequence

<400> SEQUENCE: 38
gagatgagaa gaa                                                          13

<210> SEQ ID NO 39
<211> LENGTH: 13
<212> TYPE: DNA
<213> ORGANISM: Artificial Sequence
<220> FEATURE:
<223> OTHER INFORMATION: Sample tag sequence

<400> SEQUENCE: 39
```

-continued

```
tctgagtagc cgg                                                        13

<210> SEQ ID NO 40
<211> LENGTH: 13
<212> TYPE: DNA
<213> ORGANISM: Artificial Sequence
<220> FEATURE:
<223> OTHER INFORMATION: Sample tag sequence

<400> SEQUENCE: 40
aataggtagt acg                                                        13

<210> SEQ ID NO 41
<211> LENGTH: 13
<212> TYPE: DNA
<213> ORGANISM: Artificial Sequence
<220> FEATURE:
<223> OTHER INFORMATION: Sample tag sequence

<400> SEQUENCE: 41
gtcgaagaag tcc                                                        13

<210> SEQ ID NO 42
<211> LENGTH: 13
<212> TYPE: DNA
<213> ORGANISM: Artificial Sequence
<220> FEATURE:
<223> OTHER INFORMATION: Sample tag sequence

<400> SEQUENCE: 42
tactgcatct cgt                                                        13

<210> SEQ ID NO 43
<211> LENGTH: 13
<212> TYPE: DNA
<213> ORGANISM: Artificial Sequence
<220> FEATURE:
<223> OTHER INFORMATION: Sample tag sequence

<400> SEQUENCE: 43
gacgtattag agc                                                        13

<210> SEQ ID NO 44
<211> LENGTH: 13
<212> TYPE: DNA
<213> ORGANISM: Artificial Sequence
<220> FEATURE:
<223> OTHER INFORMATION: Sample tag sequence

<400> SEQUENCE: 44
cctgcattat tcg                                                        13

<210> SEQ ID NO 45
<211> LENGTH: 13
<212> TYPE: DNA
<213> ORGANISM: Artificial Sequence
<220> FEATURE:
<223> OTHER INFORMATION: Sample tag sequence

<400> SEQUENCE: 45
acgaatgatg ctc                                                        13

<210> SEQ ID NO 46
<211> LENGTH: 13
<212> TYPE: DNA
<213> ORGANISM: Artificial Sequence
```

```
<220> FEATURE:
<223> OTHER INFORMATION: Sample tag sequence

<400> SEQUENCE: 46
tactagcaga gat                                                              13

<210> SEQ ID NO 47
<211> LENGTH: 13
<212> TYPE: DNA
<213> ORGANISM: Artificial Sequence
<220> FEATURE:
<223> OTHER INFORMATION: Sample tag sequence

<400> SEQUENCE: 47
ctcctcatct tcc                                                              13

<210> SEQ ID NO 48
<211> LENGTH: 13
<212> TYPE: DNA
<213> ORGANISM: Artificial Sequence
<220> FEATURE:
<223> OTHER INFORMATION: Sample tag sequence

<400> SEQUENCE: 48
tcctctgcgc tgc                                                              13

<210> SEQ ID NO 49
<211> LENGTH: 13
<212> TYPE: DNA
<213> ORGANISM: Artificial Sequence
<220> FEATURE:
<223> OTHER INFORMATION: Sample tag sequence

<400> SEQUENCE: 49
ccttctcagt ccg                                                              13

<210> SEQ ID NO 50
<211> LENGTH: 13
<212> TYPE: DNA
<213> ORGANISM: Artificial Sequence
<220> FEATURE:
<223> OTHER INFORMATION: Sample tag sequence

<400> SEQUENCE: 50
cagcttcata gcg                                                              13

<210> SEQ ID NO 51
<211> LENGTH: 13
<212> TYPE: DNA
<213> ORGANISM: Artificial Sequence
<220> FEATURE:
<223> OTHER INFORMATION: Sample tag sequence

<400> SEQUENCE: 51
ttgactctcg cgc                                                              13

<210> SEQ ID NO 52
<211> LENGTH: 13
<212> TYPE: DNA
<213> ORGANISM: Artificial Sequence
<220> FEATURE:
<223> OTHER INFORMATION: Sample tag sequence

<400> SEQUENCE: 52
tatcctgagc gat                                                              13
```

```
<210> SEQ ID NO 53
<211> LENGTH: 13
<212> TYPE: DNA
<213> ORGANISM: Artificial Sequence
<220> FEATURE:
<223> OTHER INFORMATION: Sample tag sequence

<400> SEQUENCE: 53
aacgcctagc cga                                                          13

<210> SEQ ID NO 54
<211> LENGTH: 13
<212> TYPE: DNA
<213> ORGANISM: Artificial Sequence
<220> FEATURE:
<223> OTHER INFORMATION: Sample tag sequence

<400> SEQUENCE: 54
ccgaagacgt cat                                                          13

<210> SEQ ID NO 55
<211> LENGTH: 13
<212> TYPE: DNA
<213> ORGANISM: Artificial Sequence
<220> FEATURE:
<223> OTHER INFORMATION: Sample tag sequence

<400> SEQUENCE: 55
gagttctcca gat                                                          13

<210> SEQ ID NO 56
<211> LENGTH: 13
<212> TYPE: DNA
<213> ORGANISM: Artificial Sequence
<220> FEATURE:
<223> OTHER INFORMATION: Sample tag sequence

<400> SEQUENCE: 56
tgcatccgcg ctt                                                          13

<210> SEQ ID NO 57
<211> LENGTH: 13
<212> TYPE: DNA
<213> ORGANISM: Artificial Sequence
<220> FEATURE:
<223> OTHER INFORMATION: Sample tag sequence

<400> SEQUENCE: 57
cctgaactca agt                                                          13

<210> SEQ ID NO 58
<211> LENGTH: 13
<212> TYPE: DNA
<213> ORGANISM: Artificial Sequence
<220> FEATURE:
<223> OTHER INFORMATION: sample tag sequence

<400> SEQUENCE: 58
ggtcgtatgc gta                                                          13

<210> SEQ ID NO 59
<211> LENGTH: 13
<212> TYPE: DNA
<213> ORGANISM: Artificial Sequence
<220> FEATURE:
<223> OTHER INFORMATION: Sample tag sequence
```

<400> SEQUENCE: 59
aggcctctct acc                                                                                              13

<210> SEQ ID NO 60
<211> LENGTH: 13
<212> TYPE: DNA
<213> ORGANISM: Artificial Sequence
<220> FEATURE:
<223> OTHER INFORMATION: Sample tag sequence

<400> SEQUENCE: 60
gtactccatc caa                                                                                              13

<210> SEQ ID NO 61
<211> LENGTH: 13
<212> TYPE: DNA
<213> ORGANISM: Artificial Sequence
<220> FEATURE:
<223> OTHER INFORMATION: Sample tag sequence

<400> SEQUENCE: 61
cagcggacgc gct                                                                                              13

<210> SEQ ID NO 62
<211> LENGTH: 13
<212> TYPE: DNA
<213> ORGANISM: Artificial Sequence
<220> FEATURE:
<223> OTHER INFORMATION: Sample tag sequence

<400> SEQUENCE: 62
atctctctta gca                                                                                              13

<210> SEQ ID NO 63
<211> LENGTH: 13
<212> TYPE: DNA
<213> ORGANISM: Artificial Sequence
<220> FEATURE:
<223> OTHER INFORMATION: Sample tag sequence

<400> SEQUENCE: 63
aagcaataat aat                                                                                              13

<210> SEQ ID NO 64
<211> LENGTH: 13
<212> TYPE: DNA
<213> ORGANISM: Artificial Sequence
<220> FEATURE:
<223> OTHER INFORMATION: Sample tag sequence

<400> SEQUENCE: 64
aaggcgactc cga                                                                                              13

<210> SEQ ID NO 65
<211> LENGTH: 13
<212> TYPE: DNA
<213> ORGANISM: Artificial Sequence
<220> FEATURE:
<223> OTHER INFORMATION: Sample tag sequence

<400> SEQUENCE: 65
acgtctctag gag                                                                                              13

<210> SEQ ID NO 66

```
<211> LENGTH: 13
<212> TYPE: DNA
<213> ORGANISM: Artificial Sequence
<220> FEATURE:
<223> OTHER INFORMATION: Sample tag sequence

<400> SEQUENCE: 66
ccatcagacc tct                                                          13

<210> SEQ ID NO 67
<211> LENGTH: 13
<212> TYPE: DNA
<213> ORGANISM: Artificial Sequence
<220> FEATURE:
<223> OTHER INFORMATION: Sample tag sequence

<400> SEQUENCE: 67
acttaatcgt act                                                          13

<210> SEQ ID NO 68
<211> LENGTH: 13
<212> TYPE: DNA
<213> ORGANISM: Artificial Sequence
<220> FEATURE:
<223> OTHER INFORMATION: Sample tag sequence

<400> SEQUENCE: 68
tggaattctc caa                                                          13

<210> SEQ ID NO 69
<211> LENGTH: 13
<212> TYPE: DNA
<213> ORGANISM: Artificial Sequence
<220> FEATURE:
<223> OTHER INFORMATION: Sample tag sequence

<400> SEQUENCE: 69 ccatcgatc agg                                                           13

<210> SEQ ID NO 70
<211> LENGTH: 13
<212> TYPE: DNA
<213> ORGANISM: Artificial Sequence
<220> FEATURE:
<223> OTHER INFORMATION: Sample tag sequence

<400> SEQUENCE: 70
ttatggagca ata                                                          13

<210> SEQ ID NO 71
<211> LENGTH: 13
<212> TYPE: DNA
<213> ORGANISM: Artificial Sequence
<220> FEATURE:
<223> OTHER INFORMATION: Sample tag sequence

<400> SEQUENCE: 71
gctcggcgtt cga                                                          13

<210> SEQ ID NO 72
<211> LENGTH: 13
<212> TYPE: DNA
<213> ORGANISM: Artificial Sequence
<220> FEATURE:
<223> OTHER INFORMATION: Sample tag sequence

<400> SEQUENCE: 72
```

```
ttggccagtc gct                                                           13

<210> SEQ ID NO 73
<211> LENGTH: 13
<212> TYPE: DNA
<213> ORGANISM: Artificial Sequence
<220> FEATURE:
<223> OTHER INFORMATION: Sample tag sequence

<400> SEQUENCE: 73
cagatacgta gag                                                           13

<210> SEQ ID NO 74
<211> LENGTH: 13
<212> TYPE: DNA
<213> ORGANISM: Artificial Sequence
<220> FEATURE:
<223> OTHER INFORMATION: Sample tag sequence

<400> SEQUENCE: 74
aatgctatta tcc                                                           13

<210> SEQ ID NO 75
<211> LENGTH: 13
<212> TYPE: DNA
<213> ORGANISM: Artificial Sequence
<220> FEATURE:
<223> OTHER INFORMATION: Sample tag sequence

<400> SEQUENCE: 75
gcagcatgcc gat                                                           13

<210> SEQ ID NO 76
<211> LENGTH: 13
<212> TYPE: DNA
<213> ORGANISM: Artificial Sequence
<220> FEATURE:
<223> OTHER INFORMATION: Sample tag sequence

<400> SEQUENCE: 76
ggagagttac ctc                                                           13

<210> SEQ ID NO 77
<211> LENGTH: 13
<212> TYPE: DNA
<213> ORGANISM: Artificial Sequence
<220> FEATURE:
<223> OTHER INFORMATION: Sample tag sequence

<400> SEQUENCE: 77
gagagtccat gat                                                           13

<210> SEQ ID NO 78
<211> LENGTH: 13
<212> TYPE: DNA
<213> ORGANISM: Artificial Sequence
<220> FEATURE:
<223> OTHER INFORMATION: Sample tag sequence

<400> SEQUENCE: 78
caatctattc tga                                                           13

<210> SEQ ID NO 79
<211> LENGTH: 13
<212> TYPE: DNA
```

```
<213> ORGANISM: Artificial Sequence
<220> FEATURE:
<223> OTHER INFORMATION: Sample tag sequence

<400> SEQUENCE: 79
gctcttagta tcc                                                          13

<210> SEQ ID NO 80
<211> LENGTH: 13
<212> TYPE: DNA
<213> ORGANISM: Artificial Sequence
<220> FEATURE:
<223> OTHER INFORMATION: Sample tag sequence

<400> SEQUENCE: 80
ccatagttat ggt                                                          13

<210> SEQ ID NO 81
<211> LENGTH: 13
<212> TYPE: DNA
<213> ORGANISM: Artificial Sequence
<220> FEATURE:
<223> OTHER INFORMATION: Sample tag sequence

<400> SEQUENCE: 81
tgcgagatcg aag                                                          13

<210> SEQ ID NO 82
<211> LENGTH: 13
<212> TYPE: DNA
<213> ORGANISM: Artificial Sequence
<220> FEATURE:
<223> OTHER INFORMATION: Sample tag sequence

<400> SEQUENCE: 82
agagaagtcg agt                                                          13

<210> SEQ ID NO 83
<211> LENGTH: 13
<212> TYPE: DNA
<213> ORGANISM: Artificial Sequence
<220> FEATURE:
<223> OTHER INFORMATION: Sample tag sequence

<400> SEQUENCE: 83
ggtaactcca tat                                                          13

<210> SEQ ID NO 84
<211> LENGTH: 13
<212> TYPE: DNA
<213> ORGANISM: Artificial Sequence
<220> FEATURE:
<223> OTHER INFORMATION: Sample tag sequence

<400> SEQUENCE: 84
tgctattcca ggc                                                          13

<210> SEQ ID NO 85
<211> LENGTH: 13
<212> TYPE: DNA
<213> ORGANISM: Artificial Sequence
<220> FEATURE:
<223> OTHER INFORMATION: Sample tag sequence

<400> SEQUENCE: 85
aaccgcgagg ctc                                                          13
```

```
<210> SEQ ID NO 86
<211> LENGTH: 13
<212> TYPE: DNA
<213> ORGANISM: Artificial Sequence
<220> FEATURE:
<223> OTHER INFORMATION: Sample tag sequence

<400> SEQUENCE: 86
ttctagagat acc                                                          13

<210> SEQ ID NO 87
<211> LENGTH: 13
<212> TYPE: DNA
<213> ORGANISM: Artificial Sequence
<220> FEATURE:
<223> OTHER INFORMATION: Sample tag sequence

<400> SEQUENCE: 87
ttcgctcaag tat                                                          13

<210> SEQ ID NO 88
<211> LENGTH: 13
<212> TYPE: DNA
<213> ORGANISM: Artificial Sequence
<220> FEATURE:
<223> OTHER INFORMATION: Sample tag sequence

<400> SEQUENCE: 88
cagagaaggc gca                                                          13

<210> SEQ ID NO 89
<211> LENGTH: 13
<212> TYPE: DNA
<213> ORGANISM: Artificial Sequence
<220> FEATURE:
<223> OTHER INFORMATION: Sample tag sequence

<400> SEQUENCE: 89
tagaattggc ctc                                                          13

<210> SEQ ID NO 90
<211> LENGTH: 13
<212> TYPE: DNA
<213> ORGANISM: Artificial Sequence
<220> FEATURE:
<223> OTHER INFORMATION: Sample tag sequence

<400> SEQUENCE: 90
ggccattctc cag                                                          13

<210> SEQ ID NO 91
<211> LENGTH: 13
<212> TYPE: DNA
<213> ORGANISM: Artificial Sequence
<220> FEATURE:
<223> OTHER INFORMATION: Sample tag sequence

<400> SEQUENCE: 91
tccaacgcgc gtt                                                          13

<210> SEQ ID NO 92
<211> LENGTH: 13
<212> TYPE: DNA
<213> ORGANISM: Artificial Sequence
<220> FEATURE:
```

```
<223> OTHER INFORMATION: Sample tag sequence

<400> SEQUENCE: 92
gccgcagatt acg                                                          13

<210> SEQ ID NO 93
<211> LENGTH: 13
<212> TYPE: DNA
<213> ORGANISM: Artificial Sequence
<220> FEATURE:
<223> OTHER INFORMATION: Sample tag sequence

<400> SEQUENCE: 93
gcagttcgaa cgc                                                          13

<210> SEQ ID NO 94
<211> LENGTH: 13
<212> TYPE: DNA
<213> ORGANISM: Artificial Sequence
<220> FEATURE:
<223> OTHER INFORMATION: Sample tag sequence

<400> SEQUENCE: 94
ttctctctgc agg                                                          13

<210> SEQ ID NO 95
<211> LENGTH: 13
<212> TYPE: DNA
<213> ORGANISM: Artificial Sequence
<220> FEATURE:
<223> OTHER INFORMATION: Sample tag sequence

<400> SEQUENCE: 95
taagctacca gcg                                                          13

<210> SEQ ID NO 96
<211> LENGTH: 13
<212> TYPE: DNA
<213> ORGANISM: Artificial Sequence
<220> FEATURE:
<223> OTHER INFORMATION: Sample tag sequence

<400> SEQUENCE: 96
ctgcatgagg ttg                                                          13

<210> SEQ ID NO 97
<211> LENGTH: 13
<212> TYPE: DNA
<213> ORGANISM: Artificial Sequence
<220> FEATURE:
<223> OTHER INFORMATION: Sample tag sequence

<400> SEQUENCE: 97
ttgcctagcg agg                                                          13

<210> SEQ ID NO 98
<211> LENGTH: 13
<212> TYPE: DNA
<213> ORGANISM: Artificial Sequence
<220> FEATURE:
<223> OTHER INFORMATION: Sample tag sequence

<400> SEQUENCE: 98
caactgaatt agg                                                          13
```

```
<210> SEQ ID NO 99
<211> LENGTH: 13
<212> TYPE: DNA
<213> ORGANISM: Artificial Sequence
<220> FEATURE:
<223> OTHER INFORMATION: Sample tag sequence

<400> SEQUENCE: 99
aagcggtcct ctt                                                        13

<210> SEQ ID NO 100
<211> LENGTH: 13
<212> TYPE: DNA
<213> ORGANISM: Artificial Sequence
<220> FEATURE:
<223> OTHER INFORMATION: Sample tag sequence

<400> SEQUENCE: 100
aatggaagga ccg                                                        13

<210> SEQ ID NO 101
<211> LENGTH: 13
<212> TYPE: DNA
<213> ORGANISM: Artificial Sequence
<220> FEATURE:
<223> OTHER INFORMATION: Sample tag sequence

<400> SEQUENCE: 101
gagttagtaa gtt                                                        13

<210> SEQ ID NO 102
<211> LENGTH: 13
<212> TYPE: DNA
<213> ORGANISM: Artificial Sequence
<220> FEATURE:
<223> OTHER INFORMATION: Sample tag sequence

<400> SEQUENCE: 102
ttcctaattc caa                                                        13

<210> SEQ ID NO 103
<211> LENGTH: 13
<212> TYPE: DNA
<213> ORGANISM: Artificial Sequence
<220> FEATURE:
<223> OTHER INFORMATION: Sample tag sequence

<400> SEQUENCE: 103
gttctggttc gct                                                        13

<210> SEQ ID NO 104
<211> LENGTH: 13
<212> TYPE: DNA
<213> ORGANISM: Artificial Sequence
<220> FEATURE:
<223> OTHER INFORMATION: Sample tag sequence

<400> SEQUENCE: 104
gttcatctct tcc                                                        13

<210> SEQ ID NO 105
<211> LENGTH: 13
<212> TYPE: DNA
<213> ORGANISM: Artificial Sequence
<220> FEATURE:
<223> OTHER INFORMATION: Sample tag sequence
```

```
<400> SEQUENCE: 105
attccgagga aga                                                    13

<210> SEQ ID NO 106
<211> LENGTH: 13
<212> TYPE: DNA
<213> ORGANISM: Artificial Sequence
<220> FEATURE:
<223> OTHER INFORMATION: Sample tag sequence

<400> SEQUENCE: 106
cttagccgag aga                                                    13

<210> SEQ ID NO 107
<211> LENGTH: 13
<212> TYPE: DNA
<213> ORGANISM: Artificial Sequence
<220> FEATURE:
<223> OTHER INFORMATION: Sample tag sequence

<400> SEQUENCE: 107
gtctgctacg ctt                                                    13

<210> SEQ ID NO 108
<211> LENGTH: 13
<212> TYPE: DNA
<213> ORGANISM: Artificial Sequence
<220> FEATURE:
<223> OTHER INFORMATION: Sample tag sequence

<400> SEQUENCE: 108
atggcgccgc gca                                                    13

<210> SEQ ID NO 109
<211> LENGTH: 13
<212> TYPE: DNA
<213> ORGANISM: Artificial Sequence
<220> FEATURE:
<223> OTHER INFORMATION: Sample tag sequence

<400> SEQUENCE: 109
taattggtta tct                                                    13

<210> SEQ ID NO 110
<211> LENGTH: 13
<212> TYPE: DNA
<213> ORGANISM: Artificial Sequence
<220> FEATURE:
<223> OTHER INFORMATION: Sample tag sequence

<400> SEQUENCE: 110
tcggttataa gtc                                                    13

<210> SEQ ID NO 111
<211> LENGTH: 13
<212> TYPE: DNA
<213> ORGANISM: Artificial Sequence
<220> FEATURE:
<223> OTHER INFORMATION: Sample tag sequence

<400> SEQUENCE: 111
tgcctgagaa cgt                                                    13

<210> SEQ ID NO 112
<211> LENGTH: 13
```

```
<212> TYPE: DNA
<213> ORGANISM: Artificial Sequence
<220> FEATURE:
<223> OTHER INFORMATION: Sample tag sequence

<400> SEQUENCE: 112
agatgcggtt aac                                                    13

<210> SEQ ID NO 113
<211> LENGTH: 13
<212> TYPE: DNA
<213> ORGANISM: Artificial Sequence
<220> FEATURE:
<223> OTHER INFORMATION: Sample tag sequence

<400> SEQUENCE: 113
atggaatagg cga                                                    13

<210> SEQ ID NO 114
<211> LENGTH: 13
<212> TYPE: DNA
<213> ORGANISM: Artificial Sequence
<220> FEATURE:
<223> OTHER INFORMATION: Sample tag sequence

<400> SEQUENCE: 114
agagatgcga tcg                                                    13

<210> SEQ ID NO 115
<211> LENGTH: 13
<212> TYPE: DNA
<213> ORGANISM: Artificial Sequence
<220> FEATURE:
<223> OTHER INFORMATION: Sample tag sequence

<400> SEQUENCE: 115
ctccaactaa cgt                                                    13

<210> SEQ ID NO 116
<211> LENGTH: 13
<212> TYPE: DNA
<213> ORGANISM: Artificial Sequence
<220> FEATURE:
<223> OTHER INFORMATION: Sample tag sequence

<400> SEQUENCE: 116
gccttgctac tgg                                                    13

<210> SEQ ID NO 117
<211> LENGTH: 13
<212> TYPE: DNA
<213> ORGANISM: Artificial Sequence
<220> FEATURE:
<223> OTHER INFORMATION: Sample tag sequence

<400> SEQUENCE: 117
cttcgtctct acg                                                    13

<210> SEQ ID NO 118
<211> LENGTH: 13
<212> TYPE: DNA
<213> ORGANISM: Artificial Sequence
<220> FEATURE:
<223> OTHER INFORMATION: Sample tag sequence

<400> SEQUENCE: 118
```
acgctcatag cct                              13

<210> SEQ ID NO 119
<211> LENGTH: 13
<212> TYPE: DNA
<213> ORGANISM: Artificial Sequence
<220> FEATURE:
<223> OTHER INFORMATION: Sample tag sequence

<400> SEQUENCE: 119
gtcgaagata agg                              13

<210> SEQ ID NO 120
<211> LENGTH: 13
<212> TYPE: DNA
<213> ORGANISM: Artificial Sequence
<220> FEATURE:
<223> OTHER INFORMATION: Sample tag sequence

<400> SEQUENCE: 120
gccggagtcc tcg                              13

<210> SEQ ID NO 121
<211> LENGTH: 13
<212> TYPE: DNA
<213> ORGANISM: Artificial Sequence
<220> FEATURE:
<223> OTHER INFORMATION: Sample tag sequence

<400> SEQUENCE: 121
tatacggcga cct                              13

<210> SEQ ID NO 122
<211> LENGTH: 13
<212> TYPE: DNA
<213> ORGANISM: Artificial Sequence
<220> FEATURE:
<223> OTHER INFORMATION: Sample tag sequence

<400> SEQUENCE: 122
aggtagatat tcg                              13

<210> SEQ ID NO 123
<211> LENGTH: 13
<212> TYPE: DNA
<213> ORGANISM: Artificial Sequence
<220> FEATURE:
<223> OTHER INFORMATION: Sample tag sequence

<400> SEQUENCE: 123
ttaaggtact gct                              13

<210> SEQ ID NO 124
<211> LENGTH: 13
<212> TYPE: DNA
<213> ORGANISM: Artificial Sequence
<220> FEATURE:
<223> OTHER INFORMATION: Sample tag sequence

<400> SEQUENCE: 124
cggatctggt ata                              13

<210> SEQ ID NO 125
<211> LENGTH: 13
<212> TYPE: DNA
<213> ORGANISM: Artificial Sequence

```
<220> FEATURE:
<223> OTHER INFORMATION: Sample tag sequence

<400> SEQUENCE: 125
gaggtctcgg agg                                                              13

<210> SEQ ID NO 126
<211> LENGTH: 13
<212> TYPE: DNA
<213> ORGANISM: Artificial Sequence
<220> FEATURE:
<223> OTHER INFORMATION: Sample tag sequence

<400> SEQUENCE: 126
ggcatcgatg gac                                                              13

<210> SEQ ID NO 127
<211> LENGTH: 13
<212> TYPE: DNA
<213> ORGANISM: Artificial Sequence
<220> FEATURE:
<223> OTHER INFORMATION: Sample tag sequence

<400> SEQUENCE: 127
gatctccgat ata                                                              13

<210> SEQ ID NO 128
<211> LENGTH: 13
<212> TYPE: DNA
<213> ORGANISM: Artificial Sequence
<220> FEATURE:
<223> OTHER INFORMATION: Sample tag sequence

<400> SEQUENCE: 128
gattcggaat act                                                              13

<210> SEQ ID NO 129
<211> LENGTH: 13
<212> TYPE: DNA
<213> ORGANISM: Artificial Sequence
<220> FEATURE:
<223> OTHER INFORMATION: Sample tag sequence

<400> SEQUENCE: 129
ctgcgatccg gcc                                                              13

<210> SEQ ID NO 130
<211> LENGTH: 13
<212> TYPE: DNA
<213> ORGANISM: Artificial Sequence
<220> FEATURE:
<223> OTHER INFORMATION: Sample tag sequence

<400> SEQUENCE: 130
gatccggttg caa                                                              13

<210> SEQ ID NO 131
<211> LENGTH: 13
<212> TYPE: DNA
<213> ORGANISM: Artificial Sequence
<220> FEATURE:
<223> OTHER INFORMATION: Sample tag sequence

<400> SEQUENCE: 131
cgtcaggctt gac                                                              13
```

```
<210> SEQ ID NO 132
<211> LENGTH: 13
<212> TYPE: DNA
<213> ORGANISM: Artificial Sequence
<220> FEATURE:
<223> OTHER INFORMATION: Sample tag sequence

<400> SEQUENCE: 132
tcggcaaggc gag                                                          13

<210> SEQ ID NO 133
<211> LENGTH: 13
<212> TYPE: DNA
<213> ORGANISM: Artificial Sequence
<220> FEATURE:
<223> OTHER INFORMATION: Sample tag sequence

<400> SEQUENCE: 133
gaacggcgaa cgc                                                          13

<210> SEQ ID NO 134
<211> LENGTH: 13
<212> TYPE: DNA
<213> ORGANISM: Artificial Sequence
<220> FEATURE:
<223> OTHER INFORMATION: Sample tag sequence

<400> SEQUENCE: 134
cctcaagcgg act                                                          13

<210> SEQ ID NO 135
<211> LENGTH: 13
<212> TYPE: DNA
<213> ORGANISM: Artificial Sequence
<220> FEATURE:
<223> OTHER INFORMATION: Sample tag sequence

<400> SEQUENCE: 135
gaagccagat ggt                                                          13

<210> SEQ ID NO 136
<211> LENGTH: 13
<212> TYPE: DNA
<213> ORGANISM: Artificial Sequence
<220> FEATURE:
<223> OTHER INFORMATION: Sample tag sequence

<400> SEQUENCE: 136
tgctcatacc aat                                                          13

<210> SEQ ID NO 137
<211> LENGTH: 51
<212> TYPE: DNA
<213> ORGANISM: Artificial Sequence
<220> FEATURE:
<223> OTHER INFORMATION: i7 custom index primer (Table 2)
<220> FEATURE:
<221> NAME/KEY: misc_feature
<222> LOCATION: (25)..(36)
<223> OTHER INFORMATION: n is a, c, g, or t

<400> SEQUENCE: 137
caagcagaag acggcatacg agatnnnnnn nnnnnngtct cgtgggctcg g                 51

<210> SEQ ID NO 138
<211> LENGTH: 55
```

```
<212> TYPE: DNA
<213> ORGANISM: Artificial Sequence
<220> FEATURE:
<223> OTHER INFORMATION: i5 custom index primer (Table 2)
<220> FEATURE:
<221> NAME/KEY: misc_feature
<222> LOCATION: (30)..(41)
<223> OTHER INFORMATION: n is a, c, g, or t

<400> SEQUENCE: 138
aatgatacgg cgaccaccga gatctacacn nnnnnnnnnn ntcgtcggca gcgtc      55

<210> SEQ ID NO 139
<211> LENGTH: 21
<212> TYPE: DNA
<213> ORGANISM: Artificial Sequence
<220> FEATURE:
<223> OTHER INFORMATION: i7 flow cell primer (Table 3)

<400> SEQUENCE: 139
caagcagaag acggcatacg a                                           21

<210> SEQ ID NO 140
<211> LENGTH: 20
<212> TYPE: DNA
<213> ORGANISM: Artificial Sequence
<220> FEATURE:
<223> OTHER INFORMATION: i5 flow cell primer (Table 3)

<400> SEQUENCE: 140
aatgatacgg cgaccaccga                                             20

<210> SEQ ID NO 141
<211> LENGTH: 51
<212> TYPE: DNA
<213> ORGANISM: Artificial Sequence
<220> FEATURE:
<223> OTHER INFORMATION: single_mut for mutagenesis (Table 5)
<220> FEATURE:
<221> NAME/KEY: misc_feature
<222> LOCATION: (19)..(34)
<223> OTHER INFORMATION: n is a, c, g, or t

<400> SEQUENCE: 141
tcggtctgcg cctctagcnn nnnnnnnnnn nnnngtctcg tgggctcgga g          51

<210> SEQ ID NO 142
<211> LENGTH: 42
<212> TYPE: DNA
<213> ORGANISM: Artificial Sequence
<220> FEATURE:
<223> OTHER INFORMATION: single_rec primer for recovery (Table 5)

<400> SEQUENCE: 142
caagcagaag acggcatacg agattcggtc tgcgcctcta gc                    42
```

UNITED STATES PATENT AND TRADEMARK OFFICE
CERTIFICATE OF CORRECTION

PATENT NO. : 12,203,076 B2
APPLICATION NO. : 17/807835
DATED : January 21, 2025
INVENTOR(S) : Leigh G. Monahan et al.

It is certified that error appears in the above-identified patent and that said Letters Patent is hereby corrected as shown below:

In the Claims

In Column 103, Line 36, in Claim 10, delete "3%, of 2%" and insert -- 3% --.

Signed and Sealed this
Twenty-fifth Day of March, 2025

Coke Morgan Stewart
*Acting Director of the United States Patent and Trademark Office*